United States Patent [19]

Coulton et al.

[11] Patent Number: 5,612,477

[45] Date of Patent: Mar. 18, 1997

[54] 2-(PYRAZOL-3-YL)CARBAPENEM DERIVATIVES

[75] Inventors: Steven Coulton; Jeremy D. Hinks, both of Horsham; Eric Hunt, Betchworth, all of England

[73] Assignee: SmithKline Beecham p.l.c

[21] Appl. No.: 457,002

[22] Filed: Jun. 1, 1995

Related U.S. Application Data

[63] Continuation of PCT/GB94/02347 Oct. 25, 1994 published as WO95/11905 May 4, 1995.

[30] Foreign Application Priority Data

Oct. 29, 1993 [GB] United Kingdom .................... 9322284
Jun. 1, 1994 [GB] United Kingdom .................... 9410929

[51] Int. Cl.$^6$ .................................................. C07D 487/04
[52] U.S. Cl. ............................................................ 540/302
[58] Field of Search ............................................ 540/302

[56] References Cited

FOREIGN PATENT DOCUMENTS

| 0010316 | 4/1980 | European Pat. Off. . |
|---|---|---|
| 430037 | 5/1991 | European Pat. Off. . |
| 444889 | 9/1991 | European Pat. Off. . |
| 0564270A1 | 10/1993 | European Pat. Off. . |
| 1593524 | 7/1981 | United Kingdom . |

*Primary Examiner*—Rebecca Cook
*Attorney, Agent, or Firm*—Wayne J. Dustman; Charles M. Kinzig; Edward T. Lentz

[57] ABSTRACT

Disclosed are a carbapenem compound represented by formula (I) and processes to its preparation.

5 Claims, No Drawings

2-(PYRAZOL-3-YL)CARBAPENEM DERIVATIVES

This is a continuation of application Ser. No. PCT/GB94/02347, filed Oct. 25, 1994, published as WO95/01905 May 4, 1995.

This invention relates to a class of antibacterial compounds, in particular a class of carbapenems, processes for their preparation, pharmaceutical and veterinary compositions comprising such compounds, intermediates thereof, and their use in antibacterial therapy.

Carbapenems such as imipenem, the compound of formula (A):

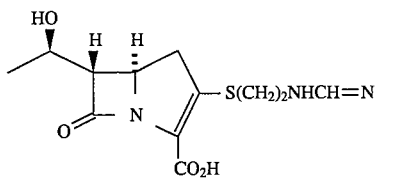

have a potent, broad spectrum of antibacterial activity (see U.S. Pat. Nos. 3,950,357 and 4,194,047; Merck and Co). Such carbapenems however tend to be vulnerable to hydrolysis by the enzyme renal dehydropeptidase-1 (DHP-1) and this limits their use in chemotherapy. In the case of imipenem, this problem may be overcome by the co-administration of an inhibitor of DHP-1.

Stability, towards DHP-1 may also be imparted by chemical modification of the carbapenem nucleus, for instance by incorporating a 1β-methyl substitutent, as in the compound meropenem, the compound of formula (B):

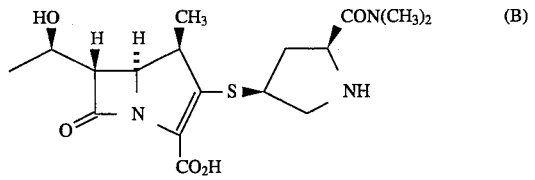

(see Shih D. H. et al., *Heterocycles*, 1984, 21, 29 and Sunagawa M. et al., J. Antibiotics, 1990, 43, 519). More recently, this has been extended to a 1β-aminoalkyl substituent (see EP 0 433 759, Bristol-Meyers Squibb).

An alternative approach to imparting improved stability to DHP-1 utilises 2-carbon substituted carbapenems, for instance, 2-aryl, 2-heteroaryl and 2-heteroaromatic carbapenems (U.S. Pat. Nos. 4,543,257, 4,260,627, 4,962,101, 4,978,659, EP 0 14 493, EP 0 414 489, EP 0 010 316 and EP 0 030 032 Merck & Co) and 2-(substituted)methyl carbapenems (Schmidt et al, J. Antibiotics, 41, 1988, 780).

UK Patent 1 593 524, Merck & Co. disclose a number of 5-membered heteroaromatic carbapenem derivatives including diazolyl and tetrazolyl compounds. However, in the case of the pyrazolyl derivatives the heterocyclic compound is attached to the carbapenem nucleus through the C-4 position.

Other structural modifications introduced at position-2 include a substituted vinyl group —C($R_a$)=CH$R_b$, in which, for instance, $R_a$ is hydrogen or methyl and $R_b$ is hydrogen or lower alkyl (EP 0 330 108; Fujisawa) or $R_a$ and $R_b$ are selected from hydrogen, lower alkyl, aminocarbonyl, lower alkoxy, cyano, nitro and lower alkoxycarbonyl (EP 0 430 037, Banyu Pharmaceutical Co.). In the absence of a 1β-methyl substitutent, such a modification does not however appear to impart DHP-1 stability.

We have surprisingly found that other types of structural modification at position-2 are advantageous.

Accordingly the present invention provides a compound of the general formula (I):

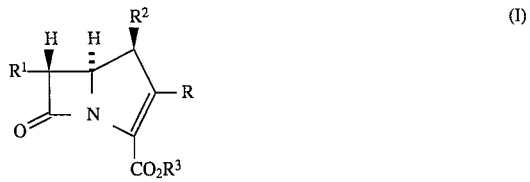

in which R is:

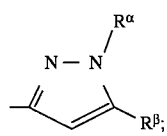

wherein $R^\alpha$ is hydrogen, optionally substituted $(C_{1-6})$alkyl or optionally substituted aryl;

$R^\beta$ is hydrogen, optionally substituted $(C_{1-6})$alkyl or optionally substituted aryl; or $R^\alpha$ and $R^\beta$ together form an optionally substituted 5 or 6 membered heterocyclic ring with or without additional heteroatoms;

$R^1$ is $(C_{1-6})$alkyl which is unsubstituted or substituted by fluoro, a hydroxy group which is optionally protected by a readily removable hydroxy protecting group, or by an amino group which is optionally protected by a readily removable amino protecting group;

$R^2$ is hydrogen or methyl;

—$CO_2R^3$ is carboxy or a carboxylate anion or the group $R^3$ is a readily removable carboxy protecting group.

Compounds of formula (I) have a broad spectrum of anti-bacterial activity, and show good stability towards DHP-1.

Suitable $(C_{1-6})$ alkyl groups for $R^\alpha$ and $R^\beta$ include straight and branched chain alkyl groups having from 1 to 6 carbon atoms, for instance methyl, ethyl, n-propyl and iso-propyl, preferably ethyl and methyl.

Representative examples of $R^\alpha$ and $R^\beta$ being $(C_{1-6})$alkyl are when both are methyl or ethyl. A particularly preferred example is when $R^{60}$ is ethyl and $R^\beta$ is methyl.

Optional substituents suitable for the $(C_{1-6})$alkyl group for $R^{60}$ and $R^{62}$ include, for example, halogen, hydroxy, $(C_{1-6})$alkoxy, carboxy and salt thereof, $(C_{1-6})$alkoxycarbonyl, carbamoyl, mono- or di($C_{1-6}$)alk-ylcarbamoyl, sulphamoyl, mono- and di($C_{1-6}$)alkylsulphamoyl, amino, mono- and di($C_{1-6}$)alkylamino, $(C_{1-6})$acylamino, ureido, $(C_{1-6})$alkoxycarbonylamino, aminocarbonyloxy and mono- and di($C_{1-6}$)alkylaminocarbonyloxy, 2,2,2-trichloroethoxycarbonylamino, aryl, heterocyclyl, oxo, acyl, heteroaryl, $(C_{1-6})$alkylthio, arylthio, heterocyclythio, $(C_{1-6})$alkane-sulphinyl, arylsulphinyl, $(C_{1-6})$alkanesulphonyl, arylsulphonyl, $(C_{1-6})$alkoxyimino, hydroxyimino, hydrazono, benzohydroxyimoyl, and 2-thiophenecarbohydroxyimoyl. Preferred substiments include carbamoyl, aryl, especially phenyl, and heteroaryl.

Suitable $(C_{1-6})$ alkyl groups for $R^1$ include straight and branched chain alkyl groups having from 1 to 6 carbon atoms. Preferred alkyl groups include methyl, ethyl, iso-propyl, of which ethyl is especially preferred.

Preferably the $(C_{1-6})$ alkyl group of $R^1$ has a hydroxy, fluoro or amino substituent which is suitably at position-1 of the alkyl group. Advantageously $R^1$ is (R)-1-hydroxyethyl.

Suitably $R^2$ is hydrogen.

When used herein, the term "aryl" includes phenyl and naphthyl.

Suitably an aryl group, including phenyl and naphthyl, may be optionally substituted by up to five, preferably up to three, substituents.

A representative example of $R^\alpha$ or $R^\beta$ being an aryl group is phenyl.

Optional substituents suitable for the aryl group include halogen, $(C_{1-6})$alkyl, aryl$(C_{1-4})$alkyl, $(C_{1-6})$alkoxy, $(C_{1-6})$alkoxy$(C_{1-6})$alkyl, halo$(C_{1-6})$alkyl, hydroxy, amino, mono- and di-N-$(C_{1-6})$alkylamino, acylamino, carboxy, carboxy salts, carboxy esters, carbamoyl, mono- and di-N-$(C_{1-6})$alkylcarbamoyl, $(C_{1-6})$alkoxycarbonyl, $(C_{1-6})$alkoxycarboxylate, aryloxycarbonyl, $(C_{1-6})$alkoxycarbonyl- $(C_{1-6})$alkyl aryl, oxy groups, ureido, guanidino, sulphonylamino, aminosulphonyl, $(C_{1-6})$alkylthio, $(C_{1-6})$alkyl sulphinyl $(C_{1-6})$alkylsulphonyl, heterocyclyl and heterocyclyl $(C_{1-4})$alkyl. In addition, two adjacent ring carbon atoms may be linked by a $(C_{3-5})$alkylene chain, to form a carbocyclic ring.

When used herein, the term "heteroatom" includes one or more of the elements oxygen, nitrogen and sulphur.

When used herein, the term "heteroaryl" includes aromatic single and fused rings containing up to tour heteroatoms in each ring, each of which is selected from oxygen, nitrogen and sulphur, which rings may be unsubstituted or substituted by, for example, up to three substituents. Each heteroaryl ring suitably has 5 or 6 ring atoms. A fused heteroaryl ring may include carbocyclic rings and need include only one heteroaryl ring.

When used herein, the terms "heterocyclyl" and "heterocyclic" suitably include, unless otherwise defined, aromatic and non-aromatic, single and fused, rings suitably containing up to four heteroatoms in each ring, each of which is selected from oxygen, nitrogen and sulphur, which rings, may be unsubstituted or substituted by, for example, up to three substituents. Each heterocyclic ring suitably has from 4 to 7, preferably 5 or 6, ring atoms. A fused heterocyclic ring system may include carbocyclic rings and need include only one heterocyclic ring.

Preferably a substituent for a heteroaryl or a heterocyclyl group is selected from halogen, $(C_{1-6})$allkyl, aryl$(C_{1-4})$alkyl$(C_{1-6})$alkyl, $(C_{1-6})$alkoxy$(C_{1-6})$alkyl, halo$(C_{1-6})$alkyl, hydroxy, amino, mono- and di-N-$(C_{1-6})$alkyl-amino, acylamino, carboxy salts, carboxy esters, carbamoyl, mono- and di-N-$(C_{1-6})$alkylcarbonyl, $(C_{1-6})$alkoxycarboxylate, aryloxycarbonyl, $(C_{1-6})$alkoxycarbonyl$(C_{1-6})$alkyl, aryl, oxy groups, ureido, guanidino, sulphonylamino, aminosulphonyl, $(C_{1-6})$alkylthio, $(C_{1-6})$alkylsulphinyl, $(C_{1-6})$alkylsulphonyl, heterocyclyl and heterocyclyl$(C_{1-4})$alkyl.

Suitable hydroxy and amino protecting groups for use in $R^1$ are those well known in the art and which may be removed under conventional conditions and without disrupting the remainder of the molecule. A comprehensive discussion of the ways in which hydroxy and amino groups may be protected and methods for cleaving the resulting protected derivatives is given in for example "Protective Groups in Organic Chemistry." (T. W. Greene, Wiley-Interscience, New York. 2nd edition, 1991). Particularly suitable hydroxy protecting groups include, for example, triorganosilyl groups such as, for instance, trialkylsilyl and also organooxycarbonyl groups such, as for instance, allyloxycarbonyl, trichloroethyloxycarbonyl, 4-methoxybenzyloxycarbonyl and 4-nitrobenzyloxycarbonyl. Particularly suitable amino protecting groups include alkoxycarbonyl, 4-methoxybenzyloxycarbonyl and 4-nitrobenzyloxycarbonyl.

Since the carbapenem compounds of the present invention are intended for use in pharmaceutical compositions, it will be readily appreciated that preferred compounds within formula (I) are pharmaceutically acceptable i.e. are compounds of formula (Ia):

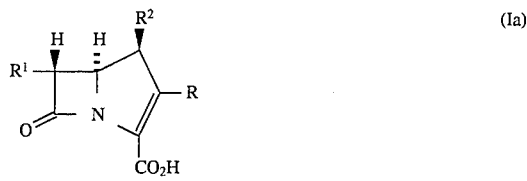

in which R, $R^1$ and $R^2$ are as hereinbefore defined or pharmaceutically acceptable salts or pharmaceutically acceptable in vivo hydrolysable esters thereof.

Non-pharmaceutically acceptable salts of the compound of formula (I) in which $R^3$ is hydrogen are primarily of use as intermediates in the preparation of compounds of formula (I) in which $R^3$ is hydrogen or a pharmaceutically acceptable salt thereof. Salts within compounds of formula (I) may be prepared by salt exchange in a conventional manner.

Similarly, carboxy-protected derivatives of formula (I) i.e. those compounds of formula (I) in which $R^3$ is a readily removable carboxy protecting group, may be used in the preparation of a compound of formula (I) in which $R^3$ is hydrogen or a pharmaceutically acceptable salt thereof. Included within the scope of readily removable carboxy protecting groups for $R^3$ are ester groups including pharmaceutically acceptable in vivo hydrolysable ester groups.

Suitable readily removable carboxy protecting groups for the group —$CO_2R^3$ include groups forming ester derivatives of the carboxylic acid, including in vivo hydrolysable esters. The derivative is preferably one which may readily be cleaved.

Suitable ester-forming carboxy-protecting groups are those which may be removed under conventional conditions. Such groups for $R^3$ include benzyl, 4-methoxybenzyl, benzoylmethyl, 4-nitrobenzyl, 4-pyridylmethyl, 2,2,2-trichloroethyl, 2,2,2-tribromoethyl, t-butyl, t-amyl, allyl, diphenylmethyl, triphenylmethyl, adamantyl, 2-benzyloxyphenyl, 4-methylthiophenyl, tetrahydrofuran-2-yl, tetrahydropyran-2-yl, pentachlorophenyl, acetonyl, p-toluenesulphonylethyl, methoxymethyl, a silyl, stannyl or phosphorus-containing group, an oxime radical of the formula —N=CHR$^x$ where $R^x$ is aryl or heterocyclic, or an in vivo hydrolysable ester radical such as defined below.

A carboxy group may be regenerated from any of the above esters by the usual methods appropriate to the particular $R^3$ group, for example, acid- and base-catalvsed hydrolysis, enzymically-catalysed hydrolysis or photochemical methods, under conditions wherein the remainder of the molecule is substantially unaffected.

Preferably the ester-forming carboxy-protecting group is 4-methoxybenzyl, which may be suitably be removed using aluminium chloride and anisole; 4-nitrobenzyl which may be suitably removed using iron powder and ammonium chloride (1M soln) or by hydrogenation using palladium on a carbon catyalyst or zinc dust and phosphate buffer solution as described in *Heterocycles*, 1993, 36(2), 1727; or allyl which may be suitably removed using tetrakis(triphenylphosphine)palladium and triphenylphosphine.

Advantageously, the hydroxy, amino and carboxy-protecting groups, when used, are selected so that they can be removed under the same conditions, in a single reaction step; for example allyloxycarbonyl (for hydroxy) and allyl (for carboxy) which may be both removed using tetrakis(triphenylphosphine)palladium and triphenylphosphine. Another suitable combination is trialkylsilyl (for hydroxy) and 4-methoxybenzyl (for carboxy) which may both be removed using aluminium chloride and anisole.

Examples of suitable pharmaceutically acceptable in vivo hydrolysable ester groups include those which break down readily in the human body to leave the parent acid or its salt. Suitable ester groups of this type include those of part formula (a), (b), (c) and (d):

—CO₂CH(Rᵃ)O.CO.Rᵇ (a)

—CO₂RᶜNRᵈRᵉ (b)

—CO₂CH₂ORᶠ (c)

—CO₂CH(Rᵃ)O.CO.C₆H₄YCOCH(Rᵍ)NH₂ (d)

in which:

$R^a$ is hydrogen, $(C_{1-6})$alkyl, $(C_{3-7})$cycloalkyl, methyl, or phenyl;

$R^b$ is $(C_{1-6})$alkyl, $(C_{1-6})$alkoxy, $(C_{3-7})$cycloalkyloxy, phenyl, benzyl, $(C_{3-7})$cycloalkyl, $(C_{1-6})$alkyl$(C_{3-7})$cycloalkyl, 1-amino$(C_{1-6})$alkyl, or 1-$(C_{1-6}$alkyl)amino$(C_{1-6})$alkyl: or $R^a$ and $R^b$ together form a 1,2-phenylene group optionally substituted by one or two methoxy groups;

$R^c$ is $(C_{1-6})$alkylene optionally substituted with a methyl or ethyl group;

$R^d$ and $R^e$ which may be the same or different is each $(C_{1-6})$alkyl;

$R^f$ is $(C_{1-6})$alkyl;

$R^g$ is hydrogen or phenyl optionally substituted by up to three groups selected from halogen, $(C_{1-6})$-alkyl, or $(C_{1-6})$alkoxy; and Y is oxygen or NH.

Examples of suitable pharmaceutically acceptable in vivo hydrolysable ester groups include, for example, acyloxyalkyl groups such as acetoxymethyl, pivaloyloxymethyl, α-acetoxyethyl, α-pivaloyloxyethyl, 1-(cyclohexyloxycarbonyloxy)ethyl, and (1-aminoethyl)-carbonyloxymethyl; alkoxycarbonyloxyalkyl groups, such as ethoxycarbonyloxymethyl and α-ethoxycarbonyloxyethyl; cycloalkoxycarbonyloxyalkyl groups, such as cyclohexyloxycarbonyloxymethyl (hexmetil) and 1-(cyclohexyloxycarbonyloxy)ethyl (hexetil); dialkylaminoalky especially di-loweralkylamino alkyl groups such as dimethylaminomethyl, dimethylaminoethyl, diethylaminomethyl or diethylaminoethyl; lactone groups such as phthalidyl and dimethoxyphthalidyl; and esters linked to a second β-lactam antibiotic or to a β-lactamase inhibitor.

A further suitable pharmaceutically acceptable in vivo hydrolysable ester group is that of the formula:

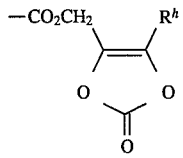

in which $R^h$ is hydrogen, $(C_{1-6})$alkyl or phenyl.

Suitable pharmaceutically acceptable salts of the carboxy group of the compound of formula (I) include metal salts, for example aluminium, alkali metal salts such as sodium or potassium, alkaline earth metal salts such as calcium or magnesium; and ammonium or substituted ammonium salts, for example those with lower alkylamines such as triethylamine, hydroxy-lower alkylamines such as 2-hydroxyethylamine, bis-(2-hydroxyethyl)-amine or tris-(2-hydroxyethyl)-amine, cycloalkylamines such as dicyclohexylamine, or with procaine, dibenzylamine, N,N-dibenzylethylenediamine, 1-ephenamine, N-methylmorpholine, N-ethylpiperidine, N-benzyl-b-phenethylamine, dehydroabietylamine, N,N'-bis-dehydro-abietylamine, ethylenediamine or N-methylglucosamine; or basic amino acids such as lysine, arginine, or bases of the pyridine type such as pyridine, collidine or quinoline; or other amines which have been used to form salts with known penicillins and cephalosporins. Other useful salts include the lithium salt and silver salt.

Since the carbapenem compounds of the present invention are intended for use in pharmaceutical compositions, it will be further understood that they are each provided in substantially pure form, for example at least 50% pure, more suitably at least 75% pure and preferably at least 95% pure (% are on a wt/wt basis). Impure preparations of the compounds may be used for preparing the more pure forms used in the pharmaceutical compositions. Although the purity of intermediate compounds of the present invention is less critical, it will readily be understood that the substantially pure form is preferred as for the carbapenem compounds. Preferably, whenever possible, the compounds of the present invention are obtained in crystalline form When some of the compounds of this invention are allowed to crystallise or are recrystallised from organic solvents, solvent of crystallisation may be present in the crystalline product. This invention includes within its scope such solvates. Similarly, some of the compounds of this invention may be crystallised or recrystallised from solvents containing water. In such cases water of hydration may be present in the crystalline product. This invention includes within its scope stoichiometric hydrates as well as compounds containing variable amounts of water that may be produced by processes such as lyophilisation.

A specific compound within this invention include the following and pharmaceutically acceptable salts and in vivo hydrolysable esters thereof:

(5R,6S)-6-[(R)-1-hydroxyethyl]-2-(1,5-dimethylpyrazol-3-yl)-carbapen-2-em-3-carboxyl acid, (5R,6S)-6-[(1R)-hydroxyethyl]-2-(1-phenylpyrazol-3-yl)-carbapen-2-em-3-carboxylic acid.

(5R,6S)-6-[(1R)-hydroxyethyl]-2-(1-methylpyrazol-3-yl)-carbapen-2-em-3-carboxylic acid, (5R,6S)-6-[(R)-1-hydroxyethyl]-2-(5-methyl-1-phenethylpyrazol-3-yl)carbapen-2-em-3-carboxylic acid, (5R,6S)-6-[(R)-1-hydroxyethyl)]-2-[1-(2-phenethyl)pyrazol-3-yl]-carbapen-2-em-3-carboxylic acid, (5R,6S)-6-[(R)-1-hydroxyethyl]-2-[4,5,6,7-tetrahydropyridino-(1,2-b)-pyrazol-2-yl]carbapen-2-em-3-carboxylic acid, (5R,6S)-6[(1R)-1-hydroxyethyl]-2-(5-methyl-1-phenylpyrazol-3-yl)carbapen-2-em-3-carboxylic acid, (5R,6S)-2-[5,6-Dihydro-4H-pyrrolo(1,2-b)-pyrazol-2-yl]-6-[(R)-1-hydroxyethyl]carbapen-2-em-3-carboxylic acid, (5R,6S)-6-[(R)-1-hydroxyethyl]-2-(1,5-diethylpyrazol-3-yl)carbapen-2-em-3-carboxylic acid, (5R,6S)-6-[(R)-1-hydroxyethyl]-2-(1-ethyl-5-methylpyrazol-3-yl)carbapen-2-em-3-carboxylic acid, (5R,6S)-6-[(R)-1-hydroxyethyl]-2-[1-(2-hydroxyethyl)-5-methylpyrazol-3-yl]carbapen-2-em-3-carboxylic acid, (5R,6S)-6-[(R)-1-hydroxyethyl]-2-[1-(2-methoxyethyl)-5-methylpyrazol-3-yl]}carbapen-2-em-3-carboxylic acid, (5R,6S)-6-[(R)-1-hydroxyethyl]-2-(5-benzyl-1-methylpyrazol-3-yl)carbapen-2-em-3-carboxylic acid, (5R,6S)-6-[(R)-1-hydroxyethyl]-2-{5-methyl-1-[2-(1-methyl-tetrazol-5-ylthio)ethyl]pyrazol-3-yl}carbapen-2-em-3-carboxylic acid, (5R,6S)-2-[1-(2-acetamidoethyl)-5-methylpyrazol-3-yl]-6-[(1R)-1-hydroxyethyl]carbapen-2-en-3-carboxylic acid, (5R,6S)-2-[1-(2-methylthioethyl)-5-methylpyrazol-3-yl]-6-[(1R)-1-hydroxyethyl]carbapen-2-em-3-carboxylic acid, (5R,6S)-6-[(1R)-1-Hydroxyethyl]-2-(1-methyl-5-ethylpyrazol-3-yl)carbapen-2-em-3-carboxylic acid, (5R,6S)-6-[(1R)-1-hydroxyethyl]-2-[5-methyl-1-(2-methylsulphonylethyl)pyrazol-3-yl]-carbapen-2-em-3-carboxylic acid and (5R,6S)-2-[1-[2-(N,N-dimethylaminocarbonyloxy)ethyl]-5-methylpyrazol-3-yl]-6-[(1R)-1-hydroxyethyl]carbapen-2-em-3-carboxylic acid.

The carbapenem antibiotic compounds according to the invention may be formulated for administration in any convenient way for use in human or veterinary medicine, according to techniques and procedures per se known in the art with reference to other antibiotics, and the invention therefore includes within its scope a pharmaceutical composition comprising an antibiotic compound according to the present invention such as, for example, a compound of formula (Ia) or a pharmaceutically acceptable salt or in vivo hydrolysable ester thereof, together with a pharmaceutically acceptable carrier or excipient. The compositions may be formulated for administration by any suitable route, such as oral, parenteral or topical application. The compositions may be in the form of tablets, capsules, powders, granules, lozenges, creams or liquid preparations, such as oral or sterile parenteral solutions or suspensions. Tablets and capsules for oral administration may be in unit dose presentation form and may contain conventional excipients such as binding agents, for example, syrup acacia, gelatin, sorbitol, tragacanth, or polyvinylpyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, methyl cellulose, glucose syrup, gelatin, hydroxyethyl cellulose, carboxymethyl cellulose, aluminium stearate gel or hydrogenareal edible fats; emulsifying agents, for example lecithin, sorbitan monooleate, or acacia; non-aqueous vehicles (which may include edible oils), for example almond oil, oily esters, glycerine, propylene glycol, or ethyl alcohol; preservatives, for example methyl or propyl p-hydroxybenzoate or sorbic acid; and, if desired conventional flavouring or colouring agents. Suppositories will contain conventional suppository base, eg cocoa-butter or other glyceride.

For parenteral administration, fluid unit dosage forms are prepared utilising the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing. Advantageously, agents such as local anaesthetic, preservative and buffering agents can be dissolved in the vehicle. To enhance the stability, the composition can be frozen after filling into the vial and the water removed under vacuum. The dry lyophilised powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

The composition may contain from 0.1% to 99.5% by weight, preferably, from 10–60% by weight, of the active material, depending on the method of administration. Where the compositions comprise dosage units, each unit will preferably contain from 50–500 mg of the active ingredient. The dosage as employed for adult human treatment will preferably range from 100 mg to 12 g per day for an average adult patient (body weight 70 kg), for instance 1500 mg per day, depending on the route and frequency of administration. Such dosages correspond to approximately 1.5 to 170 mg/kg per day. Suitably the dosage is from 1 to 6 g per day.

The daily dosage is suitably given by administering a compound of the invention several times in a 24-hour period. Typically, 250 mg is administered 4 times a day although, in practice, the dosage and frequency of administration which will be most suitable for an individual patient will vary with the age, weight and response of the patients, and there will be occasions when the physician will choose a higher or lower dosage and a different frequency of administration. Such dosage regimens are within the scope of this invention.

No toxicological effects are indicated when a compound of the invention of formula (Ia) or a pharmaceutically acceptable salt or in vivo hydrolysable ester thereof is administered in the above mentioned dosage range.

The present invention also includes a method of treating bacterial infections in humans and animals which method comprises administer a therapeutically effective amount of an antibiotic compound of the present invention of the formula (Ia) or a pharmaceutically acceptable salt or in vivo hydrolysable ester thereof.

In a further aspect, the present invention also provides for the use of a compound of formula (Ia) or a pharmaceutically acceptable salt or an in vivo hydrolysable ester thereof for the manufacture of a medicament for treating bacterial infection.

The compounds of the present invention of formula (Ia) or pharmaceutically acceptable salts or in vivo hydrolysable esters thereof are active against a broad range of Gram-positive and Gram-negative bacteria, and may be used to treat a wide range of bacterial infections including those in immunocompromised patients.

Amongst many other uses, the compounds of the invention of formula (Ia) or salts or pharmaceutically acceptable in vivo hydrolysable esters thereof are of value in the treatment of skin, soft tissue, respiratory tract and urinary tract infections in humans and may also be used to treat mastiris in cattle.

A particular advantage of the antibacterially active compounds of this invention is their stability to β-lactamase enzymes and they are therefore effective against β-lactamase producing organisms.

The present invention further provides a process for the preparation of a compound of formula (I) which process comprises treating a compound of formula (II):

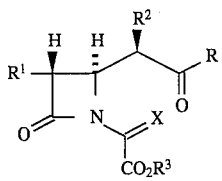
(II)

in which R, $R^1$ and $R^2$ are as hereinbefore defined,
$R^3$ is a readily removable carboxy protecting group,
X is oxygen or a group $PR^4R^5R^6$,
$R^4$, $R^5$ and $R^6$ which may be the same or different and is each an optionally substituted $(C_{1-6})$alkyl or an optionally substituted aryl group, preferably an n-butyl or a phenyl group;
under carbapenem ring forming conditions;
and thereafter, and if necessary, carrying out any or all of the following steps:
  removing any protecting group(s);
  converting a first group $R^1$ comprising a hydroxyl substiment into a further group $R^1$ comprising an amino or fluoro group; and/or
  converting the product into a salt.

Suitable carbapenem ring forming conditions are well known in the art.

When X is oxygen, suitable ring forming conditions include treating the compound of formula (II) with a trivalent organic phosphorus compound of formula (III):

$$PR^7(OR^8)(OR^9) \qquad (III)$$

in which:
$R^7$ is $(C_{1-4})$alkyl, $(C_{1-3})$alkoxy or phenyl optionally substituted by $(C_{1-3})$alkyl; and
$R^8$ and $R^9$ which may be the same or different is each $(C_{1-4})$alkyl, allyl, benzyl or phenyl optionally substiment by $(C_{1-3})$alkyl or $(C_{1-3})$alkoxy; by analogy with the process described in EP 0 476 649-A (Hoechst AG). Suitable reagents of formula (III) include trimethyl phosphite, triethyl phosphite, dimethyl methylphosphonite and diethyl methylphosphonite. Suitably, the reaction is effected in an organic solvent such as tetrahydrofuran, ethyl acetate, an aromatic solvent such as benzene, toluene, xylene or mesitylene or a halogenated hydrocarbon solvent such as dichloromethane, trichloromethane or 1,1,2-trichloroethane, and at a temperature between 50° and 180° C., preferably between 70° and 165° C.

When X is a group $PR^4R^5R^6$, compounds of formula (I) may be obtained by the well known Wittig cyclisation route to carbapenems (Guthikonda et al. J. Med. Chem., 1987, 30, 871). For instance, when $R^4$, $R^5$ and $R^6$ is each phenyl, the process comprises the ring closing elimination of the elements of triphenylphosphine oxide. The ring closure may be suitably effected by heating the compound of formula (II, X=$PR^4R^5R^6$) at a temperature which is preferably in the range 40° to 145° C., more preferably 80° to 140° C., in an inert solvent such as benzene, toluene or xylene, preferably under dry conditions and under an inert atmosphere and optionally in the presence of a radical scavenger such as hydroquinone. When $R^4$, $R^5$ and $R^6$ is each n-butyl, cyclisation may be effected at a lower temperature, for instance above 50° C., by analogy with the process described in WO 92/01695 (Beecham Group, for analogous penems).

In the substituent $R^1$, a hydroxyl or an amino group, if present, may optionally be protected. Suitable hydroxy protecting groups include organosilyl, for instance a trialkylsilyl group such as trimethylsilyl or t-butyl dimethylsilyl, or trichloroethyloxycarbonyl, 4-nitrobenzyloxy-carbonyl, 4-methoxybenzyloxy carbonyl and allyloxycarbonyl. Suitable amino protecting groups include alloxycarbonyl, 4-methoxybenzyloxy carbonyl and 4-nitrobenzyloxycarbonyl.

Suitable values for the protecting group $R^3$ include allyl, 4-methoxybenzyl and 4-nitrobenzyl. The conditions necessary for removing the protecting group will, of course, depend upon the precise nature of the protecting group. For instance, when of $R^3$ is 4-methoxybenzyl, aluminium trichloride and anisole in dichloromethane at −30° to −70° C. may be used, when $R^3$ is allyl (prop-2-en-1-yl), a combination of triphenylphosphine, sodium-2-ethylhexanoate in ethyl acetate/MDC and tetrakis-(triphenylphosphine)palladium (0) may be used and when R3 is p-nitrobenzyl hydrogenation in the presence of palladium on a carbon catalyst in aqueous solvent eg, aqueous 1,4,dioxan THF ethanol may be used.

Compounds of formula (II) are novel compounds and useful as intermediates in the preparation of compounds of formula (I).

Accordingly, in a further aspect, the present invention provides a compound of formula (II), as hereinbefore defined.

Compounds of formula (II) in which X is oxygen may be obtained by a process which comprises reacting a compound of formula (IV):

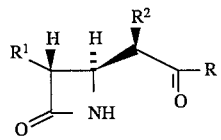
(IV)

in which R, $R^1$ and $R^2$ are as hereinbefore defined, with a compound of formula (V):

$$ClCOCO_2R^3 \qquad (V)$$

in which $R^3$ is a readily removable carboxy protecting group; under acylating conditions, by analogy with the process described in Tetrahedron Letters. 25, 1984. 2395.

Compounds of formula (IV) are novel compounds and useful as intermediates in the preparation of compounds of formula (II).

Accordingly, in a further aspect, the present invention provides a compound of formula (IV), as hereinbefore defined.

Compounds of formula (II) in which X is a group $PR^4R^5R^6$ may be obtained from a compound of formula (IV) as hereinbefore defined by the following sequence of steps:

(a) reacting with a suitably protected glyoxylic acid derivative of formula (VI) or a functional equivalent thereof such as the hydrate;

$$(OHC)CO_2R^3 \qquad (VI)$$

in which $R^3$ is a readily removable carboxy protecting group; under dehydrating conditions, for instance azeotropic removal of water;

(b) treating the intermediate formed in step (a) with a halogenating agent, for instance thionyl chloride, in the presence of a suitable base such as 2,6-lutidine; and (c) treating the intermediate formed in step (b) with a phosphorus reagent of the formula (VII):

PR⁴R⁵R⁶  (VII)

in which R⁴, R⁵ and R⁶ are as hereinbefore defined, in the presence of a suitable base such as 2,6-lutidine.

Compounds of formula (IV) may be prepared by treating a compound of formula (VIII):

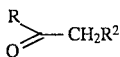
(VIII)

in which R and R² are as hereinbefore defined; with a compound of formula (IX)

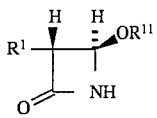
(IX)

in which R¹ is as hereinbefore defined, and

R¹¹ is an acyl group, for instance acetyl;

in the presence of a base, such as, for instance, lithium hexamethyldisilazide (LHMDS);

according to the procedures described in Tetrahedron Lett., 1987, 28, 507, and Can. J. Chem. 1988, 66, 1537.

Compounds of formula (IV) may also be prepared by treating a compound of formula (VIIIa):

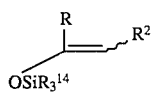
(VIIIa)

in which R and R² are as hereinbefore defined and SiR₃¹⁴ is a trialkylsilyl such as trimethylsilyl or t-butyldimethylsilyl, with a compound of formula (IXa):

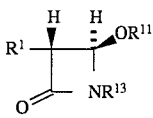
(IXa)

in which R¹ and R¹¹ are as hereinbefore defined and

R¹³ is either hydrogen or an aminoprotecting group, for instance, a trialkylsilyl group such as trimethylsilyl;

in the presence of a Lewis acid, such as, for instance, zinc chloride or trimethylsilyl trifluoromethane sulphonate, in an inert organic solvent such a halogenated hydrocarbon solvent, for instance dichloromethane at ambient temperature: Compounds of formula (VIIIa) may be prepared by treating compounds of formula (VIII) with trialkylsilyl chloride or trialk-ylsilyl triflate, and triethylamine in MDC.

If the aminoprotecting group R¹³ in (IXa) requires subsequent removal, this may be achieved by conventional means, such as mild acid treatment eg, methanol and hydrochloric acid or pyridinium p-toluenesulphonate, where R¹³ is trimethylsilyl.

Compounds of formula (VIII) are well known to those skilled in the art and may be obtained by standard synthetic procedures as described in the following Example.

Compounds of formula (IX) are well known to those skilled in the an and may be obtained by standard synthetic procedures such as described in, for example, Het., 1982, 17, 201 (IX, R¹ is 1-hydroxyethyl) and EP 0 234 484 (IX, R¹ is 1-fluoroethyl).

Compounds of formula (I) in which R¹ is an amino-substituted alkyl or cycloalkyl may be conveniently prepared from a corresponding compound of formula (I) in which R¹ includes a hydroxy group by a Mitsunobu-type azide displacement of the hydroxy group thereof, followed by catalytic reduction, according to the procedure described in J Chem Soc, Perkin I, 1982, 3011.

Compounds of formula (I) may also be prepared by a process which comprises reacting a compound of formula (X):

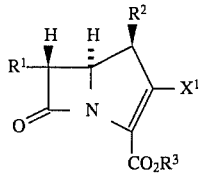
(X)

in which R¹ and R² are as hereinbefore defined, R³ is a readily removable carboxy protecting group and X¹ is a leaving group, with a compound of formula (XI):

M—R  (XI)

in which M is a metallo group and R is as hereinbefore defined; in a cross-coupling reaction in the presence of a cross-coupling reaction catalyst selected according to the identity of M and thereafter and if necessary removing any protecting group and/or converting the product into a salt.

Suitable values for the protecting group R³ include 4-methoxybenzyl 4-nitrobenzyl.

Examples of suitable leaving groups X¹ include for instance trifluoromethanesulphonyloxy, methanesulphonyloxy, 4-toluene sulphonyloxy, fluorosulphonyloxy, chloro, bromo, iodo and diphenoxyphosphoryloxy.

Suitable metals for use in the metallo group M are well known in the art and include tin, aluminium, zinc, boron, mercury and zirconium.

Preferred examples of the metallo group M include for instance R¹⁴R¹⁵R¹⁶Sn, B(OR)₂ and ZnCl in which R¹⁴, R¹⁵ and R¹⁶ may the same or different and are each (C₁₋₆) alkyl. Preferably, the metallo group M is an organostannane R¹⁴R¹⁵R¹⁶Sn, and R¹⁴=R¹⁵=R¹⁶=methyl or n-butyl.

Suitable cross-coupling catalysts are well known in the an and include palladium compounds, in particular palladium (0) and palladium (II) compounds, such as those described in "Palladium Reagents in Organic Synthesis", R. F. Heck, Academic Press Ltd. 1985. Examples thereof include tris-(dibenzylideneacetone )dipalladium (0), tetrakis(triphenylphosphine)palladium (0), trans dimethyl bis(triphenylphosphine)palladium (II), and palladium (II) acetate, benzyl bis(triphenylphosphine)palladium (II) chloride, bis-(triphenylphosphine)palladium (II) dichloride. Such palladium reagents are preferably used in combination with a halide source such as zinc chloride or lithum chloride and optionally in the presence of a phosphine ligand of palladium, for instance a compound such as a triarylphosphine, for example, tris(4-methoxyphenyl)phosphine or tris(2,4,6-trimethoxyphenyl)phosphine; a triheteroarylphosphine, for example, trifurylphosphine, or a triarylarsine, for example triphenylarsine.

When M is an organostannane R¹⁴R¹⁵R¹⁶Sn—, a preferred catalyst system is tris(dibenzylideneacetone)dipalladium (0), in the presence of zinc chloride and a phosphine compound. When M is ZnCl a preferred catalyst is tris(dibenzylideneacetone dipalladium (0), in the presence of a phosphine compound.

Suitably the reaction is effected in an inert aprotic polar coordinating solvent such as tetrahydrofuran, diethylether, dioxane, 2-dimethoxyethane, acetonitrile, dimethyl formamide, dimethyl sulphoxide and the like, and under a dry, inert atmosphere such as argon. Suitably, the reaction is effected initially at a low temperature, for instance about −78° C., with the final phase of the reaction then being effected at ambient temperature.

Analogous procedures in which M is organostannane are described in EP 0 444 889 (Merck & Co.) and EP 0 430 037 (Banyu Pharmaceutical Co.).

Compounds of formula (X) are well known in the art and may be obtained according to the procedures described in EP 0 444 889 (Merck & Co.), EP 0 430 037 (Banyu Pharmaceutical Co.) and by Rano et al, Tet. Letters, 1990, 31, 2853.

Compounds of formula (XI) are well known in the art and may be obtained according to the procedure described in Heterocycles, 1992, 33(2), 813.

The following examples illustrate the invention but are not intended to limit the scope in any way.

General Instructions—Solutions were dried using anhydrous magnesium sulphate and solvents were removed by evaporation under reduced pressure using a rotary evaporator. Column chromatography on silica gel used Merck silica gel 60, particle size <0.063 mm.

EXAMPLE 1

Sodium (5R,6S)-6-[(R)-1-hydroxyethyl]-2-(1,5-dimethylpyrazol-3-yl)-carbapen-2-em-3-carboxylate

Preparation 1

Ethyl-1,5-dimethylpyrazole-3-carboxylate

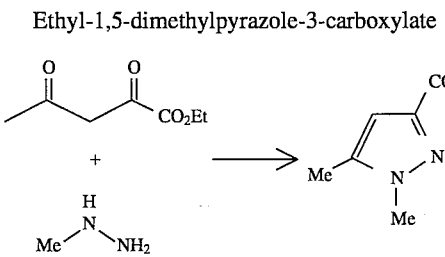

Ethyl 2,4-dioxovalerate (5.6 ml, 40 mM) was dissolved in glacial acetic acid (35 ml) before cooling the reaction temperature to 8°–10° C. Methylhydrazine (2.0 ml, 38 mM) was added dropwise so that the reaction temperature did not rise above 15° C. After stirring at room temperature for 90 minutes the reaction was poured into ethyl acetate and water. The organic phase was washed with saturated sodium bicarbonate solution, water and brine before drying (MgSO$_4$). Purification was accomplished was by chromatography on silica gel (10×4.5 cm) loading in dichloromethane and eluting with 50% ethyl acetate in hexane. Evaporation of solvent gave the title compound as a coloured oil which crystallised on standing (4.69 g); $v_{max}$ (CH$_2$Cl$_2$) 1717 and 1223 cm$^{-1}$; $\delta_H$ (CDCl$_3$) 1.39 (3H, t, J 7.13 Hz), 2.30 (3H, s), 3.85 (3H, s), 4.39 (2H, q, J 7.21 Hz), 6.57 (1H, s); E.I m/e 168 (25% ).

Preparation 2

3-Acetyl-1,5-Dimethylpyrazole

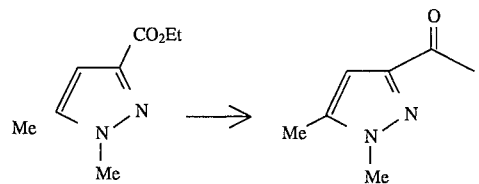

Ethyl 1,5-dimethylpyrazole-3-carboxylate (3.59 g, 21.4 mM) was dissolved in dry, tetrahydrofuran (70 ml) and cooled to −100° C. whilst under an atmosphere of argon. Trimethylsilylchloride (13.5 ml, 107 mM) was added by rapid dropwise addition. Immediately after methyllithium (77.7 ml of 1.1M solution in diethylether. 85.5 mM) was added dropwise in such a way that the internal temperature never exceeded −85° C. After complete addition the heterogeneous reaction was allowed to warm to room temperature. Most of the solvent was removed by evaporation in vacuo before treating with ethanol (6 ml) followed by water (6 ml). After vigorously stirring for 5 minutes the mixture was diluted with ethyl acetate and water. The pH was adjusted to 7 by treating with saturated sodium bicarbonate Solution. The organic phase was separated and washed with brine before drying (MgSO$_4$). Purification was accomplished by chromatography on silica gel (12×4.25 cm) loading in dichloromethane and eluting with 40% ethylacetate in hexane followed by 60% ethyl acetate in hexane. Removal of the solvents gave the title compound as a coloured oil which solidified on standing at room temperature (1.42 g) $v_{max}$ (CH$_2$Cl$_2$) 1679, 1551, 1448, and 1373 cm$^{-1}$; $\delta_H$ (CDCl$_3$) 2.30 (3H, s), 2.54 (3H, s), 3.84 (3H, s), 6.53 (1H, d, J 0.55 Hz); E.I. m/e 138 (95%), NH$_3$DCI m/e 139 (100%).

Preparation 3

(3S,4R)-[(R)-1-t-Butyldimethylsilyloxyethyl]-4-[(1,5-dimethylpyrazol-3-ylcarbonyl)methyl]azetidin-2-one

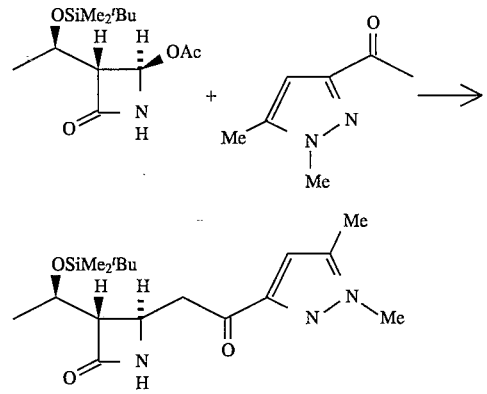

3-Acetyl-1,5-dimethylpyrazole (0.770 g, 5.1 mM) was dissolved in dry THF (10 ml) under an atmosphere of argon. The solution was cooled to −78° C. and a solution of lithium hexamethyldisilazide (1M solution in hexane; 5.1 ml; 5.1 mM) added by rapid dropwise addition. After stirring at −78° C. for 30 min a solution of 4-acetoxy-3-[(R)-1-t-butyldimethylsilyloxyethyl]-azetidin-2-one in THF (10 ml)

was added. Stirring was continued for 2 h at −78° C. The reaction was treated with saturated ammonium chloride solution followed by ethyl acetate. After allowing to warm to room temperature the organic phase was washed with water and brine before drying (MgSO$_4$). Purification was accomplished by chromatography on silica gel (10×3 cm) loading in dichloromethane and eluting with 70% ethyl acetate in hexane. The title compound was isolated as a gum (0.539 g); $v_{max}$ (CH$_2$Cl$_2$) 3411, 1761, and 1679 cm$^{-1}$; $\delta_H$ (CDCl$_3$) 0.08 (6H, s), 0.86 (9H, s), 1.21 (3H, d, J 6.28 Hz), 2.31 (3H, s), 2.89 (1H, dd, J 4.84, 2.37Hz), 3.13 (1H, dd, J 17.12, 10.05 Hz) and 3.48 (1H, dd, J 17.10, 3.41 Hz) (ABX), 3.84 (3H, s), 4.09 (1H, dt, J 9.13, 2.46 Hz) 4.13–4.25 (1H, m), 6.09 (1H, bs), and 6.54 (1H,s); m/e 365.2134 (C$_{18}$H$_3$N$_3$O$_3$S, requires 365.2135)

Preparation 4

Allyl{(3S,4R)-[(R)-1-t-butyldimethylsilyloxyethyl]-4-[(1,5-dimethylpyrazol-3-ylcarbonyl)methyl]-2-oxoazetidin-1-yl}triphenyl-phosphoranylidene acetate

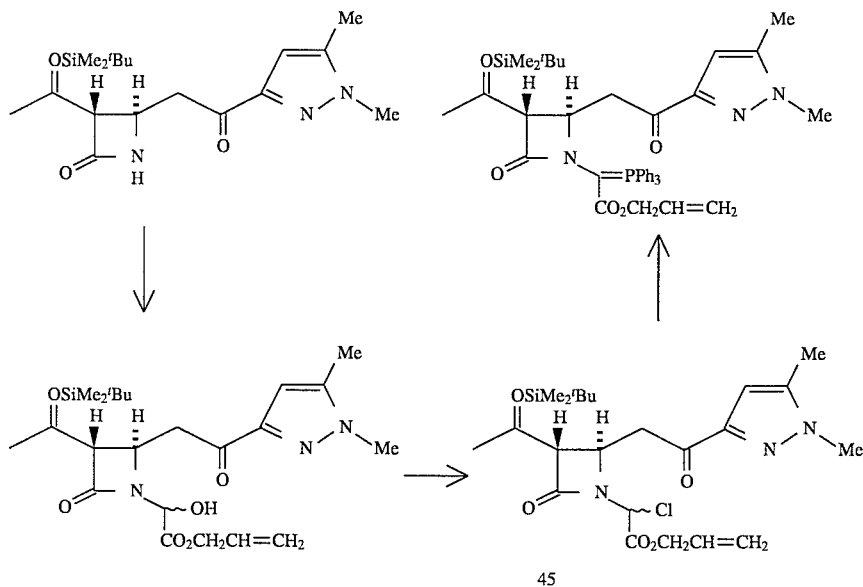

(3S,4R)-3-[(R)-1-t-buryldimethylsilyloxyethyl]-4-[(1,5-dimethylpyrazol-3-ylcarbonyl)methyl]azetidin-2-one (0.736 g, 2.0 mM) and allylglyoxylate monohydrate (0.662 g, 5.0 mM) were dissolved in benzene (25 ml) and the mixture warmed to reflux, with provision for azeotropic removal of water, whilst under an atmoshpere of argon. The reaction was held at reflux for 1 h and then allowed to cool to room temperature. Triethylamine (~4 drops) was added and the reaction stirred for 16 h at room temperature. The solvent was removed under reduced pressure and the resulting residue dissolved in 70% ethyl acetate in hexane. Purification was accomplished by chromatography on silica gel (12×3 cm) eluting with 70% ethyl acetate in hexane. The 1:1 mixture of diastereomeric hemiaminals was isolated as a yellow oil (0.983 g); $v_{max}$ (CH$_2$Cl$_2$) 3683, 3517 (broad), 1757, 1677, and 1375 cm$^{-1}$.

The diastereomeric mixture of hemiaminals (0.983 g, 2.0 mM) in THF (15 ml) was treated with 2,6-lutidine (0.357 ml, 3.0 mM) and thionyl chloride (0.225 ml, 3.0 mM) whilst at −10° C. under an atmosphere of argon. The mixture was stirred for 1 h at −10° C. The heterogeneous solution which resulted was treated with toluene and then filtered through Keiselguhr. The solvent was removed under reduced pressure. The resulting residue was triturated with toluene and filtered through Keiselguhr. Removal of solvent under reduced pressure gave a diastereomeric mixture of chlorides as a yellow oil (1.064 g).

The above product was dissolved in dioxan (6 ml) and treated with triphenylphosphine (2.15 g, 8 mM) and 2,6-lutidine (0.262 ml, 2.2 mM) whilst under an atmosphere of argon. The reaction was stirred at room temperature for 4 h. Ethyl acetate was added to the reaction mixture and the resulting organic phase was washed sequentially with 5% citric acid (a.q.), saturated sodium bicarbonate (a.q.), and brine. After drying (MgSO$_4$) and removal of solvent the crude material was purified by chromatography on silica gel (10×4.5 cm), loading in dichloromethane and eluting with 70% ethyl acetate in hexane. The title compound was isolated as a foam (1.01 g); $v_{max}$ (CH$_2$Cl$_2$) 1736, 1678, and 1610 cm$^{-1}$; m/e (NH$_3$DCI) 724 (MH$^+$), (EI) 723 (M$^+$).

Preparation 5

Allyl{(5R6S)-6-[(R)-1-t-butyldimethylsilyloxyethyl]-2-[(1,5-dimethylpyrazol-3-yl)carbapen-2-em-3-carboxylate

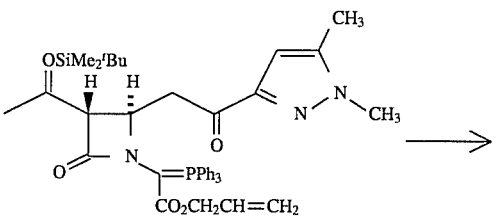

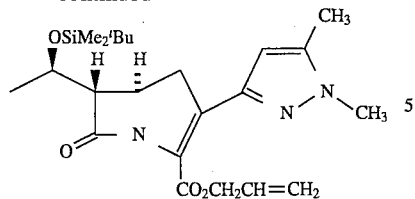

The phosphorane from Preparation 2 (0.75 g) and hydroquinone (1 mg) were dissolved in dry toluene (75 ml) under an atmosphere of argon. The reaction was warmed to reflux and stirred for 5 h. After cooling, the solvent was evaporated and the product purified by chromatography over silica gel (7×3 cm), loading in dichloromethane and eluting with 50% ethyl acetate in hexane followed by ethyl acetate. The title compound was isolated as a crystalline solid (0.314 g); m.p. (ethyl acetate/hexane) 119° C.; $v_{max}$ ($CH_2Cl_2$) 2931, 1773, 1716, 1600, and 1548 cm$^{-1}$; $\delta_H$ ($CDCl_3$) 0.09 (6H, s), 0.88 (9H, s), 1.27 (3H, d, J 6.2 Hz), 2.27 (3H, s), 3.12 (1H, dd, J 6.68, 2.74 Hz), 3.23 (1H, dd, J 18.44, 9.06 Hz) and 3.54 (1H, dd, J 18.37, 9.98 Hz) (ABX), 3.77 (3H, s), 4.11–4.27 (2H, m), 4.67–4.86 (2H, m) 5.25 (1H, dd, J 10.54, 1.21 Hz), 5.45 (1H, dd, J 17.25, 1.58 Hz), 5.91–.6.07 (1H, m) 7.02 (1H, s); m/e 445.2395 ($C_{23}H_{35}N_3O_4Si$ requires 445.2397).

Preparation 6

Allyl(5R6S)-6-[(R)-1-hydroxyethyl]-2-(1,5-dimethylpyrazol-3-yl)carbapen-2-em-3-carboxylate

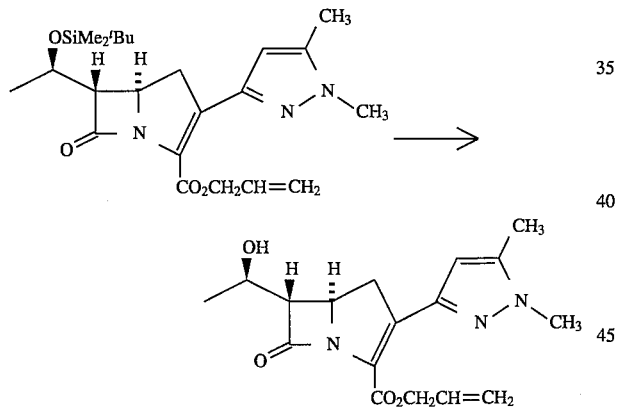

The t-butyldimethylsilyl ether from Preparation 3 (0.355 g, 0.68 mM) was dissolved in dry THF (40 ml) and treated with glacial acetic acid (0.4111 mg) and tetra-n-butyl ammonium fluoride (2.05 ml of 1.0M solution in THF) before stirring at room temperature for 24 h. The mixture was diluted with ethyl acetate and washed with sat. sodium hydrogen carbonate and brine. The organic layer was dried (MgSO$_4$) and evaporated at reduced pressure. The residue was purified by chromatography over silica gel (4×2.5 cm), loading and eluting with ethyl acetate followed by 2% ethanol in ethyl acetate. Removal of solvent gave the title compound as a crystalline solid (0.071 g); $v_{max}$ ($CH_2Cl_2$) 3603, 3506, 2973, 1774, 1719 (shoulder), and 1702 cm$^{-1}$; $\delta_H$ (d$_6$-acetone) 1.28 (3H, d, J 6.3 Hz), 2.22 (3H, s), 2.94–3.34(2H, m), 3.52 (1H, dd, J 18.5, 10.1 Hz), 3.78 (3H, s), 4.05–4.25 (2H, m), 4.64–4.83 (2H, m) 5.18–5.24 (1H, m), 5.43–5.52 (1H, m), 5.92–.6.05 (1H, m), 6.96 (1H, s); m/e 331.1534 ($C_{17}H_{21}N_3O_4$ requires 331.1532).

Preparation 7

Sodium (5R6S)-6-[(R)-1-hydroxyethyl]-2-(1,5-dimethylpyrazol-3-yl)carbapen-2-em-3-carboxylate

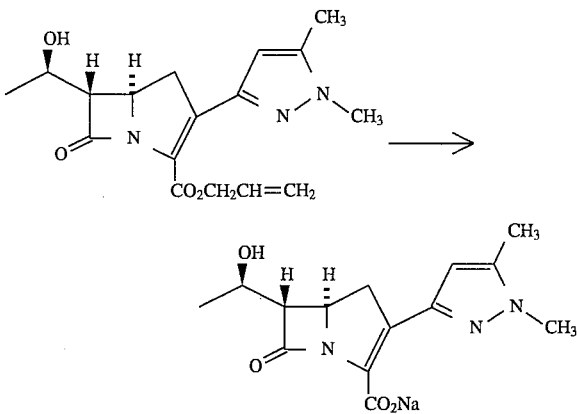

A solution of the allyl ester from Preparation 4 (0.017 g, 0.21 mM) triphenyphosphine (0.006 g, 0.021mM), sodium 2-ethylhexanoate (0.428 ml of 0.5M solution in ethyl acetate) and tetrakis (triphenylphosphine)palladium (0) (0.008 mg, 0.006 mM) in dichloro-methane/ethylacetate (1:1, 8 ml) was stirred under an atmosphere of argon for 1 h. Solvent was removed in vacuo until precipitation occurred and the resulting heterogeneous mixture transferred to centrifuge tube. Ether was added and the mixture triturated prior to centrifugation and removal of the supernatant. The solid was again triturated with ether and the solid collected by centrifugation and decantation. The solid was dried under a stream of argon before redissolving in water and filtering (GF/F, 0.7 μm). The title compound was isolated as a white fluffy solid after lyophilization (0.044 g); $\lambda_{max}$ ($H_2O$) 297.5 nm (ε8769); $v_{max}$ (KBr disc) 1795, 1771, 1612, and 1586 cm$^{-1}$; $\delta_H$ ($D_2O$) 1.28 (3H, d, J 6.42 Hz), 2.23 (3H, s), 3.16–3.21 (2H, m), 3.47 (1H, dd, J 5.93, 2.85 Hz) 3.70 (3H, s), 4.21–4.28 (2H, m), 6.43 (1H, s); m/e (thioglycerol, FAB) 314 (MH$^+$), 336 (MNa$^+$).

EXAMPLE 2

Sodium-(5R,6S)-6-[(1R)-hydroxyethyl]-2-(1-phenylpyrazol-3-yl)-carbapen-2-em-3-carboxylate Preparation 1 p-Nitrobenzyl-(5R,6S)-6-[(1R)-hydroxyethyl]-2-(1-phenylpyrazol-3-yl)carbapen-2-em-3-carboxylate To a solution of p-nitrobenzyl-(3R,5R,6S)-6-[(1R)-hydroxyethyl]-2-oxo-carbapenam-3-carboxylate (460 mg, 1.32 mmol) in THF (14 ml) cooled in an acetone/CO$_2$ bath under argon atmosphere, was added diisopropylamine (215 ul, 1.53 mmol) followed after 5 minutes by trifluoromethanesulphonic arthydride (255 ul, 1.52 mmol). The resultant yellow solution was stirred with cooling for 30 minutes.

Meanwhile triphenyl arsine (42 mg, 0.14 mmol) was added to a solution of Pd$_2$(dba)$_3$ (63 mg, 0.07 mmol) in THF (5 ml) under argon. After stirring at room temperature for 5 minutes, the deep red solution was then added to the crude triflate solution and the flask rinsed with THF (2 ml). Zinc chloride (2.76 ml of a 1.0M solution in ether, 2.76 mmol) and solid lithium chloride (117 mg, 2.76 mmol) were added to the mixture followed by a solution of 1-phenyl-3-tributylstannyl-pyrazole (600 mg, 1.38 mmol) (prepared by the method of T. Sakamoto, F. Shiga, D. Uchiyama, Y. Kondo and H. Yamanaka, Heterocycles, 1992, 33, 813) in THF (10 ml). The reaction mixture was removed from the cooling bath and stirred for 3 h. The mixture was then concentrated, chromatographed (silica gel, ethyl acetate/hexane) and the partially purified product triturated with ether to afford the title compound (417 mg, 67%). $v_{max}(CH_2Cl_2)$ 1776, 1722 cm$^{-1}$; $\delta_H(CDCl_3)$ 8.24 (2H, d, J=8.8 Hz), 7.92 (1H, d, J=2.7 Hz), 7.70 (4H, m), 7.47 (3H, m), 7.32 (1H, t, J=7.3 Hz), 5.56 (1H, d, J=13.9 Hz), 5.30 (1H, d, J=13.9 Hz), 4.31 (2H, m), 3.78 (1H, dd, J=18.8, 10.0 Hz), 3.45 (1H, dd, J=18.8, 9.0 Hz), 3.28 (1H, dd, J=6.4, 2.8 Hz), 1.74 (1H, d, J=4.9 Hz), 1.41 (3H, d, J=6.3 Hz); m/z 474.1545 (M$^+$), calculated for $C_{25}H_{22}N_4O_6$ 474.1538.

Preparation 2

Sodium-(5R,6S)-6-[(1R)-hydroxyethyl]-2-(1-phenylpyrazol-3-yl)-carbapen-2-em-3-carboxylate The product from preparation 1 (206 mg, 0.43 mmol) was suspended in THF (1 ml) and treated with (1:3) THF/0.35M phosphate buffer (pH 6) (5 ml) followed by zinc dust (2 g, 0.03 mol). The mixture was then rapidly stirred at room temperature for 2 h. The mixture was then filtered and the residue thoroughly washed with water. The pH of the filtrate was checked at pH7, and then washed with ethyl acetate. The aqueous phase was concentrated to approximately 10 ml and the crude product purified by reverse phase chromatography (HP20SS, THF/water mixtures). The product containing fractions were partially concentrated and freeze-dried to afford the title compound (72 mg, 46% ). UV (H$_2$O) $\lambda_{max}$ 307 nm (16027); $v_{max}$(KBr disc) 1750 cm$^{-1}$; $\delta_H(D_2O)$ 8.02 (1H, d, J=2.5 Hz), 7.61 (2H, d, J=8.3 Hz), 7.49 (2H, t, J=7.6 Hz), 7.36 (1H, t, J=6.9 Hz), 6.82 (1H, d, J=2.5 Hz), 4.23 (2H, m), 3.48 (1H, dd, J=5.4,2.4 Hz), 3.27 (2H, d, J=9.0 Hz), 1.27 (3H, d, J=6.3 Hz); m/z (thioglycerol) 384 (MNa$^+$), 362 (MH$^+$).

EXAMPLE 3

Sodium-(5R,6S)-6-[(1R)-hydroxyethyl]-2-(1-methylpyrazol-3-yl)-carbapen-2-em-3-carboxylate Preparation 1 p-Nitrobenzyl-(5R,6S)-6-[(1R)-hydroxyethyl]-2-(1-methylpyrazol-3-yl)carbapen-2-em-3-carboxylate The title compound (185 mg, 65%) was prepared as in Example 2, Preparation 1. $v_{max}(CH_2Cl_2)$ 1775, 1713 cm$^1$; $\delta_H$(d$^6$ acetone) 8.26 (2H, d, J=8.7 Hz), 7.85 (2H, d, J=8.7 Hz), 7.61 (1H, d, J=2.3 Hz), 7.22 (1H, d, J=2.3 Hz), 5.58 (1H, d, J=14.2 Hz), 5.37 (1H, d, J=14.2 Hz), 4.28 (1H, td, J=9.6,2.6Hz), 4.19 (1H, quintet, J=6.1 Hz), 3.92 (3H, s), 3.60 (1H, dd, J=18.7,9.9 Hz), 3.39 (1H, dd, J=18.7,9.0 Hz), 3.36 (1H, dd, J=6.3,3.0 Hz), 1.47 (1H, d, J=6.1 Hz), 1.31 (3H, d, J=6.2 Hz); m/z 412.1389 (M$^+$), calculated for $C_{20}H_{20}N_4O_6$, 412.1384.

Preparation 2

Sodium-(5R,6S)-6-[(1R)-hydroxyethyl]-2-(1-methylpyrazol-3-yl)-carbapen-2-em-3-carboxylate The product from Preparation 1 was deprotected as in Example 2 Preparation 2, to afford the title compound (16.7 mg, 13%).UV (H$_2$O)

$\lambda_{max}$ 296 nm (7413); $v_{max}$(KBr disc) 1761 cm$^{-1}$; $\delta_H(D_2O)$ 7.54 (1H, d, J=2.4 Hz), 6.65 (1H, d, J=2.4 Hz), 4.28 (2H, m), 3.86 (3H, s), 3.50 (1H, m), 3.28 (1H, dd, J=17.0,8.6 Hz), 3.18 (1H, dd, J=17.0,9.7 Hz), 1.31 (3H, d, J=6.5 Hz).

EXAMPLE 4

Sodium (5R,6S)-6-[(R)-1-hydroxyethyl]-2-(5-methyl-1-phenethylpyrazol-3-yl)carbapen-2-em-3-carboxylate Preparation 1

Ethyl 5-methyl-1-phenethylpyrazole-3-carboxylate

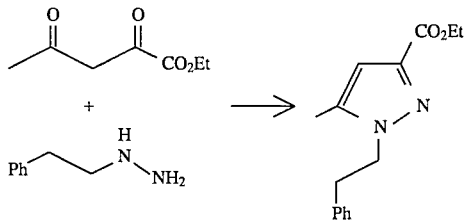

The title compound was prepared from phenethyl hydrazine (3.92 g, 0.029M)(obtained by the method of J. H. Biel U.S. Pat. No. 3,000,903) and ethyl 2,4-dioxovalerate (4.55 g, 0.029M) as described in Example 1, Preparation 1 as a yellow oil (3.84 g, 52%); $v_{max}(CH_2Cl_2)$ 1720 cm$^{-1}$;

$\delta_H(CDCl_3)$ 1.40 (3H, t, J7 Hz), 1.90 (3H, s), 3.14 (2H, t, J7 Hz), 4.30 (2H, t, J7 Hz), 4.41 (2H, q, J7 Hz), 6.48 (1H, s), 6.97–7.09 (2H, m), and 7.20–7.37 (3H, m); E.I. m/e 258.

Preparation 2

5-Methyl-1-phenethylpyrazole-3-carboxlic acid

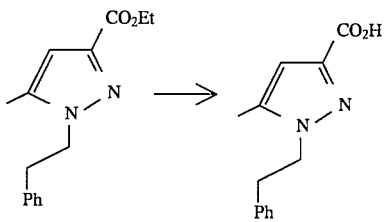

Ethyl 5-methyl-1-phenethylpyrazole-3-carboxylate (3.84 g, 14.9 mM) in ethanol (30 ml) with sodium hydroxide (0.6 g 14.9 mM) was stirred at room temperature for 3 days. The mixture was then diluted with ethyl acetate and water and the layers separated. The organic phase was further extracted with water. The combined aqueous extracts were acidified to pH 2.0 with 5M hydrochloric acid and extracted with dichloromethane. The organic extracts were dried (MgSO$_4$) and evaporated to give the title compound (3.24 g, 95%); $v_{max}(CH_2Cl_2)$ 1759 and 1699 cm$^{-1}$; $\delta_H(CDCl_3)$ 1.91 (3H, s), 3.16 (2H, t, J7 Hz), 4.31 (2H, t, J7 Hz), 6.54 (1H, s), 6.98–7.10 (2H, m), and 7.20–7.37 (3H, m).

Preparation 3

5-Methyl-1-phenethylpyrazol-yl-(N-methoxy-N-methyl)carboxamide

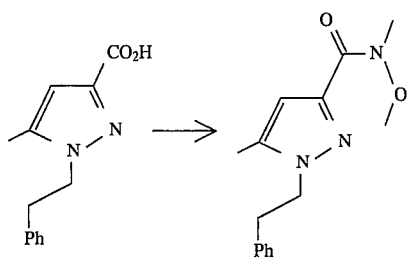

5-Methyl-1-phenethylpyrazole-3-carboxylate (3.24 g, 14.1 mM) in dichloromethane (50 ml) and dimethylformamide (1 drop) was treated with oxalyl chloride (1.4 ml, 16.9 mM). The mixture was stirred for 1.5 h to give a clear solution, which was evaporated to dryness. The residue was dissolved in toluene and evaporated. The acid chloride was dissolved in chloroform (75 ml) and N,O-dimethylhydroxylamine (1.5 g, 15.4 mM) was added. The mixture was cooled to below 5° C. and maintained at this temperature while pyridine (2.5 ml, 30.8 mM) was added. Once addition was complete the mixture was a stirred at room temperature for 1.5 h, then evaporated. The residue was dissolved in 1:1 dichloromethane, diethyl ether and brine. The organic phase was separated, dried (MgSO$_4$) and evaporated. Purification on silica gel eluting with 50–67% ethyl acetate in hexane gave an off white solid (3.37 g, 88%); $v_{max}$(CH$_2$Cl$_2$) 1641 cm$^{-1}$ $\delta_H$(CDCl$_3$) 1.93 (3H, s), 3.14 (2H, t, J7 Hz), 3.44 (3H, s), 3.76 (3H, s), 4.28 (2H, t, J7 Hz), 6.43 (1H, s), 7.00–7.10 (2H, m), and 7.15–7.35 (3H, m); NH$_3$DCI m/e 274 (100%).

Preparation 4

3-Acetyl-5-methyl-1-phenethylpyrazole

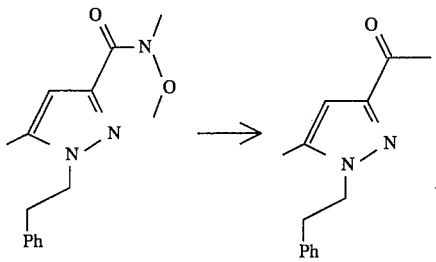

5-Methyl-1-Phenethylpyrazol-3-yl-(N-methoxy-N-methyl)carboxamide (3.37 g, 12.3 mM) in THF (30 ml) was cooled to below 0° C. and maintained at that temperature while 3.0M methyl magnesium bromide in THF (8.6 ml, 25.9 mM) was added dropwise. The mixture was stirred at 0° C. for 1.75 h then poured into ice cold 5% hydrochloric acid in ethanol. The mixture was diluted with 1:1 dichloromethane, diethyl ether and brine. The aqueous phase was again extracted with 1:1 dichloromethane, diethyl ether and the combined organic extracts were dried (MgSO$_4$) and evaporated. Purification on silica gel gave the title compound (2.65 g, 94%); $v_{max}$(CH$_2$Cl$_2$) 1680 cm$^{-1}$; $\delta_H$ (CDCl$_3$) 1.91 (3H, s), 2.58 (3H, s), 3.15 (2H, t, J7 Hz), 4.28 (2H, t, J7 Hz), 6.44 (1H, s), 6.96–7.07 (2H, m), and 7.18–7.37 (3H, m); E.I. m/e 228 (93%).

Preparation 5

(3S,4R)-[(R)-1-t-Butyldimethylsilyloxyethyl]-4-[(5-methyl-1-phenethylpyrazol-3-ylcarbony)methyl]azetidin-2-one

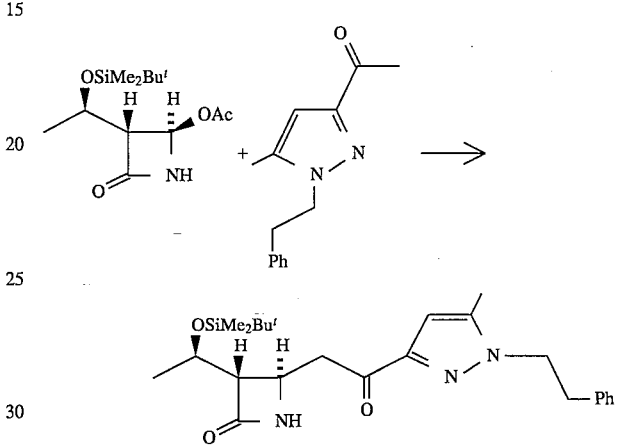

3-Acetyl-5-methyl-1-phenethylpyrazole (2.65 g, 11.6 mM) in THF (80 ml) was cooled to −70° C. and treated with 1M lithium hexamethyldisilazide in hexane (11.6 ml). The mixture was stirred at −70° C. for 0.5 h, then treated with a solution of 4-acetoxy-3-[(R)-1-t-butyldimethylsilyloxyethyl]azetidin-2-one in THF (20 ml). The mixture was stirred for a further 3 h at −70° C. Saturated ammonium chloride solution was added followed by ethyl acetate. After allowing the mixture to warm to room temperature the organic phase was separated, washed with water and brine, dried (MgSO$_4$) and evaporated. Purification on silica gel eluting with 50% ethyl acetate in hexane gave the title compound as a pale yellow solid (2.11 g, 80%); $v_{max}$(KBr) 1734 and 1680 cm$^{-1}$; $\delta_H$(CDCl$_3$) 0.08 (6H, s), 0.88 (9H, s), 1.23 (3H, d, J7 Hz), 1.91 (3H, s), 2.92 (1H, dd, J5,2 Hz), 3.08–3.29 (3H, m), 3.53 (1H, dd, J3,17 Hz), 4.05–4.34 (4H, m), 6.13 (1H, brs), 6.45 (1H, s), 6.95–7.07 (2H, m), and 7.13–7.38 (3H, m); NH$_3$DCI m/e 456 (84%).

Preparation 6

Allyl{(3S,4R)-[(R)-1-t-butyldimethylsilyloxyethyl]-4-[(5-methyl-1-phenethylpyrazol-3-ylcarbonyl)methyl]-2-oxoazetidin-1-yl}tributylphosphoranylidene acetate 23                                          24

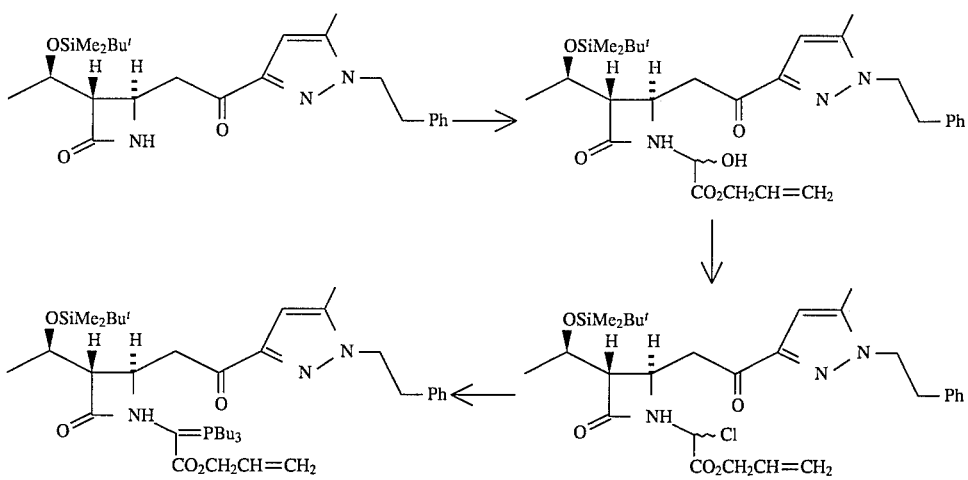

(3S,4R)-[(R)-1-t-Butyldimethylsilyloxyethyl]-4-[(5-methyl-1-phenethylpyrazol-3-ylcarbonyl)methyl]azetidin-2-one (2.11 g, 4.64 mM) and allyl glyoxylate monohydrate (1.2 g, 9.1 mM) were combined in toluene (175 ml) and heated to reflux with provision for azeotropic removal of water, under an atmosphere of argon. After 14 h the mixture was allowed to cool to room temperature, evaporated to low volume and purified on silica gel eluting with 50% ethyl acetate in hexane to give a yellow oil (1.47 g, 56%); NH$_3$DCI m/e 456 (50%).

The diastereoisomeric mixture of hemiaminals (1.1 g, 1.93 mM) in THF (50 ml) was cooled to −10° C. under argon and treated successively with 2,6-lutidine (0.33 ml, 2.8 mM) and thionyl chloride (0.22 ml, 2.5 mM). The mixture was stirred at −5° to −10° C. for 0.75 h. then diluted with toluene filtered through celite and evaporated. The above product was dissolved in dioxan (10 ml) and treated with tributylphosphine (1.1 ml, 5.5 mM) under argon. After stirring for 1.5 h the mixture was diluted with ethyl acetate washed with saturated aqueous sodium hydrogen carbonate solution, brine, dried (MgSO$_4$) and evaporated. Purification on silica gel eluting with 33–50% ethyl acetate in hexane gave a clear oil (1.016 g. 70%); $v_{max}$(CH$_2$Cl$_2$) 1737, 1677, and 1604 cm$^{-1}$.

Preparation 7

Allyl{(5R,6S)-6-[(R)-1-hydroxyethyl]-2-(5-methyl-1-phenethylpyrazol-3-yl)}carbapen-2-em-3-carboxylate

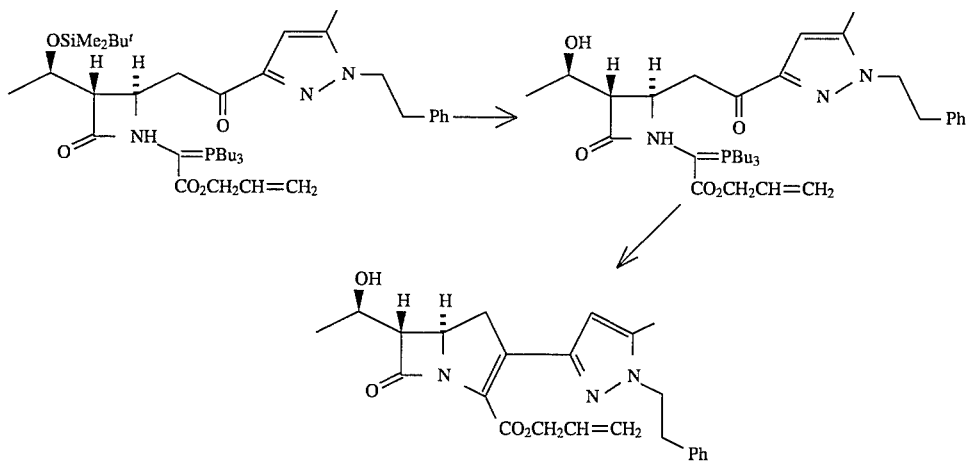

Allyl{(3S,4R)-[(R)-1-t-butyldimethylsilyloxyethyl]-4-[(5-methyl-1-phenethylpyrazol-3-ylcarbonyl)methyl]-2-oxoazetidin-1-yl}tributylphosphoranylidene acetate (0.7 g, 0.9 mM) in methanol (30 ml) was treated with 2M hydrochloric acid (8.1 ml) and stirred for 2 h. The solution was evaporated to low volume and extracted twice with ethyl acetate. The organic extracts were combined, washed with brine, dried (MgSO$_4$) and evaporated. The residue was diluted with toluene (5 ml) and evaporated. The residue was dissolved in toluene (30 ml) and heated to reflux for 2 h then allowed to cool and evaporated to low volume. Purification on silica gel eluting with ethyl acetate gave an oil (0.164 g, 42%); ν$_{max}$(CH$_2$Cl$_2$) 1774 and 1717 cm$^{-1}$;

δ$_H$(CDCl$_3$) 1.37 (3H, d, J6 Hz), 1.93 (3H, s), 3.09 (3H, t, J7 Hz), 3.22 (1H, m), 3.32 (1H, dd, J9,19 Hz), 3.64 (1H, dd, J10,19 Hz), 4.12–4.37 (4H, m), 4.64–4.90 (2H, m), 5.29 (1H, dd, J1,9 Hz), 5.47 (1H, dt, J1.5,16 Hz), 5.90–6.10 (1H, m), 6.94 (1H, s), 6.97–7.09 (2H, m), and 7.15–7.35(3H, m); m/e 421.2001(C$_{24}$H$_{27}$N$_3$O$_4$ requires 421.2002).

Preparation 8

Sodium {(5R,6S)-6-[(R)-1-hydroxyethyl]-2-(5-methyl-1-phenethylpyrazol-3-yl)}carbapen-2-em-3-carboxylate

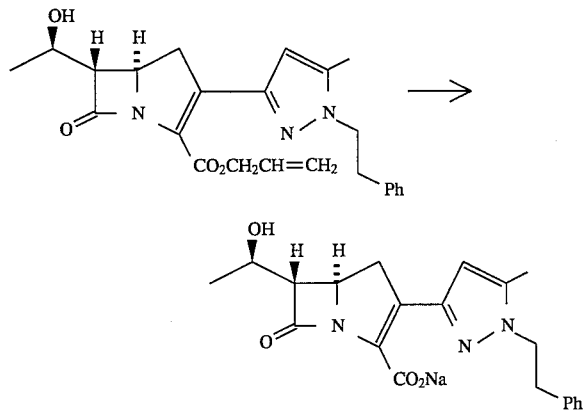

Allyl{(5R,6S)-6-[(R)-1-hydroxyethyl]-2-(5-methyl-1-phenethylpyrazol-3-yl)}carbapen-2-em-3-carboxylate (0.21 g, 0.48 mM) in 1:1dichloromethane, ethyl acetate was treated sequentially with triphenyl phosphine (0.014 g, 0.05 mM), sodium 2-ethylhexanoate (0.073 g, 0.04 mM) in ethyl acetate (1.5 ml), tetrakis(triphenylphosphine)palladium (0.022 g, 0.019 mM). The mixture was stirred at room temperature for 20 minutes then evaporated to low volume and transferred to a centrifuge tube. The remaining solvent was removed by passing a stream of argon over the surface of the mixture. The residue was triturated with diethyl ether then centrifuged and the supernatent removed. The procedure was repeated twice more and the residual orange solid was purified on Diaion HP20SS resin eluting with water, THF mixtures. Lyophilisation gave the title compound as a pale yellow fluffy solid (0.087 g, 45%); λ$_{max}$(H$_2$O) 298.5 nm (e 8611); ν$_{max}$(KBr) 1752 cm$^{-1}$.

δ$_H$(D$_2$O) 1.28 (3H, d, J6.4 Hz), 1.77 (3H, s), 3.04 (2H, t, J6.5 Hz), 3.17 (2H, m), 3.45 (1H, m), 4.22 (4H, m), 6.28 (1H, s), 6.90–7.08 (2H, m), and 7.23 (3H, m); m/e (glycerol, FAB) 404 (MH$^+$), 426 (MNa$^+$).

EXAMPLE 5

Sodium (5R,6S)-6-[(R)-1-hydroxyethyl)]-2-[1-(2-phenethyl)pyrazol-3-yl]carbapen-2-em-3-carboxylate Preparation 1

4-Nitrobenzyl 2-phenethylglycine

Phenethylamine (4.51 ml, 36 mM) in dichloromethane (100 ml) with triethylamine (5.51 ml, 39.6 mM) was cooled in ice and treated dropwise with a solution of 4-nitrobenzyl bromoacetate (9.9 g, 36 mM) in dichloromethane (50 ml). The mixture was stirred at room temperature for 2.5 h, then washed with saturated aqueous sodium hydrogen carbonate solution, brine, dried (MgSO$_4$) and evaporated. Purification on silica gel eluting with 30–100% ethylacetate in hexane gave an orange oil (7.23 g, 64%); u$_{max}$(CH$_2$Cl$_2$) 1766, 1608, and 1526 cm$^{-1}$; d$_H$(CDCl$_3$) 2.78–2.95 (4H, m), 3.52 (2H, s), 5.24 (2H, s), 7.16–7.39 (5H, m), 7.50 (2H, d, J 8 Hz), and 8.22 (2H, d, J 8 Hz); EI m/e 315 (MH$^+$).

Preparation 2

3-(2-Phenethyl)-1,2,3-oxadiazol-5-one

4-Nitrobenzyl 2-phenethylglycine (7.23 g, 23 mM) in ethanol (50 ml) with saturated aqueous sodium hydrogen carbonate solution (20 ml) was hydrogenareal over 10% palladium on charcoal (0.4 g). After 1.25 h the mixture was diluted with saturated sodium hydrogen carbonate (20 ml) and filtered through celite. After removal of ethanol under reduced pressure the aqueous mixture was washed with dichloromethane, and evaporated to dryness. The residue was treated with 5M hydrochloric acid. The precipitated white solid was filtered and washed with 1M HCl.

The acid obtained above was suspended in 12% hydrochloric acid (200 ml) and treated with sodium nitrite (3.6 g, 52 mM). The mixture was heated at 60° C. overnight then evaporated to dryness. The residue was triturated with acetone then filtered to remove insoluble solid. The filtrate was evaporated to give N-nitroso-2-phenethylglycine (2.6 g, 54%); u$_{max}$ (CH$_2$Cl$_2$) 1726 and 1461 cm$^{-1}$; d$_H$ (CDCl$_3$) 3.04 (2H, t, J 7.5 Hz) 4.28 (2H, s), 4.40 (2H, t, J 7.5 Hz), 7.29 (5H, m), and 1290 (1H, br s).

N-Nitroso 2-phenethylglycine (2.6 g, 12.4 mM) in dichloromethane (25 ml) was cooled in ice and treated dropwise with trifluoroacetic anhydride (2.6 ml, 18.4 mM). After being stirred with cooling for 25 minutes the mixture was neutralised with solid sodium hydrogen carbonate and a miniumum quantity of water. The layers were separated and the aqueous phase extracted with dichloromethane. The combined organic extracts were washed with brine, dried (MgSO$_4$) and evaporated to give the title compound as an oil (1.79 g, 76%); u$_{max}$ (CH$_2$Cl$_2$) 1752 and 1424 cm$^{-1}$; d$_H$ (CDCl$_3$) 3.25 (2H, t, J 7 Hz), 4.49 (3H, t, J 7 Hz), 6.12 (1H, s), and 7.10–7.42 (5H, m); EI m/e 190 (83%).

Preparation 3

1-(2-Phenethyl)-3-(tributylstannyl)pyrazole 3-(2-Phenethyl)-1,2,3-oxadiazol-5-one (1.79 g, 9.4 mM) in xylene (20 ml) with ethynyltributyltin (5.56 ml, 19.2 mM) was heated at reflux for 18 h. The mixture was allowed to cool then purified on silica gel eluting with 0–20% diethyl ether in hexane to give the title compound (2.0 g, 46%); u$_{max}$ (CH$_2$Cl$_2$) 1425 cm$^{-1}$; d$_H$ (CDCl$_3$) 0.89 (9H, t, J 7 Hz), 1.03–1.16 (6H, m), 1.25–1.42 (6H, m), 1.52–1.71 (6H, m), 3.16 (2H, t, J 7 Hz), 4.41 (2H, t, J 7 Hz), 6.25 (1H, d, J 2 Hz), 7.01–7.08 (2H, m), and 7.16–7.35 (4H, m); NH$_3$DCI m/e 463 (25%).

Preparation 4

4-Nitrobenzyl (5R,6S)-6-[(R)-1-hydroxyethyl)-2-[1-(2-phenethyl)pyrazol-3-yl]carbapen-2-em-3-carboxylate The title compound was prepared from 1-(2-phenethyl)-3-(tributylstannyl)-pyrazole (2.0 g, 4.3 mM) as described in Example 2, Preparation 1 (1.57 g, 73%); u$_{max}$ (KBr) 1769, 1740, 1604 and 1523 cm$^{-1}$; d$_H$ (CDCl$_3$) 1.40 (3H, d, J 6.5 Hz), 3.15 (3H, t, J 7 Hz), 3.26 (1H, m), 3.36 (1H, dd, J 9, 19 Hz), 3.68 (1H, dd, J 10, 19 Hz), 4.20–4.41 (4H, m), 5.28,5.54 (2H, ABq, J 14 Hz), 7.03–7.39 (5H, m), 7.69 (2H, d, J 8.5 Hz), and 8.23 (2H, d, J 8.5 Hz); m/e 502.1858 (C$_{27}$H$_{26}$N$_4$O$_6$ requires 502.1852).

Preparation 5

Sodium (5R,6S)-6-[(R)-1-hydroxyethyl)]-2-[1-(2-phenethyl)pyrazol-3-yl]carbapen-2-em-3-carboxylate 4-Nitrobenzyl(5R,6S)-6-[(R)-1-hydroxyethyl)-2-[1-(2-phenethyl)pyrazol-3-yl]carbapen-2-em-3-carboxylate (0.20 g, 0.4 mM) in THF (15 ml) and 0.2M pH 7.0 phosphate buffer (15 ml) with sodium hydrogen carbonate (0.066 g, 0.79 mM) was hydrogenated over 10% palladium on charcoal (0.10 g). After 3.5 minutes the mixture was filtered through celite, washing the solids with water and sodium hydrogen carbonate solution. The filtrate was washed with diethyl ether, then evaporated to low volume and purified on Diaion HP20SS resin eluting with 0–2% tetrahydrofuran in water to give the title compound as a white lyophilised solid (0.051 g, 33%); λ$_{max}$ (H$_2$O) 297.5 (ε9961);ν$_{max}$ 1753, 1603 and 1591 cm$^{-1}$; δ$_H$ (D$_2$O) 1.36 (3H, d, J 6.5 Hz), 3.17 (2H, t, J 6.5 Hz), 3.20–3.35 (2H, m), 3.55 (1H, m), 4.25–4.40 (2H, m), 4.43 (2H, t, J 6.5 Hz), 6.57 (1H, d, J 2.5 Hz), 7.12–7.21 (2H, m), and 7.25–7.41 (4H, m); m/e (thioglycerol, FAB) 390 (MH$^+$).

EXAMPLE 6

Sodium (5R,6S)-6-[(R)-1-hydroxyethyl]-2-[4,5,6,7-tetrahydropyridino-(1,2-b)pyrazol-2-yl]carbapen-2-em-3-carboxylate Preparation 1

4,5,6,7-Tetrahydropyridino-(1,2-c)(1,2,3)oxadiazolone

N-Nitrosopipecolinic acid (prepared by the method of W. Lijinsky, L. Keefer and J. Loo Tetrahedron 1970, 26, 5137) (1.82 g, 11.5 mM) in dichloromethane (15 ml) was cooled in ice and treated dropwise with trifluoroacetic acid (1.62 ml, 11.5 mM). The mixture was stirred with cooling for 6 h then diluted with further dichloromethane. and washed with saturated aqueous sodium hydrogen carbonate solution until the washings were neutral. The organic phase was dried (MgSO$_4$) and evaporated to give the title compound as a yellow oil (1.12 g, 76%); ν$_{max}$ (CH$_2$Cl$_2$) 1732 cm$^{-1}$: δ$_H$(CDCl$_3$) 1.90–2.02 (2H, m), 2.04–2.19 (2H, m), 2.63 (2H, t, J 6 Hz) and 4.25 (2H, t, Y 6 Hz); EI m/e 140 (93%).

Preparation 2

4,5,6,7-Tetrahydropyridino-2-tributylstannyl(1,2-b)-pyrazole

The title compound was prepared from 4,5,6,7-tetrahydropyridino-(1,2-c) (1,2,3) oxadizole (1.12 g, 8.8 mM) by the method described in Example 5, Preparation 3 (0.458 g, 13%); ν$_{max}$ (CH$_2$Cl$_2$) 1526 and 1485 cm$^{-1}$; δ$_H$ (CDCl$_3$) 0.84–1.01 (9H, m), 1.02–1.12 (6H, m), 1.25–1.41 (6H, m), 1.50–1.72 (6H, m), 1.79–1.90 (2H, m), 1.96–2.09 (2H, m), 2.80 (2H, t, J 6 Hz), 4.21 (2H, t, J 6 Hz), and 6.05 (1H, s); NH$_3$DCI m/e MH$^+$ 413 (100%).

Preparation 3

4-Nitrobenzyl (5R,6S)-6-[(R)-1-hydroxyethyl)-2-[4,5,6-7-tetrahydropyridino(1,2-b)-pyrazol-2-yl]carbapen-2-em-3-carboxylate The title compound was prepared from 4,5,6,7-tetrahydropyridinium-2-tributylstannyl-(1,2-b)-pyrazole (0.458 g, 1.11 mM) as described in Example 2, Preparation 1 (0.38 g, 76%); ν$_{max}$ (KBr) 1773, 1714, 1597, 1539, and 1519 cm$^{-1}$; δ$_H$ (CDCl$_3$) 2.39 (3H, d, J 6 Hz), 1.58 (3H, s), 1.78–1.92 (2H, m), 1.99–2.12 (2H, m), 2.79 (2H, t, J 6 Hz), 3.21–3.25 (1H,m), 3.31 (1H, dd, J 9, 18.5 Hz), 3.63 (1H, dd, J 10, 18.5 Hz), 4.13 (2H, t, J 6 Hz), 4.17–4.36 (1H, m), 5.27, 5.54 (2H, ABq, J 14 Hz), 6.97 (1H, s), 7.69 (2H, d, J 9 Hz) and 8.23 (2H, d, J 9 Hz); m/e 452.1699 (C$_{23}$H$_{24}$N$_4$O$_6$ requires 452.1696).

Preparation 4

Sodium (5R,6S)-6-[(R)-1-hydroxyethyl]-2-[4,5,6,7-tetrahydropyridino-(1,2-b)pyrazol-2-yl]carbapen-2-em-3-carboxylate The title compound was prepared from 4-nitrobenzyl (5R,6S)-6-[(R)-1-hydroxyethyl]-2-[4,5,6,7-tetrahydropyridino-(1,2-b)-pyrazol-2-yl]carbapen-2-em-3-carboxylate (0.20 g, 0.44 mM) by the method described in Example 5, Preparation 5 as an off-white lyophilised solid (0.099 g, 66%); λ$_{max}$ (H$_2$O) 298 nm (ε7241); ν$_{max}$ (KBr) 1752, 1603, and 1575 cm$^{-1}$; δ$_H$ (D$_2$O) 1.26 (3H, d, J 6.5 Hz), 1.77 (2H, m), 1.98 (2H, m), 2.73 (2H, t, J 6 Hz), 3.08–3.22 (2H, m), 3.36–3.48 (1H, m), 4.00 (2H, t, J 6 Hz), 4.12–4.28 (2H, m), and 6.39 (1H, s); m/e 318 (MH$^+$).

EXAMPLE 7

Sodium (5R,6S)-6[(1R)-1-Hydroxyethyl]-2-(5-methyl-1-phenylpyrazol-3-yl)carbapen-2-em-3-carboxylate Preparation 1

5-Methyl-2-phenyl-3-(tri-n-butylstannyl)pyrazole

N-Phenylalanine (825 mg) in 1,2-dimethoxyethane (20 ml) was treated with n-butyl nitrite (0.64 ml) and the mixture was stirred for 2.5 h and then the solvent was removed to leave crude N-nitroso-N-phenylalanine. This was dissolved in dichloromethane (10 ml), cooled in an ice-bath and treated with trifluoroacetic anhydride (1.06 ml). The mixture was stirred for 1 h and then the solvents were removed, toluene was added and removed using a rotary evaporator. The residue was chromatographed on silica gel eluting with ethanol/chloroform mixtures to give the sydnone (1 g), $\nu_{max}$(CH$_2$Cl$_2$) 1803(sh), 1763(sh), 1734, 1485, 1243, and 1065 cm$^{-1}$; δ (CDCl$_3$) 2.16 (3H,s), 7.51–7.73 (5H, m); Found m/z 176.0590; C$_9$H$_8$N$_2$O$_2$ requires 176.0586. The sydnone in xylene (8 ml) was treated with ethynyltributylstannane and the mixture was heated under reflux for 8 h. After standing for 16 h at room temperature the mixture was diluted with hexane(15 ml) and loaded onto silica gel and eluted with hexane (100 ml) followed by hexane/ethyl acetate mixtures to give 5-methyl-2-phenyl-3-(tri-n-butylstannyl)pyrazole (602 mg), δ (CDCl$_3$) 0.87–1.76 (27H, m), 2.35 (3H, s), 6.25 (1H, s), 7.26–7.47 (5H, m); Found m/z 448.1900. C$_{22}$H$_{36}$N$_2$Sn requires 448.1900.

Preparation 2 p-Nitrobenzyl (5R,6S)-6-[(1R)-1-Hydroxyethyl]-2-(5-methyl-1-phenylpyrazol-3-yl)carbapen-2-em-3-carboxylate p-Nitrobenzyl (5R,6S)-6-[(1R)-1-hydroxyethyl]-2-oxo-carbapenam-3-carboxylate (250 mg) in dry tetrahydrofuran (10 ml) under an atmosphere of argon was cooled to –78° C. and N,N-diisopropylamine (0.11 ml) was added. The mixture was stirred for 5 minutes and then trifluoromethanesulphonic arehydride (0.13 ml) was added and the mixture stirred for a further 30 minutes to give a solution of p-nitrobenzyl (5R,6S)-6-[(1R)-1-hydroxyethyl]-2-trifluoromethylsulphonyloxy-carbapen-2-em-3-carboxylate. A solid mixture of triphenylarsine (22 mg) and tris(dibenzylideneacetone)palladium(0) (33 mg) and lithium chloride (60 mg) was added, blanketing the reaction mixture with a stream of argon. 5-Methyl-2-phenyl-3-(tri-n-butylstannyl)pyrazole (322 mg), was added and washed in with dry tetrahydrofuran (3 ml). 1M Zinc chloride in diethyl ether (1.44 ml) was then added and the mixture was warmed to room temperature using a lukewarm water bath. The mixture was stirred for 17 h and then treated with ethyl acetate/water and the layers were separated, after addition of a little brine. The aqueous layer was reextracted with ethyl acetate. Combined ethyl acetate layers were washed with water, brine and then dried (MgSO$_4$) and evaporated. The residue was chromatographed on silica gel, loading in dichloromethane. and eluting with ethyl acetate/hexane mixtures. Fractions containing the product were combined to give the product contaminated by tin residues. Rechromatography, followed by trituration with ether and filtration gave p-Nitrobenzyl (5R,6S)-6-[(1R)-1-hydroxyethyl]-2-(5-methyl-1-phenylpyrazol-3-yl)carbapen-2-em-3-carboxylate (247 mg), $\nu_{max}$(CH$_2$Cl$_2$)/cm$^{-1}$ 3603, 1775, 1724, 1600, 1525, 1501, 1350, 1315, 1267, and 1184; δ (CDCl$_3$) 1.37 (3H, d, J 6.3 Hz), 1.82 (1H, d, J 4.9 Hz), 2.33 (3H, s), 3.25 (1H, dd, J 2.7 & 6.3 Hz), 3.38 (1H, dd, J 5.9 & 18.8 Hz), 3.70 (1H, dd, J 9.9 & 18.8 Hz) 4.22–4.33 (2H, m), 5.30 (1H, d, J 13.9 Hz), 5.56 (1H, d, J 13.9 Hz), 7.19 (1H, s), 7.37–7.52 (5H, m), 7.71 (2H, d, J 8.7 Hz), and 8.24 (2H, d J 8.8 Hz); $\lambda_{max}$ (EtOH)/nm 326.5 (ε/dm$^3$ mol$^{-1}$ cm$^{-1}$ 17,137), 260.5 (ε 12,621); Found C 63.75, H 5.1, N 11.1, m/z 488.1698. C$_{26}$H$_{24}$N$_2$O$_6$ requires C 63.9, H 4.95, N 11.5. m/z 488.1696.

Preparation 3

Sodium (5R,6S)-6-[(1R)-1-Hydroxyethyl]-2-(5-methyl-1-phenylpyrazol-3-yl)carbapen-2-em-3-carboxylate p-Nitrobenzyl (5R,6S)-6[(1R)-1-hydroxyethyl]-2-(5-methyl-1-phenylpyrazol-3-yl)carbapen-2-em-3-carboxylate (122 mg) in tetrahydrofuran (THF) (10 ml) and water (10 ml) was treated with sodium hydrogen carbonate (42 mg) and 3% Pd-C catalyst (50 mg) and the mixture was hydrogenareal at atmospheric pressure for 5–10 min. The mixture was filtered through Kieselguhr, washing the filter cake with water and ethyl acetate. Combined filtrate and washings were reduced in volume using a rotary evaporator, a little NaCl was added and the mixture was chromatographed on a Diaion HP20SS column (2×10 cm), eluting with water (200 ml), followed by water/THF mixtures:—2% THF (100 ml); followed by 3% THF (100 ml), followed by 4% THF, followed by 6% THF. Fractions were monitored by uv and hplc. Fractions containing the product were combined and evaporated to lower volume and then freeze-dried to give sodium (5R,6S)-6-[(1R)-1-hydroxyethyl]-2-(5-methyl-1-phenylpyrazol-3-yl)carbapen-2-em-3-carboxylate (80 mg) $\nu_{max}$(KBr)/cm$^{-1}$ 1786, 1756, 1588, 1501, 1412, 1383, 1359, 1288 1246, 1223, and 1145; $\lambda_{max}$(H$_2$O)/nm 300.0 (ε/dm$_3$ mol$^{-1}$ cm$^{-1}$ 13,232), 236.5 (ε7,027); δ (D$_2$O) 1.26 (3H, d, J 6.4 Hz), 2.20 (3H,s), 3.1–3.29 (2H, m), 3.46 (1H, dd, J 2.9 & 5.9 Hz), 4.16–4.28 (2H, m), 6.61 (1H,s), 7.39–7.57 (5H,m);

EXAMPLE 8

Sodium (5R,6S)-2-[5,6-Dihydro-4H-pyrrolo(1,2-b)-pyrazol-2-yl]-6-[(R)-1-hydrocarbapen]carbapen-2-em-3-carboxylate Preparation 1

2-Tributylstannyl-5,6-Dihydro-4H-pyrrolo[1,2-b] pyrazole

The title compound was prepared from 5,6-dihydro-4H-pyrrolo [1,2-c][1,2,3]oxadiazolone (prepared by the method described in Tet Letters, 24, (10), 1067, 1983) and ethynyltributyltin by the procedure described in Example 5, Preparation 3; δ$_H$(CDCl$_3$)0.8–1.7 (27H, m), 2.62 (2H, q), 2.85 (2H, t), 4.17 (2H, t), 6.02 (1H, s).

Preparation 2 p-Nitrobenzyl 2-[5,6-Dihydro-4H-pyrrolo(1,2-b)-pyrazol-2-yl]-6-[(R)-1-hydroxyethyl]carbapen-2-em-3-carboxylate The title compound was prepared from 2-Tributylstannyl-5,6-Dihydro4H-pyrrolo[1,2-b]pyrazole and p-nitrobenzyl (3R,SR,6S)-6-[(1R)-hydroxyethyl]-2-oxocarbapenam-3-carboxylate by the method described in Example 2, Preparation 1; mp 187°–190° C. (EtOAc), $\lambda_{max}$(EtOH) 325 nm (16,262), 266 (12,654); $\nu_{max}$(KBr) 3286, 1790, 1706, 1608, 1583 and 1522 cm$^{-1}$; δ$_H$ (d-6 DMSO) 1.16 (3H,d, J 6.2 Hz), 2.45–2.6 (3H, m), 2.82 (2H, t), 3.23–3.52 (3H, m), 3.92–4.25 (4H, m), 5.06 (1H, d, J 3.9 Hz), 5.41 (2H, q), 6.79 (1H, s), 7.73 (2H, d, J 8.5 Hz), 8.23 (2H, d, J 8.5 Hz); (Found: C. 60.0; H, 5.0; N, 12.7% C$_{22}$H$_{22}$N$_4$O$_6$ requires: C, 60.25; H, 5.05; N, 12.8%)

Preparation 3

Sodium (5R,6S)-2-[5,6-Dihydro-4H-pyrrolo(1,2-b)-pyrazol-2-yl]-6-[(R)-1-hydroxyethyl]carbapen-2-em-3-carboxylate The title compound was prepared from p-nitrobenzyl 2-[5,6-dihydro-4H-pyrrolo(1,2-b)-pyrazol-2-yl]-6-[(R)-1-hydroxyethyl]carbapen-2-em-3-carboxylate by the procedure described in Example 5 Preparation 5; $\lambda_{max}$ (H$_2$O) 300 nm (8,753); ν$_{max}$ (KBr) 3420, 1748, 1602 and 1573 cm$^{-1}$; δ$_H$ (D$_2$O) 1.29 (3H, d, J 6.5 Hz), 2.48–2.63 (2H, m), 2.85 (2H, t), 3.1–3.3 (2H, m), 3.48 (1H, dd, J 5.9, 2.8 Hz) 4.05 (2H, t) 4.15–4.3 (2H, m), 6.41 (1H,s).

EXAMPLE 9

Sodium (5R,6S)-6-[(R)-1-hydroxyethyl]-2-(1,5-diethylpyrazol-3-yl)carbapen-2-em-3-carboxylate

Preparation 1

Ethyl 1,5-Diethylpyrazole-3-carboxylate

Ethyl 2,4-dioxohexanoate (21.5 g) in glacial acetic acid (125 ml) was cooled in an ice-bath and treated with N-ethylhydrazine oxalate (18.75 g) over 15 minutes. After addition was complete the mixture was stirred for 3 hours at room temperature. The acetic acid was then removed by evaporation in vacuo. The orange oily residue was dissolved in EtOAc and the solution washed repeatedly with saturated aqueous NaHCO$_3$ and once with brine. Following drying over MgSO$_4$ the solvent was evaporated in vacuo to give ethyl 1,5-diethylpyrazole-3-carboxylate as an oil (20.7 g); δ (CDCl$_3$) 1.25–1.45 (9H, 3×3H,t, J 7 Hz), 2.62 (2H, q, J 7 Hz), 4.17 (2H, q, J 7 Hz), 4.38 (2H, q, J 7 Hz) 6.57 (1H, s) ppm.

Preparation 2

1,5-Diethylpyrazole-3-carboxylic acid

Ethyl 1,5odiethylpyrazole-3-carboxylate (20.7 g) in ethanol (250 ml) was treated with 2.5M aqueous NaOH (50.6 ml), and the mixture was stirred overnight. A further 4.2 ml of 2.5M NaOH was then added and stirring continued for a further 1 hour. The mixture was then poured into ethyl acetate/water. The mixture was shaken vigorously and the aqueous phase removed. The pH of the aqueous phase was adjusted to 2.0 using 1M aqueous HCl and saturated with NaCl. The aqueous layer was then extracted with 20% toluene/80% THF (5×100 ml). The combined organic extracts were dried over MgSO$_4$ and evaporated in vacuo. The residue was triturated with hexane/diethyl ether to give the acid as a solid (14.69 g); ν$_{max}$(CH$_2$Cl$_2$) 3450, 2750, 2596, 1697, cm$^{-1}$; δ (CDCl$_3$) 1.31 (3H, t, J 7 Hz), 1.44 (3H, t,J 7 Hz) 2.64 (2H, q, J 7 Hz), 4.20 (2H, q, J 7 Hz), 6.64 (1H,s) ppm.

Preparation 3

N-Methoxy-N-methyl-1,5-diethylpyrazole-3-carboxamide 1,5-Diethylpyrazole-3-carboxylic acid (14.69 g) in dry dichloromethane (180 ml) containing N,N-dimethylformamide (7 drops) was treated with oxalyl chloride (8.38 ml). The mixture was stirred for 2.25 hours under an atmosphere of argon. The solvent was removed by evaporation in vacuo and the residue redissolved in fresh dry, dichloromethane and again evaporated in vacuo to ensure any residual HCl and oxalyl chloride had been removed. The resultant acid chloride was dissolved in chloroform and then treated with N,O-dimethylhydroxylamine hydrochloride (9.37 g). The mixture was cooled in an ice-bath under an atmosphere of argon and treated with pyridine (15.6 ml), added dropwise. The mixture was allowed to stir for 1 hour and then diluted with EtOAc and washed with saturated aqueous NaHCO$_3$, 0.5M aqueous HCl and brine. The organic layer was dried (MgSO$_4$) and evaporated to leave an oil. This was chromatographed on silica gel, loading in dichloromethane, and eluting with ethyl acetate/hexane mixtures to give, after evaporation of the requisite fractions, the hydroxamate (10.1 g) as an oil; ν$_{max}$ (CH$_2$Cl$_2$) 1641, 1487, 1461, 1444, and 1381 cm$^{-1}$; δ (CDCl$_3$) 1.28 (3H, t, J7 Hz), 1.43 (3H, t, J 7 Hz), 2.62 (2H, q, J 7 Hz), 3.43 (3H, s), 3.76 (3H, s), 4.12 (2H, q, J 7 Hz), 6.52 (1H, s) ppm.

Preparation 4

3-Acetyl-1,5-diethylpyrazole

N-Methoxy-N-methyl-1,5-diethylpyrazole-3-carboxamide (10.1 g) in dry tetrahydrofuran (180 ml) was cooled in an ice-bath and treated with a 3.0M solution of methylmagnesium bromide in ether (20.68 ml) added dropwise over 10 minutes. After stirring for 1 hour the mixture was treated with a mixture of ethanol (5 ml) and 5M aqueous HCl (1 ml). The mixture was then diluted with EtOAc and water. The organic phase was separated and the aqueous phase extracted twice with EtOAc. The combined organic extracts were dried over MgSO$_4$ and evaporated in vacuo to leave an oil which was chromatographed on silica gel, loading in dichloromethane, and eluting with ethyl acetate/hexane mixtures to give, after evaporation of the requisite fractions, the product as an oil (8.08 g), δ (CDCl$_3$) 1.29 (3H, t, J 7 Hz), 1.45 (3H, t, J 7 Hz), 2.55 (3H, s), 2.64 (2H, q, J 7 Hz), 4.14 (2H, q, J 7 Hz,), 6.55 (1H,s) ppm.

Preparation 5

(3S,4R)-4-[(1,5-diethylpyrazol-3-yl)carbonylmethyl]-3-[(R)-1-tert-butyldimethylsilyloxyethyl]azetidin-2-one 3-Acetyl-1,5-diethylpyrazole (1.65 g) in dry tetrahydrofuran (THF) (50 ml) under an argon atmosphere was cooled in an acetone/solid carbon dioxide bath and then treated with a 1M solution of lithium bis(trimethylsilyl)amide (19.8 ml). The mixture was stirred for 45 minutes and then (3R,4R)-4-acetoxy-3-[(R)-1-tert-butyldimethylsilyloxyethyl]azetidinone (2.84 g) in dry THF (10 ml), added by syringe over ca. 1 minute. The mixture was stirred in the cold for 5 h. Saturated aqueous ammonium chloride was then added, followed by ethyl acetate. The layers were separated and the aqueous layer was re-extracted with ethyl acetate. The combined ethyl acetate layers were washed with saturated brine. dried and evaporated. Chromatography on silica gel, eluting with ethyl acetate/hexane mixtures gave the title compound (1.82 g); ν$_{max}$(CH$_2$Cl$_2$) 3412, 2957, 2885, 2857, 1761, 1677, 1473, and 1376 cm$^{-1}$; δ (CDCl$_3$) 0.078 (6H, s), 0.88 (9H, s), 1.21 (3H,d, J 6.3 Hz), 1.29 (3H, t, J 7.6 Hz), 1.45 (3H, t, J 7.3 Hz), 2.63 (2H, q, J 7.3 Hz), 2.90 (1H, dd, J 1.6 & 4.9 Hz), 3.15 (1H, dd, J 10.0 & 17.0 Hz), 3.50 (1H, dd, J 3.6 & 17.0 Hz), 4.06–4.25 (4H, m), 6.09 (1H, s), 6.56 (1H, s). (Found m/z 393.2445. C$_{20}$H$_{35}$N$_3$O$_3$Si requires m/z 393.2448).

Preparation 6

Allyl(2R and 2S)-2-{(3S,4R)-4-[(1,5-diethylpyrazol-3-yl)carbonylmethyl]-3-[(R)-1-tert-butyldimethylsilyloxyethyl]-2-oxoazetidinyl}-2-hydroxyacetate (3S,4R)-4-[(1,5-Diethylpyrazol-3-yl)carbonylmethyl]-3-[(1R)-1-tert-butyldimethylsilyloxyethyl]azetidin-2-one (1.7 g) and allyl glyoxylate hydrate (585 mg) in toluene (50 ml)

were heated under reflux in a Dean and Stark apparatus under an atmosphere of argon for 16 h. The mixture was cooled, diluted with hexane (50 ml) and chromatographed on silica gel, eluting with ethyl acetate/hexane mixtures. This gave the two diastereoisomers of the title compound (together 1.91 g); Isomer 1, δ (CDCl$_3$) 0.064 (6H, s), 0.87 (9H, s), 1.21 (3H, d, J 6.3 Hz), 1.29 (3H, t, J 7.5 Hz), 1.45 (3H, t, J 7.3 Hz), 2.63 (2H, q, J 7.3 Hz), 2.98 (1H, d, J 2.7 & 9.4 Hz), 3.39 (1H, dd, J 9.6 & 18.8 Hz), 3.54 (1H, dd, J 3.1 & 18.3 Hz), 4.0–4.71 (6H, m), 4.97 (1H, d, J 10.7 Hz), 5.13–5.28 (2H, m), 5.54 (1H, d, J 10.7 Hz), 5.72–5.88 (2H, m), 6.57 (1H, s); Isomer 2, δ (CDCl$_3$) 0.036 (3H, s) 0.061 (3H, s), 0.85 (9H, s), 1.20–1.33 (6H, m), 1.45 (3H, t, J 7.3 Hz), 2.63 (2H, q, J 7.5 Hz), 2.98 (1H,dd J 2.5 & 16.3 Hz), 3.31 (1H, dd, J 8.5 & 4.0 Hz), 3.61 (1H, dd, J 3.2 & 16.1 Hz), 4.08–4.26 (4H, m), 4.71 (2H, d, J 5.6 Hz), 4.81 (1H, d, J 8.2 Hz), 5.24–5.39 (2H, m), 5.56 (1H, d, J 8.2 Hz), 5.84–6.00 (1H, m) 6.60 (1H, s).

Preparation 7

Allyl 2-{(3S,4R)-4-[(1,5-diethylpyrazol-3-yl)carbonylmethyl]-3-[(R)-1-tert-butyldimethylsilyloxyethyl]-2-oxoazetidinyl}-2-(tri-n-butylphosphoranylidene)acetate Allyl(2R and 2S)-2-{(3S,4R)-4-[(1,5-diethylpyrazol-3-yl)carbonylmethyl]-3-[(1R)-1-tert-butyldimethylsilyloxyethyl]-2-oxoazetidinyl}-2-hydroxyacetate (1.83 g) in dry THF (50 ml) under argon was cooled to −20° C. and treated with 2,6-lutidine (0.63 ml), followed by thionyl chloride (0.39 ml). The mixture was stirred at −20° C. for 30 minutes, and then allowed to warm to room temperature and filtered, washing the residue with THF. The filtrate was evaporated in vacuo, toluene (20 ml) was added and removed in vacuo and the residual oil was dried in vacuo. The oil was then dissolved in 1,4-dioxan (20 ml) under an argon atmosphere, and treated with tri-n-butylphosphine (1.0 ml). The mixture was stirred for 1 h. 2,6-lutidine (0.50 ml) was then added and the mixture was stirred for a further 10 minutes. The mixture was diluted with ethyl acetate, washed with water, then with brine, and dried (MgSO$_4$). After removal of the ethyl acetate the crude product was chromatographed on silica gel, eluting with ethyl acetate/hexane mixtures to give the phosphorane, $v_{max}$ (CH$_2$Cl$_2$) 1737, 1676, 1605, 1465, 1374, 1090, and 835 cm$^{-1}$.

Preparation 8

Allyl 2-{(3S,4R)-4-[(1,5-diethylpyrazol-3-yl)carbonylmethyl]-3-[(R)-1-hydroxyethyl]-2-oxoazetidinyl}-2-(tri-n-butylphosphoranylidene)acetate The phosphorane prepared above was taken up in 1,4-dioxan (30 ml) and treated with 5M HCl (10 ml). After 30 min the mixture was carefully treated with excess saturated aqueous NaHCO$_3$ followed by saturated brine. The mixture was extracted twice with ethyl acetate, and combined extracts were dried (MgSO$_4$) and evaporated. The residue was chromatographed on silica gel, eluting with ethyl acetate/hexane mixtures to give the hydroxy compound, (1.2 g), $v_{max}$ (CH$_2$Cl$_2$) 3452, 1737, 1666, 1606, 1465, 1374, 1086, and 1047 cm$^{-1}$.

Preparation 9

Allyl(5R,6S)-6-[(1R)-1-hydroxyethyl]-2-(1,5-diethylpyrazol-3-yl)carbapen-2em-3-carboxylate Allyl 2-{(3S,4R)-4-[(1,5-diethylpyrazol-3-yl)carbonylmethyl]-3-[(R)-1-hydroxyethyl]-2-oxoazetidinyl}-2-(tri-n-butylphosphoranylidene) acetate (1.2 g), in toluene (60 ml) containing hydroquinone (20 mg) was heated under reflux in an argon atmosphere for 6.5 h. The mixture was cooled and then loaded onto a column (4×15 cm) of silica gel (particle size 0.040–0.063 mm), eluting with ethyl acetate, followed by ethyl acetate/ethanol (9:1). This gave the carbapenem (406 mg); $v_{max}$ (CH$_2$Cl$_2$) 3604, 3424, 2977, 1773, 1716, 1311, 1186 cm$^{-1}$; δ (CDCl$_3$) 1.29 (t, J 7.4 Hz), 1.36 (d, J 6.3 Hz), 1.40 (t, J 7.3 Hz) (together 9H), 1.86 (1H, d, J 5.0 Hz), 2.62 (2H, q, J ca. 7.4 Hz), 3.19 (1H, dd, J 2.8 & 6.7 Hz), 3.29 (1H, dd, J 9.0 & 18.5 Hz), 3.62 (1H, dd, J 9.9 & 18.5 Hz), 4.08 (2H, q, J 7.2 Hz), 4.16–4.30 (2H, m), 4.68–4.90 (2H, m), 5.27 (1H, m, approx d, J ca. 13 Hz), 5.46 (m, approx d, J ca. 17 Hz), 5.93–6.06 (1H, m), 7.01 (1H, s) ppm; (Found: m/z 359.1840. C$_{19}$H$_{25}$N$_3$O$_4$ requires m/z 359.1485).

Preparation 10

Sodium (5R,6S)-6-[(R)-1-hydroxyethyl]-2-(1,5-diethylpyrazol-3-yl)carbapen-2-em-3-carboxylate Allyl(5R,6S)-6-[(R)-1-hydroxyethyl]-2-(1,5-diethylpyrazol-3-yl)carbapen-2-em-3-carboxylate (267 mg) in dichloromethane (2 ml) and ethyl acetate (2 ml) under argon were treated with sodium 2-ethylhexanoate (135 mg), followed by triphenylphosphine (17.5 mg), followed by tetrakis(triphenylphosphine)palladium(0) (28.3 mg) and the mixture was stirred for 45 min. Diethyl ether (100 ml) was then added, and after stirring for 30 minutes the mixture was centrifuged. The residual solid was washed with diethyl ether, and dried under a stream of argon. The solid was then taken up in a small amount of water and chromatographed on DIAION HP20SS resin, eluting with water, followed by water/THF mixtures; 2%, 3%, 4% and 6% THF. Fractions were monitored by HPLC, and those containing the product were combined, reduced in volume and freeze-dried to give sodium (5R,6S)-6-[(R)-1-hydroxyethyl]-2-(1,5-diethylpyrazol-3-yl)carbapen-2-em-3-carboxylate as a solid (169 mg); $v_{max}$(KBr) 1752, 1593, 1433, 1382, 1288, and 1258 cm$^{-1}$; $\lambda_{max}$(H$_2$O)/nm 298 (ε/dm$^3$ mol$^{-1}$ cm$^{-1}$ 9,031), 260 (sh) (ε5853); δ (D$_2$O) 1.19 (t, J 7.6 Hz), 1.27 (d, J ca. 6.8 Hz), 1.28 (d, J ca. 7.3 Hz) (together 9H), 2.60 (2H, q, J 7.5 Hz), 3.18 (2H, d, J 9.8 Hz), 3.46 (1H, dd, J 2.7 & 5.9 Hz), 4.05 (2H, q, J 7.2 Hz), 4.14–4.26 (2H, m), 6.48 (1H, s) ppm; [Found (electrospray ms) m/z 342 (MH)$^+$].

EXAMPLE 10

Sodium (5R,6S)-6-[(R)-1-hydroxyethyl]-2-(1-ethyl-5-methylpyrazol-3-yl)carbapen-2-em-3-carboxylate Preparation 1

Ethyl 1-ethyl-5-methylpyrazole-3-carboxylate

N-Ethylhydrazine oxalate (12 g) in glacial acetic acid (100 ml) was cooled in an ice-bath and treated with ethyl 2,4-dioxovalerate (11.24 ml). After addition was complete the mixture was stirred at room temperature; after ca. 45 min the mixture was warmed to dissolve insoluble ethylhydrazine oxalate. The mixture was stirred for a further 2 h and then poured into water(ca. 300 ml)/ethyl acetate (ca. 700 ml) and solid $K_2CO_3$ was carefully added, with stirring, until the pH was neutral. After separation the aqueous layer was re-extracted with ethyl acetate. The combined ethyl acetate extracts were dried ($MgSO_4$), and the solvents removed to leave an oil. Chromatography on silica gel, loading in $CH_2Cl_2$/hexane and eluting with a gradient elution of ethyl acetate/hexane mixtures (from 2:8 to 1:1) gave ethyl 1-ethyl-5-methylpyrazole-3-carboxylate as an oil (13.2 g); $v_{max}$ ($CH_2Cl_2$) 1717, 1446, 1389, and 1219 cm$^{-1}$; δ ($CDCl_3$) 1.38 (3H, t, J 7.2 Hz), 1.42 (3H, t, J 7.3 Hz), 2.30 (3H, s), 4.17 (2H, q, J7.3 Hz), 4.38 (2H, q, J7.1 Hz), 6.55 (1H, s); (Found m/z 182.1055. $C_9H_{14}N_2O_2$ requires m/z 182.1055).

Preparation 2

1-Ethyl-5-methylpyrazole-3-carboxylic acid

Ethyl 1-ethyl-5-methylpyrazole-3-carboxylate (10.93 g) in ethanol (70 ml) was treated with KOH (3.69 g), followed by water (30 ml), and the mixture was stirred and heated under reflux for 6 h. The ethanol was removed using a rotary evaporator and ethyl acetate/water were added. The pH of the mixture was adjusted to 3.0 and the layers were separated. The aqueous layer was re-extracted with ethyl acetate. The combined ethyl acetate layers were extracted with excess aqueous $NaHCO_3$. The $NaHCO_3$ extract was poured into excess acid, and the pH was then adjusted to 3, and NaCl was added to the solution. The mixture was then repeatedly extracted with ethyl acetate, and the combined extracts were dried ($MgSO_4$) and evaporated. The residue was triturated with diethyl ether to give the acid as a solid (5.65 g); $v_x$ ($CH_2Cl_2$) 2754, 2598, 1698, 1498, 1464, 1387, and 1233 cm$^{-1}$; δ ($CDCl_3$) 1.40 (3H, t, J 7.3 Hz), 2.32 (3H,s), 4.19 (2H, q, J 7.3 Hz), 6.61 (1H,s) ppm; (Found m/z 154.0740. $C_7H_{10}N_2O_2$ requires m/z 54.0742).

Preparation 3

N-Methoxy-N-methyl-1-ethyl-5-methylpyrazole-3-carboxamide

1-Ethyl-5-methylpyrazole-3-carboxylic acid (5.25 g) in dry dichloromethane (100 ml) containing N,N-dimethylformamide (0.26 ml) was cooled in an ice-bath and treated with a solution of oxalyl chloride (3.27 ml) in dichloromethane (25 ml), added dropwise. The mixture was stirred in the cold for 25 min, and then allowed to warm to room temperature, when evolution of a gas was observed. After 10 min the solvent was removed by evaporation in vacuo and toluene was added and removed (x 2) to ensure any residual HCl and oxalyl chloride had been removed. The resultant acid chloride was redissolved in dry dichloromethane and then treated with N,O-dimethylhydroxylamine hydrochloride (3.61 g). The mixture was cooled in an ice-bath and treated with pyridine (6.0 ml). the mixture was then allowed to stir at room temperature for 1.5 h and then diluted with ether (100 ml) and washed with brine. The organic layer was then dried ($MgSO_4$) and evaporated to leave an oil. This was the chromatographed on silica gel, loading in dichloromethane, and eluting with ethyl acetate/hexane mixtures to give, after evaporation of requisite fractions, the hydroxamate (5.2 g) as a solid;

$v_{max}$($CH_2Cl_2$) 2982, 2937, 1641, 1489, 1445, 1379, and 975 cm$^{-1}$; δ ($CDCl_3$) 1.43 (3H, t, J 7.3 Hz), 2.29 (3H, s), 3.42 (3H, s), 3.76 (3H, s,), 4.13 (2H, q, J 7.3 Hz), 6.49 (1H, s); (Found m/z 197.1164. $C_9H_{15}N_3O_2$ requires m/z 197.1164).

Preparation 4

3-Acetyl-1-ethyl-5-methylpyrazole

N-Methoxy-N-methyl-1-ethyl-5-methylpyrazole-3-carboxamide (3.12 g) in dry tetrahydrofuran (60 ml) was cooled in an ice-bath and treated with a 3.0M solution of methylmagnesium bromide in ether (11.08 ml). After stirring for 1.5 h the mixture was poured into a mixture of methanol (100 ml) and 5M aqueous HCl (10 ml) in an ice-bath. The mixture was then evaporated to lower volume and treated with a mixture of dichloromethane, water and saturated brine. After separation the aqueous layer was re-extracted with dichloromethane. The combined dichloromethane extracts were dried ($MgSO_4$) and evaporated to leave an oil (2.26 g), which solidified on standing; $v_{max}$ ($CH_2Cl_2$) 1680, 1446, 1425, 1380, 1324, 1208, and 945 cm$^{-1}$; δ ($CDCl_3$) 1.44 (3H, t, J 7.3 Hz), 2.30 (3H, s), 2.53 (3H, s), 4.13 (2H, q, J 7.3 Hz,), 6.51 (1H,s); (Found: m/z 152.0949. $C_8H_{12}N_2O$ requires m/z 152.090).

Preparation 5

(3S,4R)-4-[(1-ethyl-5-methylpyrazol-3-yl)carbonylmethyl]-3-[(R)-1-tert-butyldimethylsilyloxyethly] azetidin-2-one 3-Acetyl-1-ethyl-5-methylpyrazole (3.51 g) in dry tetrahydrofuran (THF) (150 ml) under an argon atmosphere was cooled in an acetone/solid carbon dioxide bath and then treated with a 1M solution of lithium bis(trimethylsilyl)amide (50 ml). The mixture was stirred for 45 minutes and then (3R,4R)-4-acetoxy-3-[(1R)-1-tert-butyldimethylsilyloxyethyl]azetidinone (6.6 g) was added as a solid under a blanket of argon. The mixture was stirred in the cold for 3.5 h. Saturated aqueous ammonium chloride was then added, followed by ethyl acetate, and the mixture was allowed to warm to room temperature. A little water was added and the layers were separated and the aqueous layer was re-extracted with ethyl acetate. The combined ethyl acetate extracts were washed with saturated brine, dried and evaporated. Chromatography on silica gel, eluting with ethyl acetate/hexane mixtures gave the title compound (3.65 g), $v_{max}$ ($CH_2Cl_2$) 3411, 1761, 1678, 1376, 1151, and 838 cm$^{-1}$; δ ($CDCl_3$) 0.064 (6H, s), 0.86 (9H, s), 1.20 (3H,d, J 6.3 Hz), 1.44 (3H, t, J 7.3 Hz), 2.31 (3H, s), 2.89 (1H, dd, J 1.8 & 4.9 Hz), 3.15 (1H, dd, J 10.0 & 17.1 Hz), 3.50 (1H, dd, J 3.5 & 17.0 Hz), 4.06–4.25 (4H, m), 6.11 (1H, s) 6.53 (1H, s). (Found m/z 379.2296. $C_{19}H_{33}N_3O_3Si$ requires m/z 379.2291).

Preparation 6

Allyl(2R and 2S)-2-{(3S,4R)-4-[(1-ethyl-5-methylpyrazol-3-yl)carbonylmethyl]-3-[(R)-1-tert-butyldimethylsilyloxyethyl]-2-oxoazetidinyl}-2-hydroxyacetate (3S,4R)-4-[(1-Ethyl-5-methylpyrazol-3-yl)carbonylmethyl]-3-[(R)-1-tert-butyldimethylsilylozyethyl]azetidin-2-one (3.6 g) and allyl glyoxylate hydrate (1.66 g) in toluene (100 ml) were heated under reflux in a Dean and Stark apparatus under an atmosphere of argon for 3.5 h. T.l.c. of the reaction mixture showed the reaction had almost prceeded to completion, so more allyl glyoxylate hydrate (190 mg) was added and the mixture was heated under reflux for a further 45 min. The mixture was cooled, the toluene was removed to give crude allyl (2R and 2S)-2-{(3S,4R)-4-[(1-ethyl-5-methylpyrazol-3-yl)carbonylmethyl]-3-[(R)-

1-tert-butyldimethylsilyloxyethyl]-2-oxoazetidinyl}-2-hydroxyacetate, which was used in the next stage: $v_{max}$ (CH$_2$Cl$_2$) 3681, 3518, 1758, 1676, 1448, 1376, 1326, 1209, 1148, 1092, 954, and 836 cm$^{-1}$; δ (CDCl$_3$) inter alia 0.035 (s), 0.061 (s) (together 6H,), 0.858 (s), 0.865 (s) (together 9H), 1.21 (d, J 6.2 Hz), 1.24 (d, J 6.2 Hz), (together 3H), 1.44 (3H, t, J 7.2 Hz), 2.31 (3H, s), 2.95–3.00 (1H, m), 3.25–3.64 (2H, m), 6.53 (s), 6.56 (s) ppm.

Preparation 7

Allyl 2-{(3S,4R)-4-[(1-ethyl-5-methylpyrazol-3-yl)carbonylmethyl]-3-[(R)-1-tert-butyldimethylsilyloxyethyl]-2-oxoazetidinyl}-2-(tri-n-butylphosphoranylidene)acetate Allyl(2R and 2S)-2-{(3S,4R)-4-[(1-ethyl-5-methylpyrazol-3-yl)carbonylmethyl]-3-[(R)-1-tert-burydimethylsilyloxyethyl]-2-oxoazetidinyl}-2-hydroxyacetate (crude from the above preparation) in dry THF (125 ml) under argon was cooled to −20° C. and treated with 2,6-lutidine (1.98 ml), followed by thionyl chloride (1.24 ml). The mixture was stirred at −20° C. for 30 minutes, and then allowed to warm to room temperature and filtered, washing the residue with THF (20 ml). The flitrate was evaporated in vacuo, toluene (70 ml) was added and removed in vacuo and the residual oil was dried in vacuo. The oil was then taken up in 1,4-dioxan (40 ml) under an argon atmosphere, and treated with tri-n-butylphosphine (3.11 ml). The mixture was stirred for 1 h. 2,6-Lutidine (1.59 ml) was then added and the mixture was stirred for a further 30 minutes. The mixture was diluted with ethyl acetate, washed with water, then with brine, and dried (MgSO$_4$). After removal of the ethyl acetate the crude product was chromatographed on silica gel, eluting with ethyl acetate/hexane mixtures to give the phosphorane, which was used in the next stage.

Preparation 8

Allyl 2-{(3S,4R)-4-[(1-ethyl-5-methylpyrazol-3-yl)carbonylmethyl]-3-[(R)-1-hydroxyethyl]-2-oxoazetidinyl}-2-(tri-n-butylphosphoranylidene)acetate The phosphorane prepared above was taken up in 1,4-dioxan (60 ml) and treated with 5M HCl (20 ml). After 1 h the mixture was carefully treated with ca. 40 ml saturated aoueous NaHCO$_3$, followed by solid NaHCO$_3$ until the pH was slightly alkaline. Saturated brine was added and the mixture was extracted twice with ethyl acetate. The combined extracts were dried (MgSO$_4$) and evaporated. The residue was chromatographed on silica gel, eluting with ethyl acetate/hexane mixtures to give the hydroxy compound, (2.60 g), $v_{max}$ (CH$_2$Cl$_2$) 3454, 1741, 1667, 1606, 1448, 1403, 1379, 1155, 1087, 953, and 811 cm$^{-1}$.

Preparation 9

Allyl(5R,6S)-6-[(R)-1-hydroxyethyl]-2-(1-ethyl-5-methylpyrazol-3-yl)carbapen-2-em-3-carboxylate Allyl 2-{(3S,4R)-4-[(1-ethyl-5-methylpyrazol-3-yl)carbonylmethyl]-3-[(R)-1-hydroxyethyl]-2-oxoazetidinyl}-2-(tri-n-butylphosphoranylidene)acetate (2.6 g), in toluene (120 ml) containing hydroquinone (20 mg) was heated under reflux in an argon atmosphere for 4 h, allowed to stand for 64 h, and then heated under reflux for a further 2 h. The mixture was cooled and then loaded onto a column (4.5×12 cm) of silica gel (particle size 0.040–0.063 mm), eluting with ethyl acetate/hexane mixtures; 1:1; 6:4; 7:3; 8:2; 9:1 (250 ml of each), followed by ethyl acetate. This gave the carbapenem (436 mg); $v_{max}$(CH$_2$Cl$_2$) 3604, 2976, 1774, 1716, 1600, 1546, 1311, 1189 cm$^{-1}$; $\lambda_{max}$(EtOH)/nm 321.5 (ε/dm$^3$ mol$^{-1}$ cm$^{-1}$ 14,856), δ (CDCl$_3$) 1.36 (d, J 6.3 Hz), 1.39 (t, J 7.3 Hz) (together 5H), 1.80 (1H, d, J 5.0 Hz), 2.28 (3H,s), 3.19 (1H, dd J 2.7 & 6.7 Hz), 3.28 (1H, dd, J 9.0 & 18.6 Hz 3.60 (1H, dd, J 9.9 & 18.5 Hz), 4.08 (2H, q, J 7.3 Hz), 4.16–4.30 (2H, m), 4.68–4.90 (2H, m), 5.27 (1H, m, approx d, J ca. 12 Hz), 5.46 (m, approx d, J ca. 17 Hz), 5.93–6.08 (1H, m), 7.00 (1H, s) ppm; [Found m/z 345.1693. C$_{18}$H$_{23}$N$_3$O$_4$ requires m/z 345.1689].

Preparation 10

Sodium (5R,6S)-6-[(R)-1-hydroxyethyl]-2-(1-ethyl-5-methyl-pyrazol-3-yl)carbapen-2-em-3-carboxyliate Allyl(5R,6S)-6-[(R)-1-hydroxyethyl]-2-(1-ethyl-5-methylpyrazol-3-yl)carbapen-2-em-3-carboxylate (267 mg) in dichloromethane (3 ml) and ethyl acetate (3 ml) under argon was treated with sodium 2-ethylhexanoate (183 mg), followed by triphenylphosphine (24 mg), followed by tetrakis (triphenylphosphine)palladium(0) (35 mg) and the mixture was stirred for 45 min. Diethyl ether (100 ml) was then added, and after stirring for 90 minutes, the mixture was centrifuged. The residual solid was dried under a stream of argon, and then in a desiccator. The solid was then taken up in water containing sodium chloride and chromatographed on DIAION HP20SS resin, eluting with water, followed by water/THF mixtures; 1%, 2%, and 3%, THF. Fractions were monitored by HPLC, and those containing the product were combined, reduced in volume and freeze-dried to give sodium (5R,6S)-6-[(R)-1-hydroxyethyl]-2-(1-ethyl-5-methylpyrazol-3-yl)carbapen-2-em-3-carboxylate as a solid (168 mg); $v_{max}$(KBr) 1761, 1608, 1577, 1381, 1225 cm$^{-1}$; $\lambda_{max}$(H$_2$O)/nm 298 (ε/dm$^3$ mol$^{-1}$ cm$^{-1}$ 8,531); δ (D$_2$O) 1.26 (d, J ca. 6 Hz), 1.27 (d, J ca. 7 Hz) (together 5H), 2.23 (3H, s), 3.17 (2H, approx d, J ca. 9 Hz), 3.44 (1H, dd, J 2.9 & 6.0 Hz), 4.04 (2H, q, J 7.3 Hz), 4.15–4.25 (2H, m), 6.41 (1H, s) ppm.

EXAMPLE 11

Sodium (5R,6S)-6-[(R)-1-hydroxyethyl]-2-[1-(2-hydroxyethyl)-5-methylpyrazol-3-yl]carbapen-2-em-3-carboxylate

Preparation 1

Ethyl 1-(2-hydroxyethyl)-5-methylpyrazole-3-carboxylate

The title compound was prepared from hydroxyethyl hydrazine (3.64 g, 50 mM) and ethyl 2,4-dioxovalerate (8.5 g, 50 mM) as described in Example 1 Preparation 1 as a colourless oil (9.39 g, 95%); $v_{max}$ (CH$_2$Cl$_2$) 1700 cm$^{-1}$; $\delta_H$(CDCl$_3$) 1.39 (3H, t, J7 Hz), 2.40 (3H, s), 2.98 (2H, t, J7 Hz), 4.33–4.48 (4H,m), and 6.39 (1H, s); E.I m/e 198 (95%).

Preparation 2

Ethyl 1-(2-t-butyldimethylsilyloxyethyl)-5-methylpyrazole-3-carboxylate

Ethyl 1-(2-hydroxyethyl)-5-methylpyrazole-3-carboxylate (9.39 g, 47.4 mM) in dichloromethane (150 ml) was cooled to below 0° C. and treated with triethylamine (7.19 ml, 52 mM) followed by t-butyldimethylsilyl chloride (7.85 g, 52 mM). The mixture was stirred at room temperature for 3 days. The reaction mixture was washed with brine, dried (MgSO$_4$) and evaporated. Purification on silica geleluting with 50% ethyl acetate in hexane gave the title compound as a pale yellow solid in quantitative yield; $v_{max}$ (film) 1719, 1472 and 1388 cm$^{-1}$; $\delta_H$(CDCl$_3$) −0.08 (6H, s), 0.81 (9H, s), 1.38 (3H, t, J7 Hz), 2.33 (3H, s), 3.98 (2H, t, J5 Hz), 4.21 (2H, t, J5 Hz), 4.39 (2H, q, J7 Hz), and 6.53 (1H, s); NH$_3$DCI m/e 313 (100%).

Preparation 3

1-(2-t-Butyldimethylsilyloxyethyl)-5-methylpyrazole-3-carboxylic acid

The title compound was prepared from ethyl 1-(2-t-butyldimethylsilyloxyethyl)-5-methylpyrazole-3-carboxylate (16.08 g, 51.5 mM) as described in Example 4 Preparation 2 as a white solid (10.5 g, 72%); $v_{max}$(KBr) 1688, 1648, 1533 and 1505 cm$^{-1}$; $\delta_H$(CDCl$_3$) −0.10 (6H, s), 0.81 (9H, s), 2.35 (3H, s), 4.00 (2H, t, J5 Hz), 4.24 (2H, t, J5 Hz), 6.60 (1H, s); NH$_3$DCI m/e 285 (100%).

Preparation 4

3-Acetyl-1-(2-t-butyldimethylsilyloxyethyl)-5-methylpyrazole 1-(2-t-Butyldimethylsilyloxyethyl)-5-methylpyrazole-3-carboxylic acid (5.6 g, 19.7 mM) in diethyl ether (100 ml) was cooled to between 0° and 5° C. Triethylamine (3.3 ml, 23.6 mM) was added followed by isobutylchloroformate (2.8 ml, 21.7 mM). The mixture was stirred with cooling for 0.5 h then filtered. Dimethylhydroxylamine hydrochloride 3.84 g, 39.4 mM) was treated with 10% sodium hydroxide solution and stirred for 15 minutes. The mixture was then extracted twice with dichloromethane and the extracts dried (MgSO$_4$). The solution was added to that containing the mixed anhydride and stirred for 2 h. The reaction mixture was was washed with brine. dried (MgSO$_4$) and evaporated. Purification on silica gel eluting with ethyl acetate gave 1-(2-t-butyldimethylsilyloxyethyl)-5-methylpyrazol-3-yl-(N-methoxy-N-methyl)carboxamide as a colourless oil (1.87 g, 29%); $v_{max}$ (CH$_2$Cl$_2$) 1721, 1703, and 1640 cm$^{-1}$; NH$_3$DCI m/e 328 (100%).

1-(2-t-Butyldimethylsilyloxyethyl)-5-methylpyrazol-3-yl-(N-methoxy-N-methyl)carboxamide (1.87 g, 5.7 mM) in THF (50 ml) was cooled to −10° C. and treated with 3M methylmagnesium bromide solution (4.0 ml, 12 mM). The mixture was stirred at 0° C. for 1.5 h, therin treated with ice cold 5% hydrochloric acid in methanol (30 ml). The mixture was evaporated to remove methanol then extracted with dichloromethane. The extracts were washed with brine, dried (MgSO$_4$) and evaporated to give the title compound as an oil (1.61 g, 100%); $v_{max}$ (CH$_2$Cl$_2$) 1681 and 1422 cm$^{-1}$; $\delta_H$(CDCl$_3$) −0.10 (6H, s), 0.80 (9H, s), 2.33 (3H, d, J0.7 Hz), 2.54 (3H, s), 4.00 (2H, t, J5 Hz), 4.19 (2H, t, J5 Hz), and 6.50 (1H, s); NH$_3$DCI m/e 283 (100%).

Preparation 5

(3S,4R)-[(R)-1-t-Butyldimethylsilyloxyethyl]-4-{[1-(2-t-butyldimethylsilyloxyethyl)-5-methylpyrazol-3-ylcarbonyl]methyl}azetidin-2-one 3-Acetyl-1-(2-t-butyldimethylsilyloxyethyl)-5-methylpyrazole (1.42 g, 5.04 mM) was reacted as described in Example 4 Preparation 5 to give the title compound as a white solid (1.02 g, 80%); $v_{max}$ (KBr) 1736 and 1679 cm$^{-1}$; $\delta_H$(CDCl$_3$) −0.01 (6H, s), 0.07 (6H,s), 0.81 (9H,s), 0.87 (9H, s), 1.22 (3H, d, J6 Hz), 2.33 (3H, s), 2.88–2.93 (1H, m), 3.13 (1H, dd, J 10, 17 Hz), 3.50 (1H, dd, J 3.5,17 Hz), 3.94–4.26 (6H, m), 6.08 (1H, s), and 6.51 (1H, s); m/e 509.3099 (C$_{25}$H$_{47}$N$_3$O$_4$Si$_2$ requires 509.3105).

Preparation 6

Allyl{(3S,4R)-[(R)-1-t-butyldimethylsilyloxyethyl]-4-{[1-(2-t-butyldimethylsilyloxyethyl)-5-methylpyrazol-3-ylcarbonyl]methyl}-2-oxoazetidin-1-yl}tributylphosphoranylidene acetate The title compound was prepared from (3S,4R)-[(R)-1-t-butyldimethylsilyloxyethyl]-4-{[1-(2-t-butyldimethylsilyloxyethyl)-5-methylpyrazol-3-ylcarbonyl]methyl}azetidin-2-one (1.02 g, 2.0 mM) as described in Example 4, Preparation 6 as a yellow oil (1.05 g, 65%); $v_{max}$(CH$_2$Cl$_2$) 1736, 1678, and 1605 cm$^{-1}$ Preparation 7

Allyl{(5R,6S)-6-[(R)-1-hydroxyethyl]-2-[1-(2-hydroxyethyl)-5-methylpyrazol-3-yl]}carbapen-2-em-3-carboxylate The title compound was prepared from allyl{(3S,4R)-[(R)-1-t-butyldimethylsilyloxyethyl]-4-{[1-(2-t-butyldimethylsilyloxyethyl)-5-methylpyrazol-3-ylcarbonyl]methyl}-2-oxoazetidin-1-yl}tributylphosphoranylidene acetate as described in Example 4, Preparation 7 to give a yellow oil (0.246 g, 52%) $v_{max}$(CH$_2$Cl$_2$) 1774 cm$^{-1}$; $\delta_H$(CDCl$_3$) 1.36 (3H, d, J6 Hz), 2.29 (3H, s), 3.18–3.40 (2H, m), 3.48–3.70 (1H, m), 3.95–4.40 (6H, m), 4.67–4.95 (2H, m), 5.21–5.54 (2H, m), 5.90–6.10 (1H, m), and 7.00 (1H, s); NH$_3$DCI m/e 362 (70%).

Preparation 8

Sodium {(5R,6S)-6-[(R)-1-hydroxyethyl]-2-[1-(2-hydroxyethyl)-5-methylpyrazol-3-yl]}carbapen-2-em-3-carboxylate The title compound was prepared from allyl{(5R,6S)-6-[(R)-1-hydroxyethyl]-2-[1-(2-hydroxyethyl)-5-methylpyrazol-3-yl]}carbapen-2-em-3-carboxylate (0.246 g, 0.68 mM) as described in Example 4, Preparation 8 as a pale yellow lyophylised solid (0.05 g, 21%); $\lambda_{max}$ (H$_2$O) 297 (e 8223); $v_{max}$(KBr) 1752, 1590, and 1389 cm$^{-1}$; $\delta_H$ (D$_2$O) 1.31 (3H, d, J6.5 Hz), 2.29 (3H, s), 3.13–3.30 (2H, m), 3.42–3.56 (1H, m), 3.88 (2H, t, J5 Hz), 4.18 (2H, t, J5 Hz), 4.05–4.30 (2H, m), and 6.45 (1H, s); m/e 344 (MH$^+$).

EXAMPLE 12

Sodium {(5R,6S)-6-[(R)-1-hydroxyethyl]-2-[1-(2-methoxyethyl)-5-methylpyrazol-3-yl]}carbapen-2-em-3-carboxylate Preparation 1

3-Acetyl-1-(2-hydroxyethyl)-5-methylpyrazole

3-Acetyl-1-(2-t-butyldimethylsilyloxyethyl)-5-methylpyrazole (1.6 g, 5.7 mM) in methanol (50 ml) was treated with 2M hydrochloric acid (10 ml). After stirring for 0.5 h the mixture was evaporated to remove methanol and the residual oil extracted repeatedly with dichloromethane and ethyl acetate to give the title compound as a colouless oil (0.633 g, 66%); $\delta_H$(CDCl$_3$) 2.30 (3H, s), 2.48 (3H, s), 3.98–4.09 (2H, m), 4.12–4.21 (2H, m), and 6.49 (1H, s).

Preparation 2

3-Acetyl-1-(2-methoxyethyl)-5-methylpyrazole

3-Acetyl-1-(2-hydroxyethyl)-5-methylpyrazole (0.63 g, 3.77 mM) in ethylene glycol dimethyl ether (10 ml) was treated with silver oxide (0.87 g, 3.77 mM) and methyl iodide (0.28 ml, 4.5mM). Sodium hydride (0.17 g 60% dispersion in oil, 4.14 mM) was added and the mixture stirred for 2 h, then filtered through celite and evaporated. Purification on silica gel eluting with ethyl acetate gave the title compound (0.157 g, 22%); $v_{max}$ 1681 cm$^{-1}$; $\delta_H$(CDCl$_3$) 2.32 (3H, s), 2.50 (3H, s), 3.30 (3H, s), 3.78 (2H, t, J5.4 Hz), 4.25 (2H, t, J5.4 Hz), and 6.51 (1H, s); EI m/e 182 (65%).

Preparation 3

(3S,4R)-[(R)-1-t-Butyldimethylsilyloxyethyl]-4-{[1-(2-methoxyethyl)-5-methylpyrazol-3-ylcarbonyl] methyl}azetidin-2-one 3-Acetyl-1-(2-methoxyethyl)-5-methylpyrazole (0.67 g, 3.73 mM) was reacted as described in Example 4 Preparation 5 to give the title compound as a white solid (0.58 g, 76%); $v_{max}$ (KBr) 1761 and 1679 cm$^{-1}$; $\delta_H$(CDCl$_3$) 0.07 (6H,s), 0.87 (9H,s), 1.21 (3H, d, J6 Hz) 2.33 (3H, s), 2.89 (1H, m), 3.12, 3.19 (1H, 2d, J 10 Hz), 3.48 (1H,dd, J 3.5,17 Hz) 3.76 (2H, t, J5 Hz), 4.03–4.28 (4H, m), 6.12 (1H, s), and 6.52 (1H, s); NH$_3$DCI m/e 410 (100%).

Preparation 4

Allyl{(3S,4R)-[(R)-1-t-butyldimethylsilyloxyethyl]-4-{[1-(2-methoxyethyl)-5-methylpyrazol-3-ylcarbonyl]methyl}-2-oxoazetidin-1-yl}tributylphosphoranylidene acetate The title compound was prepared from (3S,4R)-[(R)-1-t-butyldimethylsilyloxyethyl]-4-{[1-(2-methoxyethyl)-5-methylpyrazol-3-ylcarbonyl]methyl}azetidin-2-one (1.02 g, 2.0 mM) as described in Example 4 Preparation 5 as a yellow oil (0.51 g, 49%); $v_{max}$(CH$_2$Cl$_2$) 1739, 1678, and 1605 cm$^{-1}$.

Preparation 5

Allyl{(5R,6S)-6-[(R)-1-hydroxyethyl]-2-[1-(2-methoxyethyl)-5-methylpyrazol-3-yl}carbapen-2-em-3-carbolate The title compound was prepared from allyl{(3S,4R)-[(R)-1-t-butyldimethylsilyloxyethyl]-4-{[1-(2-methoxyethyl)-5-methylpyrazol-3-ylcarbonyl]methyl}-2-oxoazetidin-1-yl}tributylphosphoranylidene acetate as described in Example 4 Preparation 6 to give a yellow oil (0.83 g, 26%); $v_{max}$(CH$_2$Cl$_2$) 1773, 1720 cm$^-$; $\delta_H$(CDCl$_3$) 1.36 (3H, d, J6 Hz), 2.30 (3H, s), 3.14–3.23 (1H, m), 3.30 (4H, m), 3.59(1H, dd, J10, 19 Hz) 3.72 (2H, t, J5.5 Hz), 4.13–4.40 (4H, m), 4.60–4.91 (2H, m), 5.24–5.50 (2H, m), 5.78–6.09 (1H, m), and 6.99 (1H, s); m/e 375.1793 (C$_{19}$H$_{25}$N$_3$O$_5$ requires 375.1794).

Preparation 6

Sodium {(5R,6S)-6-[(R)-1-hydroxyethyl]-2-[1-(2-methoxyethyl)-5-methylpyrazol-3-yl]}carbapen-2-em-3-carboxylate The title compound was prepared from allyl{(5R,6S)-6-[(R)-1-hydroxyethyl]-2-[1-(2-methoxyethyl)-5-methylpyrazol-3-yl]}carbapen-2-em-3-carboxylate (0.83 g, 0.22 mM) as described in Example 4 Preparation7 as a pale yellow lyophilised solid (0.037 g, 47%); $\lambda_{max}$ (H$_2$O) 297.5 nm (e 5931); $v_{max}$(KBr) 1750 and 1701 cm$^{-1}$; $\delta_H$(D$_2$O) 1.29 (3H, d, J6.5 Hz), 2.26 (3H, s), 3.28 (5H, m), 3.44–3.50 (1H, m), 3.78 (2H, t, J5 Hz), 4.05–4.38 (4H, m), and 6.43 (1H, s); m/e 336 (MH$^+$).

EXAMPLE 13

Sodium (5R,6S)-6-[(R)-1-hydroxyethyl]-2-(5-benzyl-1-methylpyrazol-3-yl)carbapen-2-em-3-carboxylate Preparation 1

4-Benzyl-3-methyl-1,2,3-oxadiazol-5-one

N-Methyl-L-phenylalamne (2.50 g) was suspended in water (25 ml) and conc. HCl (1 ml) was addded, with stirring. The solution was cooled to 5° C. and solid sodium nitrite (1.35 g) was added to the stirred solution. After stirring at 5° C. for 1 h, the reaction mixture was partitioned between dichloromethane and water. The organic solution was washed with brine and dried (MgSO$_4$). After filtration the solvent was evaporated to yield N-nitro-N-methyl-L-phenylalanine as a white solid.

The above solid was dissolved in diethyl ether (250 ml) and stirred at room temperature for 16 h with trifluoroacetic anhydride (1.95 ml). The solvent was evaported at reduced pressure and the residue was partitioned between ethyl acetate and saturated NaHCO$_3$ solution. The organic layer was washed with brine, dried (MgSO$_4$) and evaporated to yield the product as a white solid (0.610 g); $d_H$ (CDCl$_3$) 3.81 (3H, s), 3.90 (2H, s), 7.15–7.45 (5H, m).

Preparation 2

5-Benzyl-1-methyl-3-(tri-n-butylstannyl)pyrazole

4-Benzyl-3-methyl-1,2,3-oxadiazol-5-one (0.600 g) and ethynyltri-n-butyltin (2.5 ml) were dissolved in xylene (10 ml) and heated to 140° C. under argon for 16 h. The solvent was then evaporated and the residue was chromatographed over silica gel. Elution with a gradient of 0 to 10% acetone/toluene gave the product as a yellow oil (0.189 g); $d_H$ (CDCl$_3$) 0.8–1.7 (27H, m), 3.77 (3H, s), 4.00 (2H, s), 6.09 (1H, s), 7.10–7.40 (5H, m).

Preparation 3 p-Nitrobenzyl (5R,6S)-6-[(R)-1-hydroxyethyl]-2-(5-benzyl-1-methylpyrazol-3-yl)carbapen-2-em-3-carboxylate The title compound was prepared by the reaction of the stannane from Preparation 2 with p-nitrobenzyl (3R,5R,6S)-6-[(R)-1-hydroxyethyl]-2-oxocarbapenam-3-carboxylate according to the procedure of Example 2, Preparation 1. Silica gel column chromatography, eluting with acetone-toluene mixtures gave the pure product as a white solid (8% yield); $u_{max}$ (CH$_2$Cl$_2$) 3603, 1773, 1720, 1603cm$^{-1}$; $d_H$ (CDCl$_3$) 1.39 (3H, d, J 6.3 Hz), 1.78 (1H, d, J 4.9 Hz), 3.25 (1H, dd, J 2.8, 6.5 Hz), 3.32 (1H, dd, J 9.0 and 18.7 Hz), 3.58–3.75 (4H, dd+s, J 9.7 and 18.6 Hz), 3.99 (2H, s), 4.15–4.38 (2H, m), 5.28 (1H, d, J 13.8 Hz), 5.53 (1H, d, J 3.8 Hz), 7.05–7.4 (6H, m), 7.68 (2H, d, J 8.8 Hz), 8.21 (2H, d, J 8.8 Hz); m/z 502.1863 (M$^+$), calculated for C$_{27}$H$_{26}$N$_4$O$_6$ 502.1852.

Preparation 4

Sodium (5R,6S)-6-[(R)-1-hydroxyethyl]-2-(5-benzyl-1-methylpyrazol-3-yl)carbapen-2-em-3-carboxylate The title compound was prepared from p-nitrobenzyl (5R,6S)-6-[(R)-1-hydroxyethyl]-2-(5-benzyl-1-methylpyrazol-3-yl)carbapen-2-em-3-carboxylate by the procedure described in Example 5, Preparation 5; l$_{max}$ (H$_2$O) 297 nm (e$_m$ 6660); u$_{max}$ (KBr) 3423 (broad), 1750, 1605 cm$^{-1}$; d$_H$ (D$_2$O) 1.39 (3H, d, J 6.3 Hz), 3.22–3.38 (2H, 2×dd, J 8.6, 9.6, 17 Hz), 3.58 (1H, dd, J 2.8, 5.9 Hz), 3.76 (3H, s), 4.15 (2H, s), 4.28–4.39 (2H, m), 6.63 (1H, s), 7.31–7.52 (5H, m).

EXAMPLE 14

Sodium (5R,6S)-6-[(R)-1-hydroxyethyl]-2-{5-methyl-1-[2-(1-methyl-tetrazol-5-ylthio)ethyl]pyrazol-3-yl}carbapen-2-em-3-carboxylate Preparation 1

3-Acetyl-5-methyl-1-[2-(1-methyltetrazol-5-ylthio)ethyl]pyrazole

3-Acetyl-5-methyl-1-(2-hydroxyethyl)pyrazole (1.74 g), triphenyl-phosphine (4.071 g) and 5-mercapto-1-methyltetrazole (3.605 g) were dissolved in dry THF (125 ml) and cooled to 5° C. under an atmosphere of argon. A solution of diethylazodicarboxylate (2.70 g) in THF (25 ml) was added dropwise to the stirred, cooled solution. Stirring was continued at 5° C. for 4 h. The reaction mixture was then partitioned between ethyl acetate and water. The organic solution was washed with NaHCO$_3$ solution, brine, dried (MgSO$_4$) and evaporated. Silica gel column chromatography provided the title compound (1.25 g), u$_{max}$ (CH$_2$Cl$_2$) 1683 cm$^{-1}$; d$_H$ (CDCl$_3$) 2.30 (3H, s), 2.55 (3H, s), 3.80 (2H, t), 3.92 (3H, s), 4.59 (2H, t), 6.51 (1H, s); m/z 266.0953 (M$^+$), calculated for C$_{10}$H$_{14}$N$_6$OS 266.0950.

Preparation 2

(3S,4R) 3-[(R)-1-t-Butyldimethylsilyloxyethyl]-4-{(5-methyl-1-[2-(1-methyltetrazol-5-ylthio)ethyl]pyrazol-3-ylcarbonyl)methyl}azetidin-2-one The title compound was prepared from 4-acetoxy-3-[(R)-1-t-butyldimethylsilyloxyethyl]azetidin-2-one and the product from Preparation 1 according to the procedure of Example 1, Preparation 3; u$_{max}$ (CH$_2$Cl$_2$) 3410, 1761, 1682 cm$^{-1}$, d$_H$ (CDCl$_3$) 0.09 (6H, s), 0.88 (9H, s), 1.27 (3H, d, J 6.2 Hz), 2.34 (3H, s), 2.90 (1H, dd), 3.15 (1H, dd, J 10.0 and 17.1 Hz), 3.48 (1H, dd, J 2.5 and 17.1 Hz), 3.75–3.84 (2H, m), 3.93 (3H, s), 4.054.29 (2H, m), 4.60 (2H, t), 6.10 (1H, s), 6.57 (1H, s); m/z 493.2290 (M$^+$), calculated for C$_{21}$H$_{35}$N$_7$O$_3$SSi 493.2291.

Preparation 3

Allyl 2-{(3S,4R)-4-[(5-methyl-1-[2-(1-methyltetrazol-5-ylthio)ethyl]pyrazol-3-ylcarbonyl)methyl]-3-[(R)-1-t-butyldimethyl silyloxyethyl]-2-oxoazetidinyl}-2-(tri-n-butylphosphoranyl-idene)acetate The title compound was prepared from the product of Preparation 2 by the procedure of Example 10, Preparation 6 and 7 (63% yield); v$_{max}$ (CH$_2$Cl$_2$) 1736, 1682, 1605 cm$^{-1}$.

Preparation 4

Allyl(5R,6S)-6-[(R)-1-hydroxyethyl]-2-{5-methyl-1-[2-(1-methyl-tetrazol-5-ylthio)ethyl]pyrazol-3-yl}carbapen-2-em-3-carboxylate The title compound was prepared from the product of Preparation 3 by the procedure of Example 10, Preparations 8 and 9 (60% yield); u$_{max}$ (CH$_2$Cl$_2$) 3606, 1774, 1718 cm$^{-1}$; d$_H$ (CDCl$_3$) 1.39 (3H, d, J 6.3 Hz), 1.78 (1H, d, J4.9 Hz), 2.29 (3H, s), 3.22 (1H, dd, J 2.9 and 6.7 Hz), 3.28 (1H, dd, J 9 and 18.6 Hz), 3.58 (1H, dd, J 9.8 and 18.5 Hz), 3.78 (2H, t), 3.91 (3H, s), 4.17–4.35 (2H, m), 4.52 (2H, t), 4.68–4.92 (2H, m), 5.24–5.52 (2H, m), 5.92–6.1 (1H, m), 7.01 (1H, s); m/z 459.1689 (M$^+$), calculated for C$_{20}$H$_{25}$N$_7$O$_4$S, 459.1689.

Preparation 5

Sodium (5R,6S)-6-[(R)-1-hydroxyethyl]-2-{5-methyl-1-[2-(1-methyltetrazol-5-ylthio)ethyl]pyrazol-3-yl}carbapen-2-em-3-carboxylate The title compound was prepared from the product of Preparation 4 by the procedure of Example 9, Preparation 10; l$_{max}$ (H$_2$O) 299 nm (e$_m$ 12,167); u$_{max}$ (KBr) 3425 (broad), 1760, 1608 (shoulder), 1577 cm$^{-1}$; d$_H$ (D$_2$O) 1.36 (3H, d, J 6.4 Hz), 2.34 (3H, s), 3.02–3.22 (2H, m), 3.53 (1H, dd, J 2.85, 5.95 Hz), 3.78–3.87 (2H, m), 3.93 (3H, s), 4.25–4.38 (2H, m), 4.4–4.55 (2H, m), 6.42 (1H, s).

EXAMPLE 15

Sodium (5R,6S)-2-[1-(2-acetamidoethyl)-5-methylpyrazol-3-yl]-6-[(1R)-1-hydroxyethyl]carbapen-2-en-3-carboxylate Preparation 1

3-Acetyl-1-(2-hydroxyethyl)-5-methylpyrazole

1M Aqueous hydrochloric acid (39 ml) was added to a stirred solution of the silyl ether previously described in example 11, preparation 4 (5.93 g) in methanol (100 ml) at room temperature. After 1.5 h stirring, sodium hydrogen carbonate was added to the reaction mixture to neutralize it. The mixture was filtered and the solid washed with methanol. The filtrate and washings were concentrated to an oily solid which was dried under vacuum at ambient temperature for 1 h. The solid was then stirred with acetone (75 ml) for 0.25 h and the undissolved solid filtered off and washed with acetone (20 ml). The filtrate was concentrated to a solid, dried under vacuum at room temperature for 1 h then stirred with hexane (100 ml). The undissolved solid was filtered off and identified as the title compound (3.4 g, 95%), m.p. 78°–9° C. (Found: C, 57.26; H, 7.30: N, 16.26%. C$_8$H$_{12}$N$_2$O$_2$ requires C, 57.13; H, 7.19; 16.66%); d$_H$ (CDCl$_3$) 2.32 (3H, s), 2.53 (3H, s), 3.12 (1H, t, J 6.2), 4.054.11 (2H, m), 4.16–4.20 (2H, m), 6.55 (1H, s).

Preparation 2

3-Acetyl-1-(2-methanesulfonyloxyethyl)-methylpyrazole

Methanesulfonyl chloride (0.86 ml) was added dropwise to a stirred solution of the alcohol described in example 15 preparation 1 (1.86 g) in dry pyridine (19 ml) at 0° C. under argon. The solution was then allowed to warm to room temperature over 3 h. The reaction mixture was concentrated to a solid which was purified by chromatography over silica gel eluting with acetone/toluene mixtures to yield the title compound as a white solid (2.55 g. 93%), m.p. 108°–9° C. (Found C, 44.02; H, 5.85; N, 11.47%. $C_9H_{14}N_2O_4S$ requires C, 43.89; H, 5.73; N, 11.37%); $v_{max}$ $(CHCl_3)/cm^{-1}$ 3021, 1683, 1367; $\delta_H$ $(CDCl_3)$ 2.35 (3H, s), 2.53 (3H, s), 2.87 (3H, s), 4.41 (2H, t, J5.4), 4.66 (2H, t, J5.4), 6.54 (1H, s); m/z (EI) 246 ($M^+$, 88%), 231 ($M^+$—$CH_3$, 100), 167 ($M^+$—$SO_2CH_3$, 95).

Preparation 3

3-Acetyl-1-(2-azidoethyl)-5-methylpyrazole

A mixture of the mesylate described in example 15, preparation 2 (2.54 g), sodium azide (3.4 g), tetrabutylammonium hydrogen sulfate (3.53 g) in N,N-dimethylformamide (70 ml) was stirred and heated at 60° C. for 9 h under argon. The reaction mixture was concentrated to an oily solid which was partitioned between dichloromethane (100 ml) and saturated brine (100 ml). The fraction was reextracted with dichloromethane (50 ml) and the combined organic extracts were dried ($Na_2SO_4$) and concentrated to an oil which was purified by chromatography over silica gel, eluting with mixtures of acetone/toluene to yield the title compound as a colourless oil (1.91 g, 96%) $v_{max}$ $(CHCl_3)/cm^{-1}$ 3014, 2105, 1682; $\delta_H$ $(CDCl_3)$ 2.34 (3H, s), 2.54 (3H, s), 3.79 (2H, t, J 5.46), 4.21 (2H, t, J5.5), 6.54 (1H, s); m/z (EI) 193 ($M^+$, 26%), 137 ($CH_2N_3$, 100) (Found m/z 193.0963. $C_8H_{11}N_5O$ requires 193.0964).

Preparation 4

(3S,4R)-[(R)-1-t-Butyldimethylsilyloxyethyl]-4-{[1-(2-azidoethyl-5-methylpyrazol-3-ylcarbonyl]methyl}azetidin-2-one Lithium bis(trimethylsilyl)amide (9.8 ml, 1M in tetrahydrofuran) was added over 5 min to a stirred solution of the azido compound described in example 15, preparation 3 (1.9 g) in dry, tetrahydrofuran (30 ml) at –78° C. under argon. The solution was stirred at this temperature for 0.5 h before a solution of 4-acetoxy-3-[(R)-1-t-butyldimethylsilyloxyethyl]azetidin-2-one (2.83 g) in dry tetrahydrofuran (15 ml) was added over 10 min. The whole was stirred at –78° C. for 0.75 h and then left at –20° C. for 15 h. The mixture was then quenched by addition of saturated ammonium chloride solution after which ethyl acetate (300 ml) was added with siring for 5 min. After separating the layers the aqueous fraction was extracted with ethyl acetate (100 ml) and the combined organic fractions dried ($Na_2SO_4$) and concentrated to an oil which was purified by chromatography over silica gel eluting with mixtures of acetone/toluene to yield the title compound as an oil (1.79 g, 43%) $v_{max}$ $(CHCl_3)/cm^{-1}$ 3411, 3055, 2956, 2106, 1761, 1682; $\delta_H$ $(CDCl_3)$ 0.08 (6H, s), 0.87 (9H, s), 1.21 (3H, d, J6.3), 2.36 (3H, s) 2.89 (1H, dd, J 2.4, 4.8), 3.15 (1H, dd, J 10.0, 17.3), 3.50 (1H, dd, J 3.4, 17.3), 3.79 (2H, t, J 5.9), 4.10 (1H, dt, J 3.2, 10.0), 4.21 (3H, t, J 5.9), 6.08 (1H, s), 6.56 (1H, s); m/z ($NH_3DCI$) 421 ($MH^+$, 48%), 91 (100) (Found m/z 420.2301. $C_{19}H_{32}N_6SiO_3$ requires 420.2305).

Preparation 5

(3S,4R)-[(R)-1-t-Butyldimethylsilyloxyethyl]-4-{[1-(2-acetamidoethyl-5-methylpyrazol-3-ylcarbonyl]methyl}azetidin-2-one 3% palladium on carbon (500 mg) was suspended in a solution of the azido compound described in example 15, preparation 4 (1.47 g) in tetrahydrofuran (100 ml) and acetic anhydride (0.66 ml). The mixture was shaken with hydrogen at atmospheric pressure and room temperature for 3 h before being filtered through celite. The filtrate was concentrated to an oil which was purified by chromatography on silica gel eluting with acetone/toluene mixtures followed by methanol/dichloromethane mixtures to yield the title compound as a foam (681 mg, 45%), $v_{max}$ $(CHCl_3)/cm^{-1}$ 3455, 3417, 3017, 1757, 1677; $\delta_H$ $(CDCl_3)$ 0.07 (6H, s), 087 (9H, s), 1.22 (3H, d, J 6.2), 1.97 (3H, s), 2.30 (3H, s), 2.89 (1H, dd, J 3.0, 5.1), 3.15 (1H, dd, J 17.1, 10.1), 3.45 (1H, dd, J 17.1, 3.4), 3.71 (2H q, J 5.8), 4.09 (1H, dr, J 3.1, 10.1), 4.16–4.25 (3H, m), 5.94 (1H, br.s), 6.15 (1H, s), 6.55 (1H, s); m/z ($NH_3$ DCI) 437 ($MH^+$, 73%).

Preparation 6

Allyl(3S,4R)-3-[(R)-1-hydroxyethyl]-4-[(5-methyl-1-acetamidoethylpyrazol-3-ylcarbonyl)methyl]-2-oxoazetidin-1-yl}tributylphosphoranylidene acetate The pyrazole compound from example 15, preparation 5 (675 mg), allylglyoxylate monohydrate (246 mg) were combined in toluene (20 ml) and heated with stirring under reflux for 1 h with provision for azeotropic removal of water, trader argon. After cooling to room temperature, triethylamine (431 µl) was added and the solution stirred for 15 h, then concentrated to an oil which was redissolved in toluene (50 ml) and reconcentrated to an oily diastereomeric mixture of hemiaminals (Rf=0.19, 0.26 acetone/toluene 1:1).

To a solution of the mixture of hemiaminals in tetrahydrofuran (15 ml), cooled to –10° C., was added 2,6-lutidine (270 µl) over 2 min. followed by thionyl chloride (136 ul) over 5 min. under argon, arid the mixture stirred at –10 ° C. for 20 min. After this time the mixture was diluted with toluene (15 ml), filtered to remove the undissolved solid and the solid was washed with toluene. The filtrate and washings were combined and concentrated to an oil (Rf=0.35, acetone/toluene 1:1) which was dried under vacuum for 1 h at room temperature. To this oil, suspended in 1,4-dioxan (5 ml), was added tri-n-butylphosphine (1.14 ml) and the mixture was stirred for 1.5 h at room temperature under argon. 2,6-Lutidine (0.2 ml) was then added and the mixture was stirred for a further 1 h before diluting it with ethylacetate (50 ml) and washing the solution with 0.2M aqueous hydrochloric acid (50 ml), saturated sodium hydrogen carbonate solution (50 ml) and bring (50 ml). The organic extract was dried ($MgSO_4$) and concentrated to an oil (Rf=0.16, acetone/toluene 1:1) identified as crude allyl{(3S, 4R)-3-[(R)-1-t-butyldimethylsilyloxyethyl]4-[(5-methyl-1-acetamidoethylpyrazol-3-ylcarbonyl)methyl]-2-oxoazetidin-1-yl}tributylphosphoranylidene acetate.

To a solution of this oil in methanol (20 ml) was added 2M aqueous hydrochloric acid (5 ml) and the whole was stirred at room temperature for 1 h. The mixture was neutralised by addition of saturated sodium hydrogen carbonate solution and it was then extracted with ethyl acetate (3×20 ml). The combined organic extracts were washed with saturated brine, dried (MgSO$_4$) and concentrated to an oil which was purified by chromatography over silica gel eluting with dichloromethane/methanol mixtures to give the title compound as a foam (248 mg, 26% overall) (Rf=0.38, methanol/dichloromethane 1:9), $v_{max}$ (CHCl$_3$)/cm$^{-1}$ 3454(br), 3018, 1739, 1670; $\delta_H$ (CDCl$_3$) 0.9–0.96 (9H, m), 1.24–1.46 (21H, m), 1.94 (3H, s), 2.27 (3H, s), 2.83 (1H, br.s), 3.5–3.7 (4H, m), 4.05–4.20 (4H, m), 4.4–4.5 (2H, m), 5.1–5.34 (1H, m), 5.8–6.1 (2H, m), 6.52 (1H, s); m/z (NH$_3$DCI) 621 (MH$^+$, 8%), 203 (P(C$_4$H$_9$)$_3$H$^+$, 100).

Preparation 7

Allyl{(5R,6S)-6-[(R)-1-hydroxyethyl]-2-(1-acetamido-5-methylpyrazol-3-yl)}carbapen-2-em-3-carboxylate To a stirred solution of the azetidinone compound described in example 15, preparation 6 (274 mg) in dichloromethane (2 ml) was added sequentially triethylamine (83 μl), 4-dimethylaminopyridine (5 mg), trimethylsilylchloride (76 μl). The solution was stirred at room temperature for 0.75 h under argon and then washed with water and brine, dried (Na$_2$SO$_4$) and concentrated to an oil. The oil was dissolved in toluene (50 ml), which had previously been eluted through activated, basic alumina, and to the solution was added hydroquinone (5 mg). This solution was heated under reflux for 2.5 h under argon and then it was concentrated to an oil. The oil was dissolved in tetrahydrofuran (10 ml) and to the solution was added 0.05M aqueous hydrodiloric acid (5 ml). After stirring the solution for 1.5 h at room temperature it was neutralised by addition of saturated sodium hydrogen carbonate solution and then extracted with dichloromethane (2×20 ml). The combined organic extracts were dried (Na$_2$SO$_4$) and concentrated to an oil which was purified by chromatography over silica gel eluting with acetone/toluene mixtures to yield the title compound as a white solid, m.p. 149°–51° C., $v_{max}$(CHCl$_3$)/cm$^{-1}$ 3452 (br), 3375, 3019, 2963, 1774, 1718, 1670; $\delta_H$ (CDCl$_3$) 1.38 (3H, d, J 6.3), 1.86 (1H, d, J 4.9), 1.98 (3H, s), 2.26 (3H, s), 3.21 (1H, dd, J 2.8, 6.9), 3.25 (1H, dd, J 9.0, 18.4), 3.53 (1H, dd, J 9.9, 18.4), 3.69 (2H, q, J 5.9), 4.13 (2H, t, J 5.6), 4.19–4.31 (2H, m), 4.69–4.90 (2H, m), 5.25–5.50 (2H, m), 5.93–6.06 (1H, m), 6.21 (1H, br.s), 6.90 (1H, s); m/z (NH$_3$DCI) 403 (MH$^+$, 359 (M$^+$—COCH$_3$, 100).

Preparation 8

Sodium (5R,6S)-2-[1-(2-acetamidoethyl)-5-methylpyrazol-3-yl]-6-[(1R)-1-hydroxyethyl]carbapen-2-em-3-carboxylate The allyl ester from example 15, preparation 8 (114 mg) in ethylacetate/dichloromethane (2 ml, 1:1) was treated successively with sodium-2-ethylhexanoate (51 mg), triphenyl phosphine (7 mg) and tetrakis (triphenylphosphine) palladium (9.7 mg) at room temperature under argon. After stirring for 1 h, the mixture was concentrated to a solid which was stirred with dry diethyl ether (4 ml) for 0.25 h. The undissolved solid was filtered and dissolved in water (5 ml) and the solution was purified by chromatography over Diaion HP20SS resin eluting with tetrahydrofuran/water mixtures to yield, after lyophilisation of the appropriate pooled fractions, the title compound as an amorphous solid (70 mg, 65%), $v_{max}$ (KBr)/cm$^{-1}$ 3439(br), 1766, 1649; $\lambda_{max}$ (H$_2$O)/nm 299 (ε/dm$^3$ mol$^{-1}$ cm$^{-1}$ 8140) $\delta_H$ (D$_2$O) 1.27 (3H, d, J 6.4), 1.88 (3H, s), 2.20 (3H, s), 3.15–3.21 (2H, m), 3.46 (1H, dd, J 6.0, 2.9), 3.50 (2H, dd, J 6.1, 5.0), 4.12 (2H, dd, J 6.1, 5.0), 4.19–4.28 (2H, m), 6.39 (1H, s); m/z (electrospray) 385 (MNa$^+$, 100%), 363 (MH$^+$, 10).

EXAMPLE 16

Sodium (5R,6S)-2-[1-(2-methylthioethyl)-5-methylpyrazol-3-yl]-6-[(1R)-1-hydroxyethyl]carbapen-2-em-3-carboxylate

Preparation 1

3-Acetal-1-(2-methylthioethyl)-5-methylpyrazole

Sodium thiomethoxide (480 mg) was added portionwise to a stirred solution of the mesylate described in example 15. preparation 2 (1.0 g) in dry N,N-dimethylformamide (10 ml) at 0° C. under argon. The reaction mixture was allowed to warm to room temperature and then left stirring for 1.5 h. The mixture was concentrated under vacuo and the residue was dissolved in ethyl acetate (100 ml) and the solution was washed with water (3×50 ml), brine and then dried (Na$_2$SO$_4$) and concentrated to an oil. The oil was purified by chromatography over silica gel eluting with mixtures of ethylacetate/hexane to yield the title compound as an oil (753 mg, 94%) $v_{max}$ (CH$_2$Cl$_2$)/cm$^{-1}$ 1681, 1605; d$_H$ (CDCl$_3$) 2.04 (3H, s), 2.35 (3H, s), 2.53 (3H, s), 2.96 (2H, t, J 7.2), 4.27 (2H, t, J 7.2) and 6.52 (1H, s); m/z (EI) 198 (M$^+$, 55%). (Found m/z 198.0833. C$_9$H$_{14}$N$_2$OS requires 198.0827).

Preparation 2

(3S,4R)-[(R)-1-t-Butyldimethylsilyloxyethyl]-4-{([1-(2-methylthioethyl)-5-methylpyrazol-3-ylcarbonyl]methyl}azetidin-2-one In the same manner as that described in example 15, preparation 4, the thioether compound described in example 16, preparation 1 (590 mg) in dry tetrahydrofuran (35 ml) was treated with lithium bis(trimethylsilyl)amide (2.99 ml) and the azetidinone (430 mg) in tetrahydrofuran (4 ml) to give, after work-up and purification by chromatography on silica gel (ethylacetate/hexane solvent mixtures), the title compound as an oil (386 mg, 61%) $v_{max}$ (CH$_2$Cl$_2$)/cm$^{-1}$ 3410, 1760, 1680; d$_H$ (CDCl$_3$) 0.06 (6H, s), 0.86 (9H, s), 1.21 (3H, d, J 6.3), 2.05 (3H, s), 2.36 (3H, s), 2.89 (1H, m), 2.96 (3H, t, J 7.1), 3.14 (1H, dd, J 17, 10), 3.48 (1H, dd, J 3.5), 4.0–4.3 (2H, m), 4.28 (2H, t, J 7.1), 6.10 (1H, s), 6.54 (1H, s).

Preparation 3

Allyl{(3S,4R)-3-[(R)-1-hydroxyethyl]-4-[(5-methyl-1-methylthioethylpyrazol-3-ylcarbonyl)methyl]-2-oxoazetidin-1-yl}tributylphosphoranylidene acetate In a similar manner to that described in example 15, preparation 6 the azetidinone described in example 16, preparation 2 (550 mg) was treated with allyl glyoxylate monohydrate (324 mg) in toluene (50 ml) to give an intermediate product (544 mg) which was treated with thionyl chloride (108 μl) and 2, 6-lutidine (176 μl) in tetrahydrofuran (15 ml) to yield the crude diastereomeric chloride intermediate. This intermediate was treated with tri-n-butylphosphine (0.753 ml) and 1,4-dioxan (7 ml) to afford the crude tributylphosphoranylidene intermediate as an oil which was treated with 2M aqueous hydrochloride acid (5 ml) in methanol (15 ml) to give, after purification of the crude product by column chromatography over silica gel (ethylacetate/hexane solvent mixtures), the title compound as a gum (393 mg, 53% overall) $v_{max}$ (CH$_2$Cl$_2$)/cm$^{-1}$ 3459, 1741, 1667, 1636 and 1605; m/z (EI) 609 (M$^+$), m/z (NH$_3$DCI) 610 (MH$^+$).

Preparation 4

Allyl{(5R,6S)-6-[(R)-1-hydroxyethyl]-2-(5-methyl-1-methylthioethylpyrazol-3-yl)}carbapen-2-em-3-carboxylate A solution of the phosphoranylidene compound described in example 16, preparation 3 (392 mg) in toluene (150 ml) was heated under reflux for 4 h under argon. The solution was concentrated to an oil which was purified by chromatography on silica gel eluting with ethylacetate/hexane mixtures to yield the title compound as a solid (168 mg, 67%), $v_{max}$ (CH$_2$Cl$_2$)/cm$^{-1}$ 1773, 1716, 1600; $d_H$ (CDCl$_3$) 1.36 (3H, d, J 6.3), 2.03 (3H, s), 2.32 (3H, s), 2.90 (2H, t, J6.9), 3.2 (1H, m), 3.26 (1H, dd, J 18.4, 8.8), 3.58 (1H, dd, J 18.4, 9.8), 4.1–4.3 (4H, m), 4.6–4.9 (2H, m), 5.26 (1H, dd, J 10.5, 1.3), 5.46 (1H, dd, J 17.3, 1.3), 6.0 (1H, m) and 7.00 (1H, s); m/z (EI) 391 (M$^+$), m/z (NH$_3$DCI) 392 (MH$^+$). (Found m/z 391.1565. C$_{19}$H$_{25}$N$_3$O$_4$S requires 391.1566).

Preparation 5

Sodium (5R,6S)-2-[1-(2-methylthioethyl)-5-methylpyrazol-3-yl]-6-[(1R)-1-hydroxyethyl]carbapen-2-em-3-carboxylate In a similar manner to that described in example 15, preparation 8 the allyl ester described in example 16, preparation 4 (60 mg) was treated with triphenylphosphine (4 mg), sodium-2-ethylhexanoate (28 mg) and tetrakis (triphenylphosphine)palladium (5.8 mg) in dichloromethane/ethylacetate (2 ml, 1:1) to yield, after purification on Diaion HP20SS resin (tetrahydrofuran/water solvent mixtures), a lyophilized amorphous solid (38 mg, 66%), $v_{max}$ (KBr)/cm$^{-1}$ 3416(br), 1752, 1608, 1587; $l_{max}$ (H$_2$O)/nm 296 (e/dm$^3$ mol$^{-1}$ cm$^{-1}$ 8950); $d_H$ (D$_2$O) 1.26 (3H, d, J 6.3), 1.96 (3H, s), 2.35 (3H, s), 2.89 (2H, t, J 6.5), 3.12 (1H, m), 3.19 (1H, m), 3.44 (1H, m), 4.23 (4H, m), 6.42 (1H, s); m/z (electrospray), 374 (MH$^+$, 70%).

EXAMPLE 17

Sodium (5R,6S)-6-[(1R)-1-Hydroxyethyl]-2-(1-methyl-5-ethylpyrazol-3-yl)carbapen-2-em-3-carboxylatea)

a) Ethyl 5-Ethyl-1-methylpyrazole-3-carboxylate

Ethyl 2,4-dioxohexanoate (12 g) in glacial acetic acid (75 ml) was cooled in an ice-bath and treated with methylhydrazine (3.21 g) in a dropwise fashion over 5–10 m. On complete addition the ice cooling was removed and the yellow homogeneous solution stirred at room temperature for ca. 2 h. The acetic acid was then removed in vacuo and the residual oil re-dissolved in ethyl acetate (~100 mls). The ethyl acetate solution was washed with saturated sodium hydrogen carbonate (3×) and brine. After drying over anhydrous magnesium sulphate the solvent was evaporated. The crude material was purified by silica gel chromatography eluting with 20–70% ethyl acetate/hexane giving the title compound as a pale yellow oil, (6.656 g, 52%); $d_H$ (CDCl$_3$) 1.28 (3H, t, J7.6 Hz), 1.38 (3H, t, J7.1 Hz), 2.61 (2H, q, J7.6 Hz), 3.84 (3H, s), 4.38 (2H, q, J7.1 Hz) and 6.58 (1H, s).

b) 5-Ethyl-1-methylpyrazole-3-carboxylic acid

Ethyl 5-ethyl-1-methylpyrazole-3-carboxylate (6.86 g) in ethanol (70 ml) was treated with sodium hydroxide (1.58 g) in water (30 ml) and heated under reflux for 6 h. The solution was concentrated and the aqueous phase washed with ethyl acetate before adding dichloromethane (50 ml). The solution was acidified with 5M hydrochloric acid, and the mixture exhaustively extracted with dichloromethane. The remaining undissolved solid was filtered off suspended in water and the pH adjusted to 6 with saturated sodium hydrogen carbonate. The solution was again extracted with dichloromethane. The combined organic layers were dried over anhydrous magnesium sulphate and concentrated to give the title compound as a white solid, (2.72 g, 47%); (Found: M$^+$, 154.0742. C$_7$H$_{10}$N$_2$O$_2$ requires M, 154.0742); $n_{max}$ (CH$_2$Cl$_2$) 3689 and 1760 cm$^-$; $d_H$(CDCl$_3$) 1.30 (3H, t, J7.4 Hz), 2.64 (2H, q, J7.4 Hz), 3.88 (3H, s) and 6.65 (1H, s).

c) N-Methoxy-N-methyl-5-ethyl-1-methylpyrazole-3-carboxamide 5-Ethyl-1-methylpyrazole-3-carboxylic acid (2.5 g) in dichloromethane (50 ml) was treated with DMF (0.12 ml) and cooled under argon in an ice-bath. The solution was treated with oxalyl chloride (2.2 g) in dichloromethane (25 ml) in a dropwise fashion. After complete addition the reaction mixture was maintained at 0° C. for 25 m. and then allowed to warm to room temperature. The solution was evaporated and the residue re-dissolved in toluene (100 ml) and concentrated again. The crude acid chloride was taken up in dichloromethane (50 ml), and treated with N,O-dimethylhydroxylamine hydrochloride (1.72 g), cooled in an ice-bath and pyridine (2.86 ml) added. The reaction mixture was allowed to stir at room temperature for 2 h. The reaction mixture was washed with brine, dried over anhydrous magnesium sulphate and concentrated to an oil. The product was purified by 'flash' silica gel chromatography to give the title compound as a yellow oil, (2.995 g, 94%); (Found: M$^+$, 197.1167. C$_9$H$_{15}$N$_3$O$_2$ requires M, 197.1164); $n_{max}$ (CH$_2$Cl$_2$) 1640, 1484 and 1374 cm$^{-1}$; $d_H$(CDCl$_3$) 1.28 (3H, t, J7.5 Hz), 2.62 (2H, q, J7.5 Hz), 3.43 (3H, s), 3.76 (3H, s), 3.83 (3H, s) and 6.72 (1H, s).

d) 3-Acetyl-5-ethyl-1-methylpyrazole

N-Methoxy-N-methyl-5-ethyl-1-methylpyrazole-3-carboxamide (2.9 g) in dry tetrahydrofuran (100 ml), under argon was cooled to −20° C. and treated with methylmagnesium bromide (9.8 ml of a 3M solution in ether). A precipitate was initially formed that re-dissolved on complete addition. The reaction mixture was stirred at 0° C. for 2 h. and then poured into saturated ammonium chloride. The aqueous phase was extracted with ethyl acetate and the combined organic phases washed with brine, dried over anhydrous magnesium sulphate and concentrated to a brown oil. The crude product was purified by silica gel chromatography eluting with 50% ethyl acetate/hexane to give the title compound as a pale brown oil, (1.97 g, 88%); (Found: M$^+$, 152.0950. C$_8$H$_{12}$N$_2$O requires M 152.0950); $n_{max}$ (CH$_2$Cl$_2$) 1693, 1472, 1376 and 1352 cm$^{-1}$; $d_H$(CDCl$_3$) 1.28 (3H, t, J7.4 Hz), 2.54 (3H, s), 2.61 (2H, q, J7.4 Hz), 3.84 (3H, s) and 6.56 (1H, s).

e) (3R,4S)-3-[(R)-1-t-Butyldimethylsilyloxyethyl]-4-[2-(5-ethyl-1-methylpyrazol-3-yl)-2-oxoethyl]azetidin-2-one 3-Acetyl-5-ethyl-1-methylpyrazole (1.96 g) in dry tetrahydrofuran (70 ml), under argon was cooled to −78° C. and treated with lithium bis(trimethylsilylamide) (12.9 ml of a 1M solution in hexanes) in a dropwise fashion. After 30 m at −78° C. a solution of (3R,4R)-4-acetoxy-3-[(1R)-tert-butyldimethylsilyloxy)ethyl]azetidin-2-one in dry tetrahydrofuran (20 ml) was added in the same fashion via syringe. The reaction mixture was maintained at this temperature for 4 h. The reaction mixture was quenched by the addition of 5% citric acid (100 ml) and the solution allowed to warm to room temperature. The aqueous phase was separated and extracted with ethyl acetate. The combined organic phases were washed with brine dried over anhydrous magnesium sulphate and concentrated to give a pale yellow gum. Silica gel chromatography eluting with 50. 70 and then 90% ethyl acetate/hexane afforded recovered starting material (0.484 g, 25%). The title compound was then eluted and obtained as a colourless gum, (2.24 g, 46%); (Found: M$^+$, 379.2292. C$_{19}$H$_{37}$N$_3$O$_3$Si requires M 379.2291); n$_{max}$ (CH$_2$Cl$_2$) 3410, 1760 and 1678 cm$^{-1}$; d$_H$(CDCl$_3$) 0.06 (6H, s), 0.86 (9H, s), 1.20 (3H, d, J6.2 Hz), 2.62 (2H, q, J6.2 Hz), 2.89 (1H, dd, J1.8,4.9 Hz), 3.14 (1H, dd, J10.0, 17.1 Hz), 3.48 (1H, dd, J3.4,17.1 Hz), 3.84 (3H, s), 4.11 (1H, m), 4.20 (1H, m), 6.11 (1H, br. s) and 6.56 (1H, s); m/z (CI, +ve ion, ammonia) 380 (MH$^+$).

f) Allyl 2-{(3R,4S)-3-[(R)-1-t-Butyldimethylsilyloxyethyl]-4-[2-(5-ethyl-1-methylpyrazol-3-yl)-2-oxoethyl]azetidin-2-on-1-yl}-2-hydroxyacetate (3R,4S)-3-[(R)-1-t-Butyldimethylsilyloxyethyl]-4-[2-(5-ethyl-1-methylpyrazol-3-yl)-2-oxoethyl]azetidin-2-one (219 g) and allyl hyoxylate hydrate (1.67 g) in toluene (70 ml) were heated under reflux with a Dean-Staark water separator for 4 h. T.l.c. analysis showed absence of starting material. The solution was evaporated and the residue re-dissolved in ethyl acetate (70 ml), washed with water (5×50 ml), brine, dried over anhydrous magnesium sulphate and concentrated to a gum. The title compound was sufficiently pure by t.l.c. for the next step, (2.994 g, quant.); n$_{max}$ (CH$_2$Cl$_2$) 3523(w), 1759 and 1675 cm$^{-1}$; m/z (CI, +ve ion, ammonia) 494 (MH$^+$), 511 (MNH$_4^+$).

g) Allyl 2-{(3 R,4S)-3-[(R)-1-t-Butyldimethylsilyloxyethyl]-4-[2-(5-ethyl-1-methylpyrazol-3-yl)-2-oxoethyl]azetidin-2-on-1-yl}-2-(tri-n-butylphosphoranylidene)acetate Allyl 2-{(3R,4S)-3-[(R)-1-t-Butyldimethylsilyloxyethyl]-4-[2-(5-ethyl-1-methylpyrazol-3-yl)-2-oxoethyl]azetidin-2-on-1-yl}-2-hydroxyacetate (1.943 g) in dry tetrahydrofuran (70 ml), under argon was cooled to −10° C. and treated with 2,6-lutidine (0.69 ml) followed by thionyl chloride (0.43 ml) giving a white precipitate. After 1 h. the reaction mixture was diluted with toluene, filtered through Kieselghur and concentrated to dryness. A further portion of toluene was added and the mixture re-evaporated. The crude chloride was then dissolved in dioxan (15 ml) and tri-nbutylphosphine (2.9 ml) added. After 2 h. at room temperature t.l.c. analysis showed no starting material. The reaction mixture was diluted with ethyl acetate, washed with saturated sodium hydrogen carbonate, brine and dried over anhydrous magnesium sulphate. The solution was then concentrated to a yellow oil. The crude phosphorane was disssolved in methanol (50 ml) and treated with 2M hydrochloric acid for 1 h. at room temperature. Saturated sodium hydrogen carbonate was cautiously added to pH 8 and the mixture extracted with ethyl acetate (2×100 ml), washed with brine, dried and concentrated. Purification by silica gel chromatography, eluting with ethyl acetate, 2½% ethanol/ethyl acetate then 5% ethanol/ethyl acetate to give the title compound as a yellow/orange gum, (1.94 g, 60%); (Found: M$^+$, 563.3493. C$_{30}$H$_{50}$N$_3$O$_5$P requires M 563.3488); n$_{max}$ (CH$_2$Cl$_2$) 3676, 3599, 1740, 1668 and 1605 cm$^{-1}$.

h) Allyl(5R,6S)-2-(5-Ethyl-1-methylpyrazol-3-yl)-6-[(R)-1-hydroxyethyl]carbapen-2-em-3-carboxylate Allyl 2-{(3R,4S)-3-[(R)-1-t-Butyldimethylsilyloxyethyl]-4-[2-(5-ethyl-1-methylpyrazol-3-yl)-2-oxoethyl]azetidin-2-on-1-yl}-2-(tri-n-butylphosphoranylidene)acetate (1.94 g) in toluene (650 ml; 3 mgs/ml) was heated under reflux for a total of 7 h. T.l.c. analysis showed only a small mount of unreacted starting material. The solution was concentrated and purified by silica gel chromatography, eluting with 5% then 10% acetone/ethyl acetate. The product was obtained as an off white, crystalline solid. Trimration with ether, followed by filtration gave the title compound as a colourless crystalline solid, (356 mg; 30% ); (Found: M$^+$, 345.1689. C$_{18}$H$_{23}$N$_3$O$_4$ requires M 345.1689); n$_{max}$ (CH$_2$Cl$_2$) 3603, 1774, 1716, 1599(w) and 1542(w) cm$^{-1}$; d$_H$(CDCl$_3$) 1.28 (3H, t, J7.4 Hz), 1.36 (3H, d, J6.3 Hz), 1.85 (1H, d, J5.0 Hz), 2.61 (2H, d, J7.4 Hz), 3.19 (1H, dd, J2.8,6.7 Hz), 3.27 (1H, dd, J9.0,18.5 Hz), 3.59 (1H, dd, J9.8,18.5 Hz), 3.84 (3H, s), 4.24 (2H, m), 4.79 (2H, m), 5.27 (1H, m), 5.46 (1H, m), 6.01 (1H, m) and 7.02 (1H, s).

i) Sodium (5R,6S)-2-(5-Ethyl-1-methylpyrazol-3-yl)-6-[(R)-1-hydroxyethyl]carbapen-2-em-3-carboxylate Allyl(5R,6S)-2-(5-Ethyl-1-methylpyrazol-3-yl)-6-[(R)-1-hydroxyethyl]carbapen-2-em-3-carboxylate (348 mg) in 1:1 ethyl acetate/dichloromethane (8 ml), under argon was treated successively with sodium 2-ethylhexanoate (198 mg), triphenylphosphine (27 mg) and tetrakis(triphenylphosphine)palladium (0), (38 mg). After a few seconds an off-white precipitate was formed. The reaction mixture was stirred at room temperature for 30 m. T.l.c. analysis (20% acetone/ethyl acetate showed no remaining starting material. The solvents were removed in vacuo and the residual solid stirred with diethyl ether (20 ml). The white solid was filtered off washed with ether and dried. This solid was dissolved in water (10 ml) and chromatographed on HP20SS resin eluting with 1–5% tetrahydrofuran/water (100 ml portions ). The combined fractions containing the product (by h.p.l.c.), were concentrated and freeze-dried to give the title compound as an amorphous pale yellow solid, (3.14 mg, 95%); n$_{max}$ (KBr) 1755, 1614, 1586 and 1386 cm$^{-1}$; d$_H$(D$_2$O) 1.17 (3H, t, J7.5 Hz), 1.26 (3H, d, J6.4 Hz), 2.56 (2H, q, J7.5 Hz), 3.16 (2H, m), 3.44 (1H, dd, J2.8,6.0 Hz), 3.68 (3H, s), 4.21 (2H, m) and 6.47 (1H, s). m/z (Electrospray) 328 (MH$^+$), 350 (MNa$^+$), 633 (2MNa$^+$, free acid), 655 (2MH$^+$), 677 (22 MNa$^+$).

EXAMPLE 18 t-Butyloxycarbonyloxymethyl (5R,6S)-2-(1,5-Dimethylpyrazol-3-yl)-6-[(R)-1-hydroxyethyl]carbapen-2-era-3-carboxylate The product from Example 1 (270 mg, 0.86 mmol) was dissolved in N-methylpyrrolidine-2-one (5 ml) under an atmosphere of argon. t-Butyloxycarbonyloxyoxymethyl iodide (560 mg, 1.72 mmol) was added and the reaction stirred at room temperature for 15 minutes. The reaction mixture was diluted with ethyl acetate and washed with water (three times). The organic phase was dried (MgSO$_4$). Purification was accomplished by chromatography on silica gel, loading and eluting with ethyl acetate. The resulting brown oil was triturated with hexane, the residue redissolved in dichloromethane and the solvent removed in vacuo to give the title compound as a foam (220 mg, 50%); δ$_H$ (CDCl$_3$) 1.36 (3H, d, J 6.3 Hz), 1.50 (9H, s), 2.10 (1H, d, J 4.8 Hz), 2.28 (3H, s), 3.23 (1H, dd, J 6.0, 2.8 Hz), 3.21–3.34 (1H, m), 3.62 (1H, dd, J 18.8, 9.8 Hz), 3.78 (3H, s), 3.93 (3H, s), 4.11–4.33 (2H, m), 5.88 and 5.92 (2H, ABq, J 5.9 Hz), 7.04 (1H, s).

EXAMPLE 19

Cyclohexyloxycarbonyloxymethyl(5R,6S)-2-(1,5-Dimethylpyrazol-3-yl)-6-[(R)-1-hydroxyethyl]carbapen-2-em-3-carboxylate The product from Example 1 (126 mg, 0.40 mmol) was dissolved in N-methylpyrrolidine-2-one (2 ml) under an atmosphere of argon. Cyclohexyloxycarbonyloxymethyl iodide (228 mg, 0.80 mmol) was added and the reaction stirred at room temperature for 15 minutes. The isolation of crude product and its subsequent purification were carried out as according to the procedure described in Example 18. The title compound was isolated as a foam (108 mg, 54%); m/z 447.2006 (M$^+$), calculated for $C_{22}H_{29}N_3O_7$, 447.2006; $\nu_{max}$ (CH$_2$Cl$_2$) 2943, 1773, 1594, and 1549 cm$^{-1}$; $\delta_H$ (CDCl$_3$) 1.35 (3H, d, J 8.3 Hz), 1.40–1.60 (6H, m), 1.70–1.80 (2H, m), 1.85–1.95 (2H, m), 2.28 (3H, s), 3.17 (1H, dd, J 6.5, 2.7 Hz), 3.28 (1H, dd, J 18.7, 9.0 Hz)), 3.60 (1H, dd, J 18.7, 9.9 Hz), 3.78 (3H, s), 4.17–4.26 (2H, m), 4.65–4.71 (1H, m) 5.92 and 5.94 (2H, ABq, J 5.7 Hz), 7.05 (1H, s).

EXAMPLE 20

Cyclohexyloxycarbonyloxymethyl(5R,6S)-2-(1-Ethyl-5-methylpyrazol-3-yl)-6-[(R)-1-hydroxyethyl] carbapen-2-em-3-carboxylate The product from Example 10 (174 mg, 0.53 mmol) was dissolved in (2 ml) under an atmosphere of argon. Cyclohexyloxycarbonyloxymethyl iodide (302 mg, 1.06 mmol) in N-methylpyrrolidine-2-one (0.5 ml) was added and the reaction stirred at room temperature for 20 minutes. The isolation of crude product and its subsequent purification were carried out as according to the procedure described in Example 18. The title compound was isolated as a foam (176 mg, 72%), and crystallized from diethyl ether as colourless prisms (137 mg, 56%), m.p. 124°–126° C.; (Found: M$^+$, 461.2151. $C_{23}H_{31}N_3O_7$ requires M 461.2162); $\nu_{max}$ (CH$_2$Cl$_2$) 3603(w), 1772, 735(shoulder), 1596 and 1546 cm$^{-1}$; $\delta_H$(CDCl$_3$) 1.21–1.90 (17H, m), 2.29 (3H, s), 3.18 (1H, dd, J7,6.5 Hz), 3.29 (1H, dd, J9.1,18.8 Hz), 3.64 (1H, dd, J9.8,18.8 Hz 4.08 (2H, q, J7.2 Hz), 4.16–4.30 (2H, m), 4.62–4.72 (1H, m), 5.92 and 5.95 (2H, ABq, J5.7 Hz) and 7.05 (1H, s).

EXAMPLE 21

Sodium (5R,6S)-6-[(1R)-1-hydroxyethyl]-2-[5-methyl-1-(2-methylsulphonylethyl)pyrazol-3-yl]-carbapen-2-em-3-carboxylate

Preparation 1

Allyl{(5R,6S)-6-[(1R)-1-hydroxyethyl]-2-[5-methyl-1-(2-methylsuiphonylethyl)pyrazol-3-yl]}-carbapen-2-em-3-carboxylate To the product of Example 16, preparation 4 (55 mg) in dichoromethane (2 ml) at 0° C. under argon was added m-chloroperoxybenzoic acid (30 mg. 80% purity). After stirring for 0.5 h further m-chloroperoxybenzoic acid (25 mg and 3 mg) was added at 0.5 h intervals. The reaction was stirred for a total of 2 h. then filtered, diluted with ethyl acetate and washed with a solution of sodium sulphite, aqueous sodium bicarbonate, water, brine, dried and evaporated. The residue was chromatographed on silica gel eluting with mixtures of ethyl acetate/hexane and mixtures of ethanol/ethyl acetate to afford the title compound as an oil (15 mg. 25%) $\nu_{max}$ (CH$_2$Cl$_2$) 3606, 1775, 1719, 1602, 1314 and 1189 cm$^{-1}$; $\delta_H$(CDCL$_3$) ppm 1.36 (3H, d, d6.3 Hz), 2.34 (3H, s), 2.50 (3H.s), 3.15–3.30 (2H.m), 3.56 (1H.dd, d 19 and 9.9 Hz), 3.63 (2H,t, d 6 Hz), 4.2–4.3 (2H, m), 4.48 (2H, t, d 6 Hz), 4.64–4.9 (2H, m),5.26 (1H,dd, J 10.5 and 1.2 Hz), 5.45 (1H, ddJ 17.3 and 1.5 Hz), 5.9–6.1 (1H, m) and 6.99 (1H, s).

Preparation 2

Sodium (5R,6S)-6-[(1R)-1-hydroxyethyl]-2-[5-methyl-1-(2-methylsulphonylethyl)pyrazol-3-yl]-carbapen-2-em-3-carboxylate In a similar manner to that described in example 15, preparation 8 the allyl ester described in example 21 preparation 1 (15 mg) was convened to the title compound.

EXAMPLE 22

Sodium (5R,6S)-2-[1-[2-(N,N-dimethylaminocarbonyloxy)ethyl]-5-methylpyrazol-3-yl]-6-[(1R)-1-hydroxyethyl]carbapen-2-em-3-carboxylate

Preparation 1

3-Acetyl-1-[2-(chlorocarbonyloxy)ethyl]-5-methylpyrazole

3-Acetyl-1-(2-hydroxyethyl)-5-methylpyrazole (505 mg, prepared as described in Example 12, Preparation 1) in dry dichloromethane (5 ml) under an atmosphere of argon was treated with a solution of phosgene in toluene (12.5% w/w, 5.22 ml) and the mixture stirred for 1.5 h. The solvents were then removed, dichloromethane was added and removed using a rotary evaporator to give 3-acetyl-1-[2-(chlorocarbonyloxy)ethyl]-5-methylpyrazole; $\nu_{max}$ (CH$_2$Cl$_2$) 1777 and 1684 cm$^{-1}$.

Preparation 2

3-Acetyl-1-[2-(N,N-dimethylaminocarbonyloxy) ethyl]-5-methylpyrazole 3-acetyl-1-[2-(chlorocarbonyloxy)ethyl]-5-methylpyrazole (prepared in Example 22, Preparation 1) in dry dichloromethane (20 ml) was treated with dimethylamine hydrochloride (367 mg) and pyridine (712 mg) and the mixture stirred for 1.5 h. The mixture was then partitioned between ethyl acetate and 1M aqueous HCl. The organic phase was separated, washed with 1M aqueous HCl, saturated aqueous NaHCO$_3$ and brine then dried over MgSO$_4$ and evaporated. The residue was chromatographed on silica gel eluting with ethyl acetate/hexane mixtures to give 3-acetyl-1-[2-(N,N-dimethylammocarbonyloxydethyl]-5-methylpyrazole (222 mg); $\nu_{max}$ (KBr) 1697 and 1683 cm$^{-1}$; $\delta_H$ (CDCl$_3$) 2.31 (3H,s), 2.53 (3H, s), 2.82 (3H, s), 2.91 (3H, s), 4.4 (4H, m); Found m/z 239.1273 $C_{11}H_{17}N_3O_3$ requires 239.127.

Preparation 3

(3S,4R)-4-[1-[[2-(N,N-Dimethylaminocarbonyloxy) ethyl]-5-methylpyrazol-3-yl]carbonylmethyl]-3-[(R)-1-tert-butyldimethylsilyloxyethyl]azetidin-2-one 3-Acetyl-1-[2-(N,N-dimethylaminocarbonyloxy)ethyl]-5-methylpyrazole (478 mg) was reacted as described in Example 4, Preparation 5 to give (3S,4R)-4-[1-[[2-(N,N-dimethylaminocarbonyloxy)ethyl]-5-methylpyrazol-3-yl] carbonylmethyl]-3-[(R)-1-tert-butyldimethylsilyloxyethyl] azetidin-2-one (393 mg, 42%); $\nu_{max}$ (CH$_2$Cl$_2$) 1761, 1704, 1259 and 1189 cm$^{-1}$; $\delta_H$ (CDCl$_3$) 0.05 (6H, s), 0.87 (9H, s), 1.20(3H,d, J 6.2 Hz), 2.31 (3H, s), 2.81 (3H, s), 2.89 (3H, s), 2.90 (1H, m), 3.14 (1H,dd, J9.9, 17 Hz), 3.48 (1H, dd, J3.5, 17 Hz), 4.13 (1H,m), 4.22 (1H,m), 4.34 (2H,t, J 5.2 Hz), 4.45 (2H,t, J 5.2 Hz), 6.11 (1h, s), 6.53 (1H,s).

Preparation 4

Allyl[(3S,4R)-4-[1-[[2-(N,N-dimethylaminocarbonyloxy)ethyl]-5-methylpyrazol-3-yl]carbonylmethyl]-3-[(R)-1-tert-butyldimethylsilyloxyethyl]-2-oxoazetidin-1-yl]triphenylphosphoranylidene acetate (3S,4R)-4-[1-[[2-(N,N-Dimethylaminocarbonyloxy)ethyl]-5-methylpyrazol-3-yl]carbonylmethyl]-3-[(R)-1-tert-butyldimethylsilyloxyethyl]azetidin-2-one (2.39 g) was reacted by the method described in Example 4, Preparation 6 (with replacement of tributylphosphine by triphenylphosphine) to give allyl[(3S,4R)-4-[1-[[2-(N,N-dimethylaminocarbonynloxy]-5-methylpyrazol-3-yl]carbonylmethyl]-3-[(R)-1-tert-butyldimethylsilyloxyethyl]-2-oxoazetidin-1-yl] triphenylphosphoranylidene acetate (2.69 g, 64%); $v_{max}$ (CH$_2$Cl$_2$) 1736, 1703, 1275, 1190 cm$^{-1}$.

Preparation 5

Allyl[(5R,6S)-2-[1-[2-(N,N-dimethylaminocarbonyloxy)ethyl]-5-methylpyrazol-3-yl]]-6-[(R)-1-hydoxyethyl]carbapen-2-em-3-carboxylate Allyl[(3S,4R)-4-[1-[[2-(N,N-dimethylaminocarbonyloxy)ethyl]-5-methylpyrazol-3-yl]carbonylmethyl]-3-[(R)-1-tert-butyldimethylsilyloxyethyl]-2-oxoazetidin-1-yl]triphenylphosphoranylidene acetate (2.64 g) was reacted as described in Example 4, Preparation 7 to give allyl(5R,6S)-2-[1-[2-(N,N-dimethylaminocarbonyloxy)ethyl]-5-methylpyrazol-3-yl]-6-[(R)-1-hydoxyethyl]carbapen-2-em-3-carboxylate (285 mg, 20%); $v_{max}$ (CH$_2$Cl$_2$) 1774, 1703, 1311, 1275, and 1187 cm$^{-1}$; $\delta_H$ (CDCl$_3$) 1.36(3H, d, J 6.3 Hz), 1.9 (1H,d,J 4.6 Hz), 2.28 (3H,s), 2.81 (3H, s), 2.90 (3H,s), 3.19 (1H,dd, J 2.8, 6.7 Hz), 3.27 (1H,dd, J 9, 18 Hz), 3.59 (1H,dd,J 10, 18 Hz), 4.2 (1H,m), 4.28 (2H,m), 4.40 (2H, m), 4.43 (1H,m), 4.80 (2H, m), 5.27 (1H,dd,J 1.3, 9.2 Hz) 5.47 (1H, m), 6.0 (1H,m), 7.03 (1H,s); m/z (EI) 432.

Preparation 6

Sodium (5R,6S)-2-[1-[2-(N,N-dimethylaminocarbonyloxy)ethyl]-5-methylpyrazol-3-yl]-6-[(1R)-1-hydroxyethyl]carbapen-2-em-3-carboxylate The title compound was prepared from allyl[(5R,6S)-2-[1-[2-(N,N-dimethylaminocarbonyloxy)ethyl]-5-methylpyrazol-3-yl]]-6-[(R)-1-hydoxyethyl]carbapen-2-em-3-carboxylate as described in Example 4, Preparation 8.

We claim:
1. A process for the preparation of a compound of formula (I):

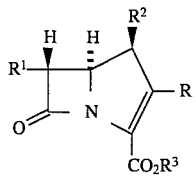

in which R is:

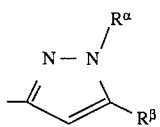

wherein $R^\alpha$ is hydrogen, optionally substituted (C$_{1-6}$)alkyl or optionally substituted aryl;

$R^\beta$ is hydrogen, optionally substituted (C$_{1-6}$)alkyl or optionally substituted aryl; or $R^\alpha$ and $R^\beta$ together form an optionally substituted 5 or 6 membered heterocyclic ring with or without additional heteroatoms;

$R^1$ is (C$_{1-6}$)alkyl which is unsubstituted or substituted by fluoro, a hydroxy group which is optionally protected by a readily removable hydroxy protecting group, or by an amino group which is optionally protected by a readily removable amino protecting group;

$R^2$ is hydrogen or methyl, and

—CO$_2$R$_3$ is carboxy or the group R$^3$ is a readily removable carboxy protecting group, or a pharmaceutically acceptable salt thereof, which process comprises treating a compound of formula (X):

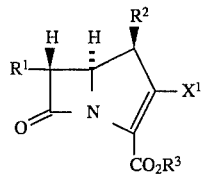

in which $R^1$ and $R^2$ are as hereinbefore defined, $R^3$ is a readily removable carboxy protecting group and $X^1$ is a leaving group, with a compound of formula (XI):

M—R (XI)

in which M is a metallo group and R is as hereinbefore defined;

in a cross-coupling reaction in the presence of a cross-coupling reaction catalyst and thereafter and if necessary removing any protecting group and thereafter optionally forming a pharmaceutically acceptable salt thereof.

2. A process according to claim 1, wherein $X^1$ is trifluoromethanesulphonyloxy, methanesulphonyloxy, 4-toluene sulphonyloxy, fluorosulphonyloxy, chloro, bromo, iodo or diphenoxyphosphoryloxy.

3. A process according to claim 2, wherein M is $R^{14}R^{15}R^{16}$Sn, B(OR)$_2$ or ZnCl in which $R^{14}$, $R^{15}$ and $R^{16}$ may the same or different and are each (C$_{1-6}$)alkyl.

4. A process according to claim 3, wherein $R^{14}$, $R^{15}$ and $R^{16}$ are the same and are selected from methyl and n-butyl.

5. A process according to claim 1, wherein the cross coupling catalyst is a palladium compound.

* * * * *